(12) United States Patent
Rennard et al.

(10) Patent No.: US 8,486,909 B2
(45) Date of Patent: Jul. 16, 2013

(54) COMPOSITIONS AND METHODS FOR THE DIAGNOSIS AND TREATMENT OF INFLAMMATORY DISORDERS AND FIBROTIC DISEASE

(75) Inventors: Stephen I. Rennard, Omaha, NE (US); Tadashi Sato, Omaha, NE (US); Xiang-der Liu, Omaha, NE (US); Olaf Holz, Grosshansdorf (DE); Helgo Magnussen, Grosshansdorf (DE)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 13/380,320

(22) PCT Filed: Jun. 24, 2010

(86) PCT No.: PCT/US2010/039783
§ 371 (c)(1),
(2), (4) Date: Jan. 26, 2012

(87) PCT Pub. No.: WO2010/151640
PCT Pub. Date: Dec. 29, 2010

(65) Prior Publication Data
US 2012/0121697 A1    May 17, 2012

Related U.S. Application Data

(60) Provisional application No. 61/279,310, filed on Dec. 23, 2009, provisional application No. 61/219,913, filed on Jun. 24, 2009.

(51) Int. Cl.
*A61K 48/00* (2006.01)
(52) U.S. Cl.
USPC ......... 514/44; 536/24.5; 536/24.31; 536/24.1
(58) Field of Classification Search
None
See application file for complete search history.

(56) References Cited

U.S. PATENT DOCUMENTS
2007/0092882 A1 * 4/2007 Wang et al. ...................... 435/6

OTHER PUBLICATIONS

Shim et al. (FEBS Journal 2010, vol. 277: 4814-4827).*
Harper, K.A., et al. "Complexity of COX-2 gene regulation." Biochem Soc Trans. Jun. 2008;36(Pt 3):543-5.
Chakrabarty, A., et al. "MicroRNA regulation of cyclooxygenase-2 during embryo implantation." Proc Natl Acad Sci U S A. Sep. 18, 2007;104(38):15144-9. Epub Sep. 11, 2007.
Sato, T., et al. "Reduced miR-146a increases prostaglandin $E_2$ in chronic obstructive pulmonary disease fibroblasts." Am J Respir Crit Care Med. Oct. 15, 2010;182(8):1020-9. Epub Jun. 3, 2010. [Abstract].

* cited by examiner

*Primary Examiner* — Kimberly Chong
(74) *Attorney, Agent, or Firm* — Dann, Dorfman, Herrell & Skillman; Kathleen D. Rigaut

(57) ABSTRACT

Compositions and methods are disclosed for the treatment and diagnosis of inflammatory diseases and disorders, including pulmonary diseases and fibrotic disorders, including COPD.

12 Claims, 34 Drawing Sheets

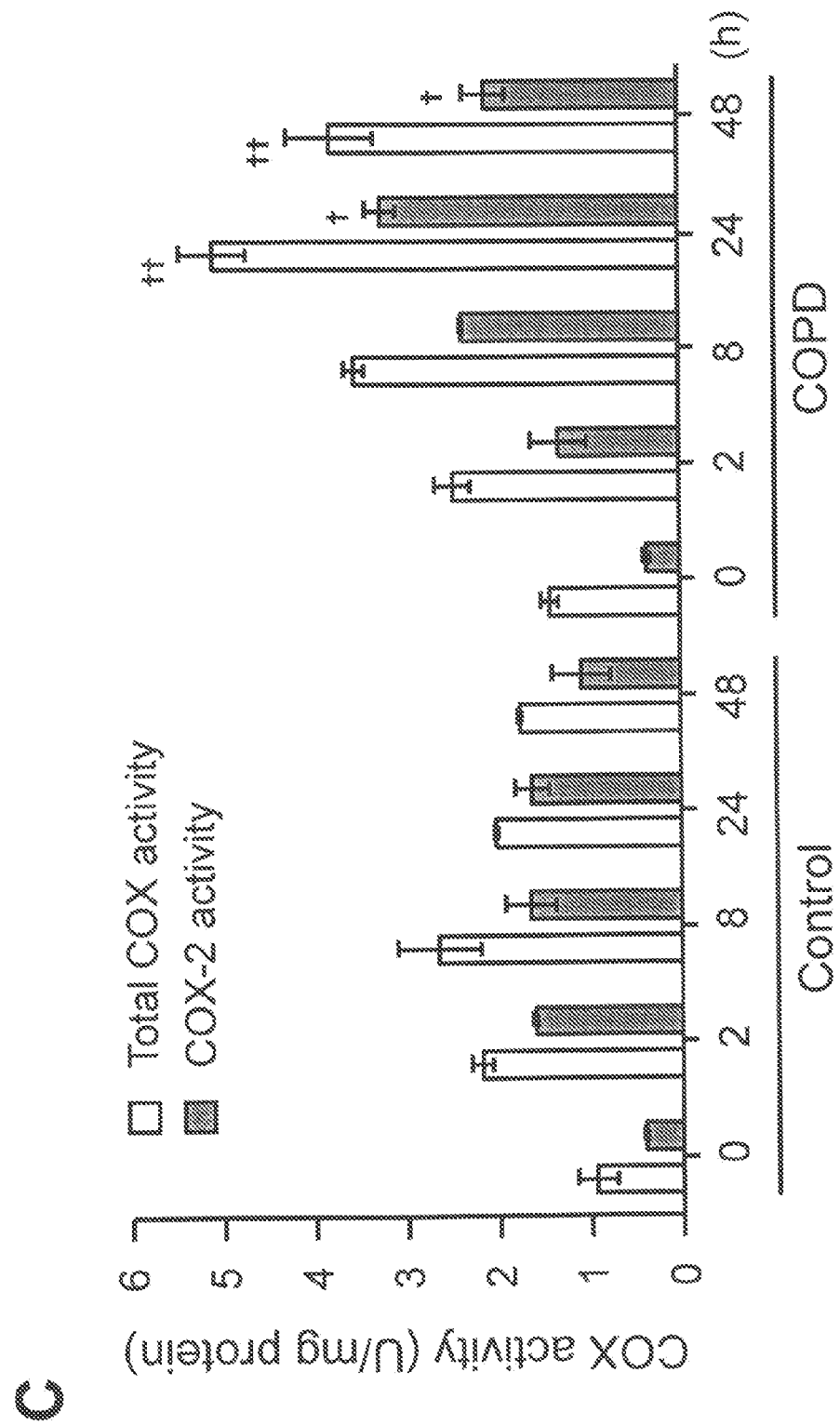

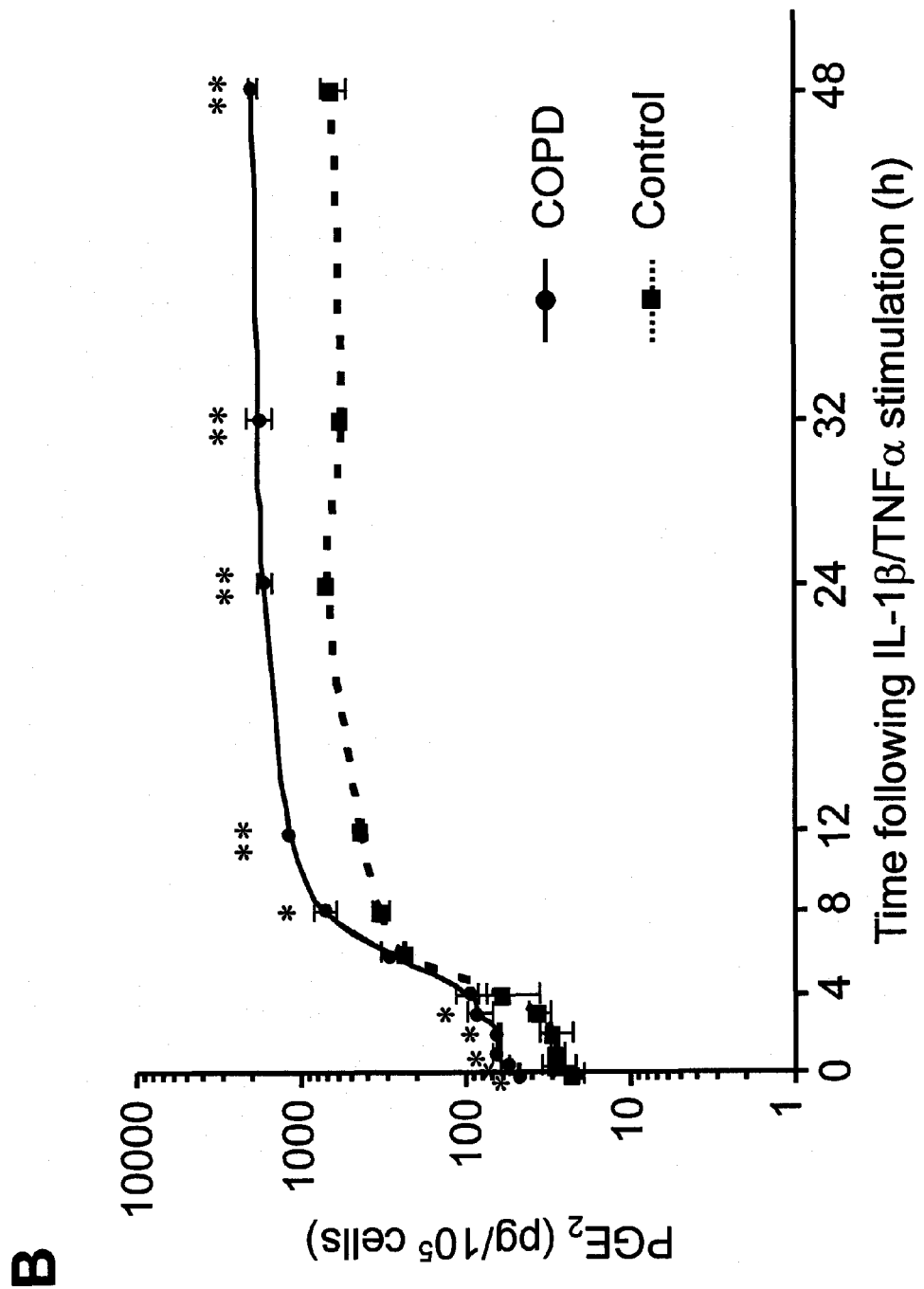

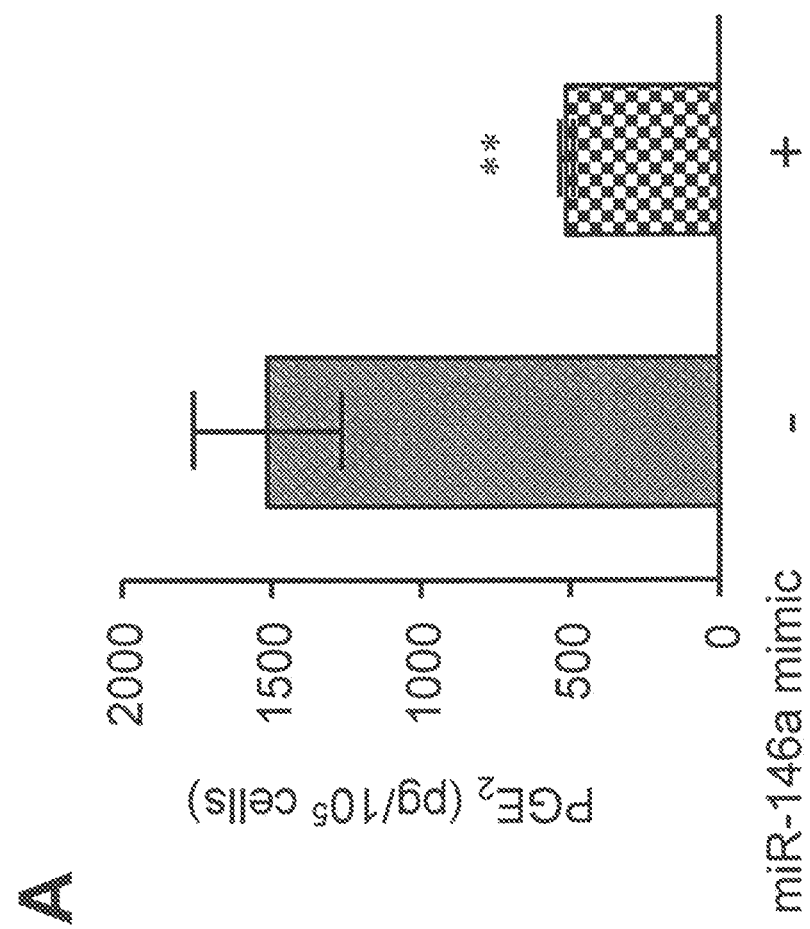

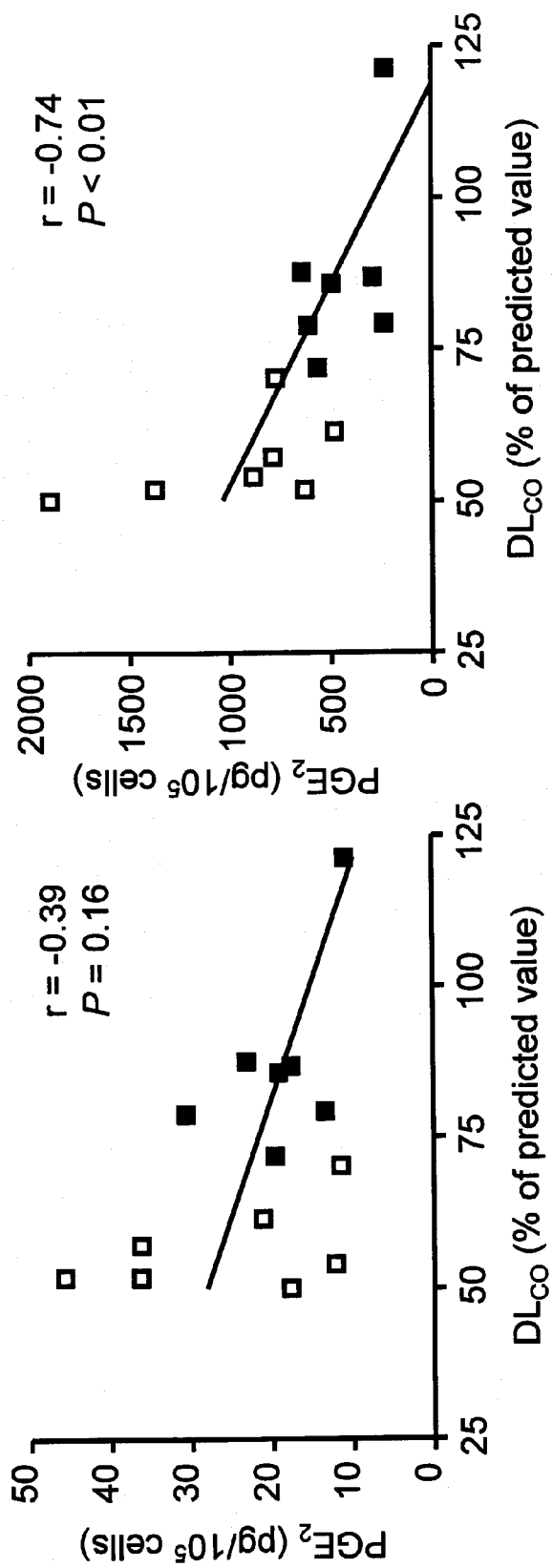

miR-146a targets Smad2, 3 and 4

| seed match | predicted consequential pairing of target region (top) and miRNA (bottom) | |
|---|---|---|
| 8mer | Position 3060-3066 of SMAD2 3' UTR 5' ...AGGGGAGGCUGUGGAGUUCUCA... <br> ‖‖‖‖‖‖ <br> hsa-miR-146a 3' UUGGGUACCUUAAGUCAAGAGU | |
| 7mer-1A | Position 7324-7330 of SMAD2 3' UTR 5' ...GAACGAGUGGUAGU-GUUCUCAG... <br> ‖‖‖ ‖‖‖‖‖ <br> hsa-miR-146a 3' UUGGGUACCUUAAGUCAAGAGU | |
| 7mer-1A | Position 812-818 of SMAD3 3' UTR 5' ...CGAAUGACGGUAAGUGUUCUCAU... <br> ‖‖‖‖‖‖ <br> hsa-miR-146a 3' UUGGGUACCUUAAGUCAAGAGU | |
| 8mer | Position 990-996 of SMAD4 3' UTR 5' ...UUUUAAGGCAGGAAGUUCUCA... <br> ‖‖‖‖‖‖‖ <br> hsa-miR-146a 3' UUGGGUACCUUAAGUCAAGAGU | |

Fig. 12

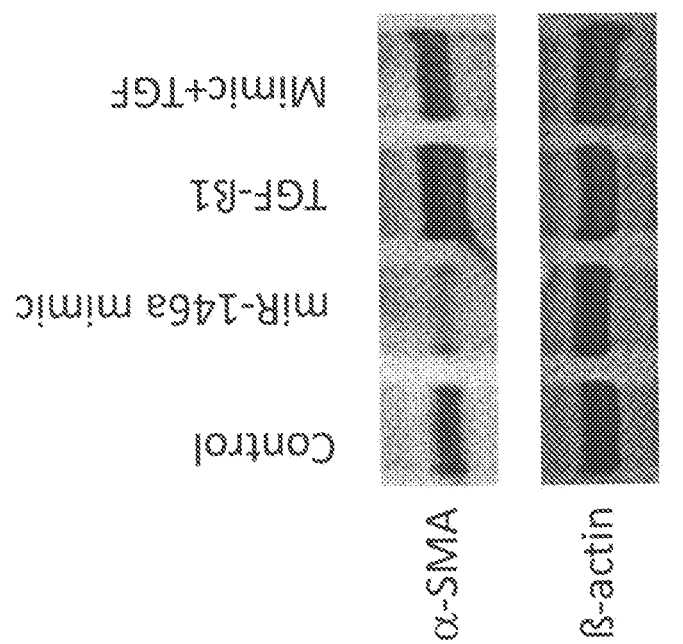

COMPOSITIONS AND METHODS FOR THE DIAGNOSIS AND TREATMENT OF INFLAMMATORY DISORDERS AND FIBROTIC DISEASE

This application is a §371 application of PCT/US2010/039783 filed Jun. 24, 2010, which claims priority to U.S. Provisional Application Nos. 61/219,913 and 61/279,310 filed Jun. 24, 2009 and Dec. 23, 2009, respectively, the entire contents of each being incorporated by reference herein.

FIELD OF THE INVENTION

This invention relates to the fields of pulmonary diseases and inflammation. More specifically, the invention provides compositions and methods for the diagnosis and treatment of inflammatory diseases and disorders related to aberrant prostaglandin production, and more particularly, pulmonary diseases such as COPD, via the manipulation of microRNA levels.

BACKGROUND OF THE INVENTION

Several publications and patent documents are cited throughout the specification in order to describe the state of the art to which this invention pertains. Each of these citations is incorporated by reference herein as though set forth in full.

Chronic obstructive pulmonary disease (COPD), currently the fourth leading cause of death in the United States, is the only major leading cause of death that is increasing (1). Cigarette smoking is the most important cause and smoking cessation, early in the course of the disease, can slow the rate at which lung function is lost (2). While current therapies can help mitigate symptoms to some extent, no currently available medical therapy can restore lung function. Because of the relentless progression of the disease that occurs despite currently available therapies, COPD mortality will rise for the next several decades among those who previously smoked, even if cigarette smoking were to be eliminated from the population (3).

An abnormal inflammatory response of the lung, which persists despite cessation of smoking (4-7), is characteristic of COPD and inflammation is believed to play a major role in COPD pathogenesis (1, 8). The tissue alterations that underlie COPD result not only from tissue damage, but also from the inability of repair responses to restore tissue structure (1, 8, 9). In this context, cigarette smoke can directly inhibit repair processes (10-13). Inflammatory mediators can also modulate repair responses. Prostaglandin (PG) $E_2$ is an inflammatory mediator that is increased in the lungs of COPD patients and is over-produced by COPD fibroblasts (14, 15). $PGE_2$ is not only a biomarker for the inflammatory process in COPD, but also inhibits repair functions mediated by lung fibroblasts (16-20). When cultured ex-vivo, fibroblasts from COPD patients are deficient in a number of repair functions due, in part, to the over-production of $PGE_2$.

$PGE_2$, which is the major eicosanoid produced by fibroblasts, is released at low levels during basal conditions, but is released at much higher levels in response to a variety of stimuli including inflammatory mediators such as interleukin (IL)-1β and tumor necrosis factor (TNF)-α that are believed to play roles in COPD. Thus, a clear need exists to determine the mechanisms driving $PGE_2$ production by COPD in response to these inflammatory mediators, thereby providing new therapeutic strategies for the treatment of COPD and other pulmonary disorders.

SUMMARY OF THE INVENTION

In accordance with the present invention, a method for reducing protein production from a COX-2 mRNA molecule in a lung fibroblast is provided. An exemplary method entails administering an effective amount of miR-146a or a mimic of miR-146a to said fibroblast, the miR-146a or mimic hybridizing to a 3' end of said COX-2 mRNA, thereby inhibiting COX-2 protein production from said mRNA. In a preferred embodiment, the COX-2 mRNA is degraded. The miRNA-146a so administered may be the naturally occurring miRNA or it may be an analogue of miRNA-146a which has been modified to increase the stability thereof in the cellular milieu. In an alternative aspect the miRNA is encoded by an expression vector and may be delivered to the target cell in a liposome or microvessicle. The present inventors have shown that the degradation of COX-2 mRNA is correlated with decreased $PGE_2$ production and increased fibroblast repair function. In a preferred embodiment, the lung fibroblast is present in a patient having chronic obstructive pulmonary disorder (COPD) and the miRNA reduces the symptoms of this disorder. The method may further entail assessing the patient so treated for an alleviation of COPD symptoms.

In one aspect of the foregoing method, the miR-146a or mimic is present in an aerosolized formulation for administration via inhalation and may optionally be encapsulated in a liposome or microvessicle. The method may also comprise administration of at least one anti-inflammatory agent.

In an yet another embodiment, delivery of miR-146a or mimic results in reduced protein production encoded by at least one other mRNA selected from the group consisting of Smad2, Smad3, Smad4, Cox-1, cPLA2 and mPGES1.

The method may also comprise administration of at least one additional miRNA, or mimic thereof, selected from the group consisting of miR-122, miR-143, miR-144, miR-101, miR-16, miR-26, miR-138, and miR-24. In a preferred embodiment miR-144 or mimic is co-administered with miR-146a.

The invention also provides a method for identifying an agent capable of modulating COX-2 mRNA stability. An exemplary method entails providing a cell comprising, i) COX-2 mRNA, and ii) miR-146a or a mimic. The cell is incubated in the presence or absence of a test agent and COX-2 mRNA levels are measured wherein a difference in the level of COX-2 mRNA in the presence of the test agent as compared to the absence of the test agent is indicative of an agent capable of modulating COX-2 mRNA stability. In one aspect, the agent disrupts COX-2 mRNA-miR-146a or mimic complex formation.

Also provided is a method for the treatment of fibrotic disease in a patient in need thereof, comprising administering an effective amount of at least one one miRNA, or mimic thereof, selected from the group consisting of miR-335, miR-140-3p, miR-886-5p, miR-146a, miR-138, miR-195, miR-Plus-A1087, miR-100, miR146b—5p, miR-214, miR-199a-3p/miR-199b-3p, let-71, miR193a-3p, and miR-365, the miRNAs or mimics thereof, being effective to decrease fibrosis in and increase cellular repair in target cells. Fibrotic diseases to be treated in accordance with the present invention, include, without limitation, COPD, emphysema, idiopathic pulmonary fibrosis, nephrogenic fibrosis, endometrial fibrosis, perineural fibrosis, hepatic fibrosis, cystic fibrosis, myocardial fibrosis, and acute lung injury.

In yet another embodiment of the invention, a method for identifying a subject having a propensity for developing COPD is provided. An exemplary method entails detecting a decrease in an amount of miR-146a in a biological sample from said subject relative to a control subject not having COPD, whereby detection of the decrease in the amount of said miRNA-146a indicates said subject is likely to develop COPD.

The invention also provides a method for increasing COX-2 mRNA stability in a lung fibroblast via administration of an effective amount of a miR-146a inhibitor to the fibroblast. In this aspect, the miR-146a inhibitor is complementary to at least a portion of miR-146a, whereby said miR-146a inhibitor inhibits miR-146a hybridizing to said COX-2 mRNA, thereby increasing COX-2 mRNA stability.

Also disclosed is a method for decreasing sPLA2 protein production in a target cell for the treatment of fibrotic disease comprising administering an effective amount of at least one miRNA selected from the group consisting of miR-335, miR-886-5p, miR-138, miR-214, let-71 and miR-365 or mimic thereof to said cell, said at least one miRNA or mimic hybridizing to a 3' end of sPLA2 mRNA, thereby reducing sPLA2 protein production and inhibiting the fibrotic response in said cell.

In yet another aspect, a method for decreasing COX-1 protein production in a target cell for the treatment of fibrotic disease is provided. An exemplary method comprises administering an effective amount of at least one miRNA selected from the group consisting of miR-335, miR-886-5p, miR-146a, miR-146b-5p, and miR-365 or mimic thereof to said cell, said at least one miRNA or mimic hybridizing to a 3' end of COX-1 mRNA, thereby reducing COX-1 protein production and inhibiting the fibrotic response in said cell.

A method for decreasing cPLA2 protein production in a target cell for the treatment of fibrotic disease is also disclosed. This method entails administering an effective amount of at least one miRNA selected from the group consisting of miR-146a, miR-146b-5p, miR-199a-3p and miR-365 or mimic thereof to said cell, said at least one miRNA or mimic hybridizing to a 3' end of cPLA2 mRNA, thereby reducing cPLA1 protein production and inhibiting the fibrotic response in said cell.

The invention also encompasses a method for reducing mPGES1 protein production in a target cell for the treatment of fibrotic disease. An exemplary method comprises administering an effective amount of at least one miRNA selected from the group consisting of miR-146a, miR-146b-5p, and miR-365 or mimic thereof to said cell, said at least one miRNA or mimic hybridizing to a 3' end of mpGES1 mRNA, thereby reducing mPGES1 protein production and inhibiting the fibrotic response in said cell.

A method for reducing mPGES2 protein production in a target cell for the treatment of fibrotic disease is also within the scope of the invention. Such method comprises administering an effective amount of at least one miRNA selected from the group consisting of miR-138, and miR-365 or mimic thereof to said cell, said at least one miRNA or mimic hybridizing to a 3' end of mPGES2 mRNA, thereby reducing mPGES2 protein production and inhibiting the fibrotic response in said cell.

In a preferred embodiment, each of the foregoing methods results in an alteration in prostaglandin production in said cell, thereby alleviating the symptoms of fibrotic disease. Fibrotic disorders to be so treated include for example, COPD, emphysema, idiopathic pulmonary fibrosis, nephrogenic fibrosis, endometrial fibrosis, perineural fibrosis, hepatic fibrosis, cystic fibrosis, myocardial fibrosis, and acute lung injury.

In a final embodiment, a method for reducing protein production of Smad2, Smad3 and/or Smad 4 in a target cell for the treatment of fibrotic disease is disclosed. An exemplary method entails administering an effective amount of miR-146a or mimic thereof to said cell, said miRNA or mimic hybridizing to a 3' end of said Smad3 and/or Smad4 mRNA, thereby reducing Smad2, Smad3 or Smad4 protein production and inhibiting the fibrotic response in said cell.

BRIEF DESCRIPTION OF THE DRAWINGS

FIG. 12. Alignments of the miR-146a sequence with the sequences for the targets Smad2, 3, and 4 as searched at "www.targetscan.org". Sequences are as follows: hsa-miR-146a (SEQ ID NO: 2), position 3060-3066 of SMAD2 3' (SEQ ID NO: 3), position 7324-7330 of SMAD2 3' (SEQ ID NO: 4), position 812-818 of SMAD3 3' (SEQ ID NO: 5), position 390-396 of SMAD4 3' (SEQ ID NO: 6).

FIG. 13A vertical axis: gel size expressed as percent of initial size (%); horizontal axis: HFL-1 cells transfected with either a control-siRNA or specific siRNA targeting Smad2 or Smad3; open bar: gels contracted in serum free DMEM (SF-DMEM); closed bar: gels contracted in the presence of TGF-β1 (100 pM). FIG. 13B vertical axis: VEGF release expressed as pg per $10^5$ cells; horizontal axis: cells transfected with siRNA; open bar: cells cultured in serum DMEM (SF-DMEM); closed bar: cells were stimulated with TGF-β1 (100 pM).

FIG. 16. An immunoblot showing the protein levels of α-smooth muscle actin (α-SMA) and β-actin in untreated HFL-1 cells (control), cells treated with miR-146a mimic, cells stimulated with TGF-β1 in the absence or presence of miR-146a mimic.

DETAILED DESCRIPTION OF THE INVENTION

Figure 1:
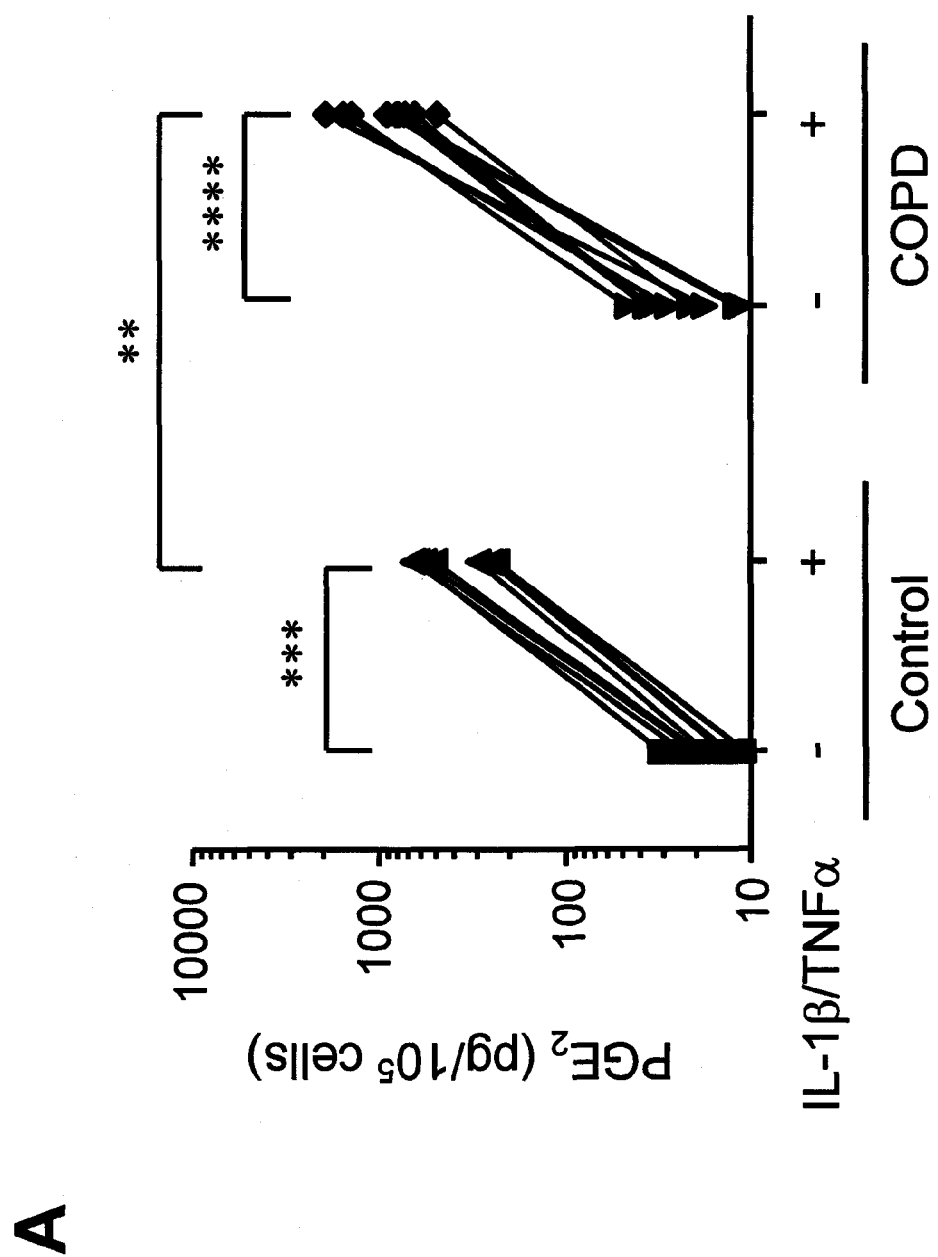
FIG. 1. Effect of IL-1β/TNF-α on $PGE_2$ production and COX-2 expression by COPD and control fibroblasts. (A) $PGE_2$ production by COPD and control fibroblasts in 24 hours. Each dot represents a separate subject and the line connects the values for a subject with and without IL-1β/TNF-α. Note that the vertical axis which shows $PGE_2$ production is a log scale. (B) Representative western blots for COX-1 and COX-2. (C) COX enzyme activity following IL-1β/TNF-α stimulation. $+P<0.05$ and $++P<0.001$, compared with control group. (D) Effect of COX-1 inhibitor (SC-560) or COX-2 inhibitor (NS-398) on IL-1β/TNF-α induced $PGE_2$ production. (E) Effect of COX silencing on IL-1β/TNF-α induced $PGE_2$ production. (F) IL-1β/TNF-α induction of COX-2 mRNA level, time course. COX-2 mRNA level was normalized to the amount of rRNA and expressed as fold change to the time 0 level of control fibroblasts. Note the vertical axis is a log scale. (G) Stability of COX-2 mRNA. COX-2 mRNA level normalized to the amount of rRNA and expressed as a percentage of mRNA level at the time of adding actinomycin D. * $P<0.05$,  $P<0.01$, * $P<0.001$, **** $P<0.0001$.
Figure 1:
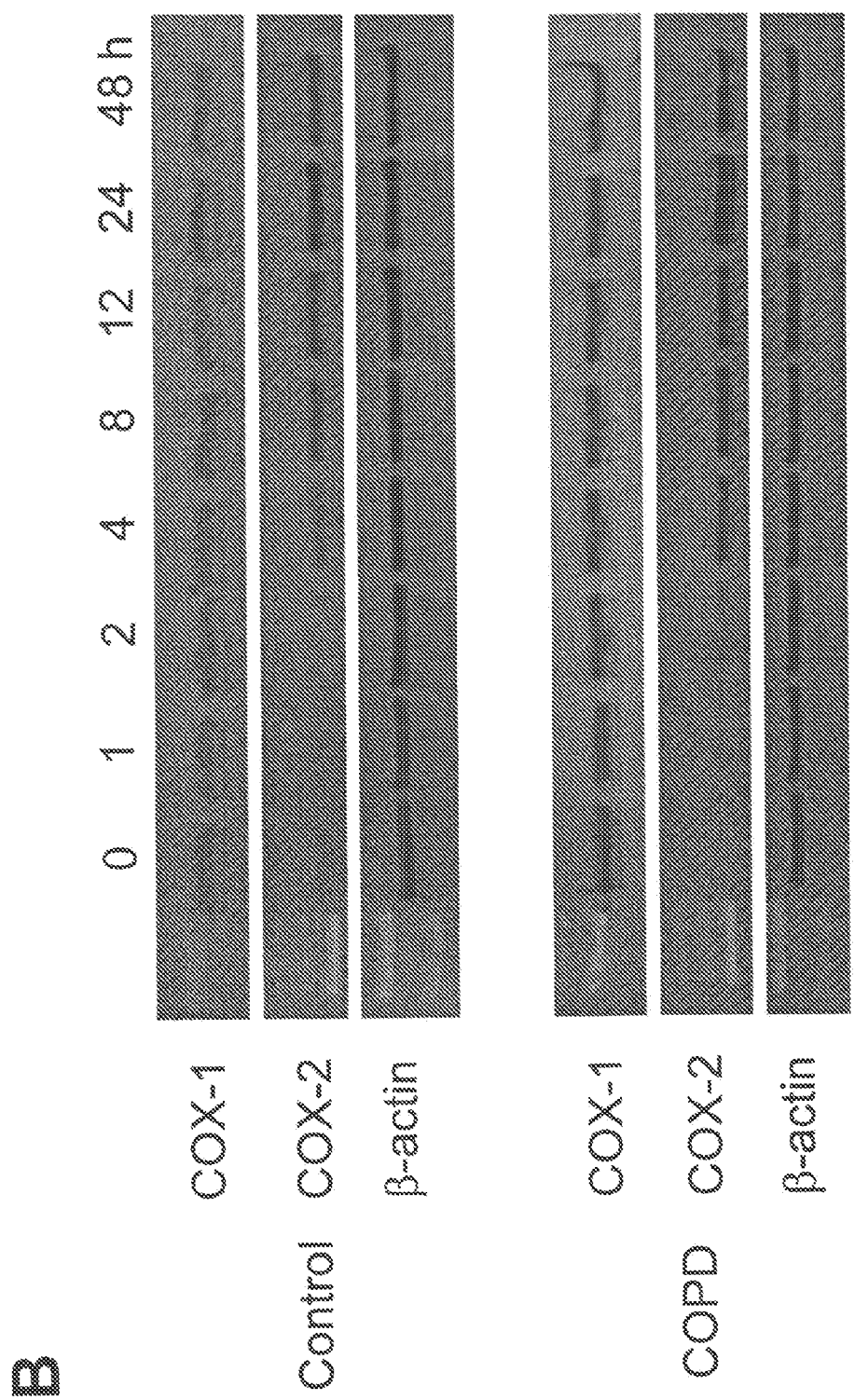
Figure 1:
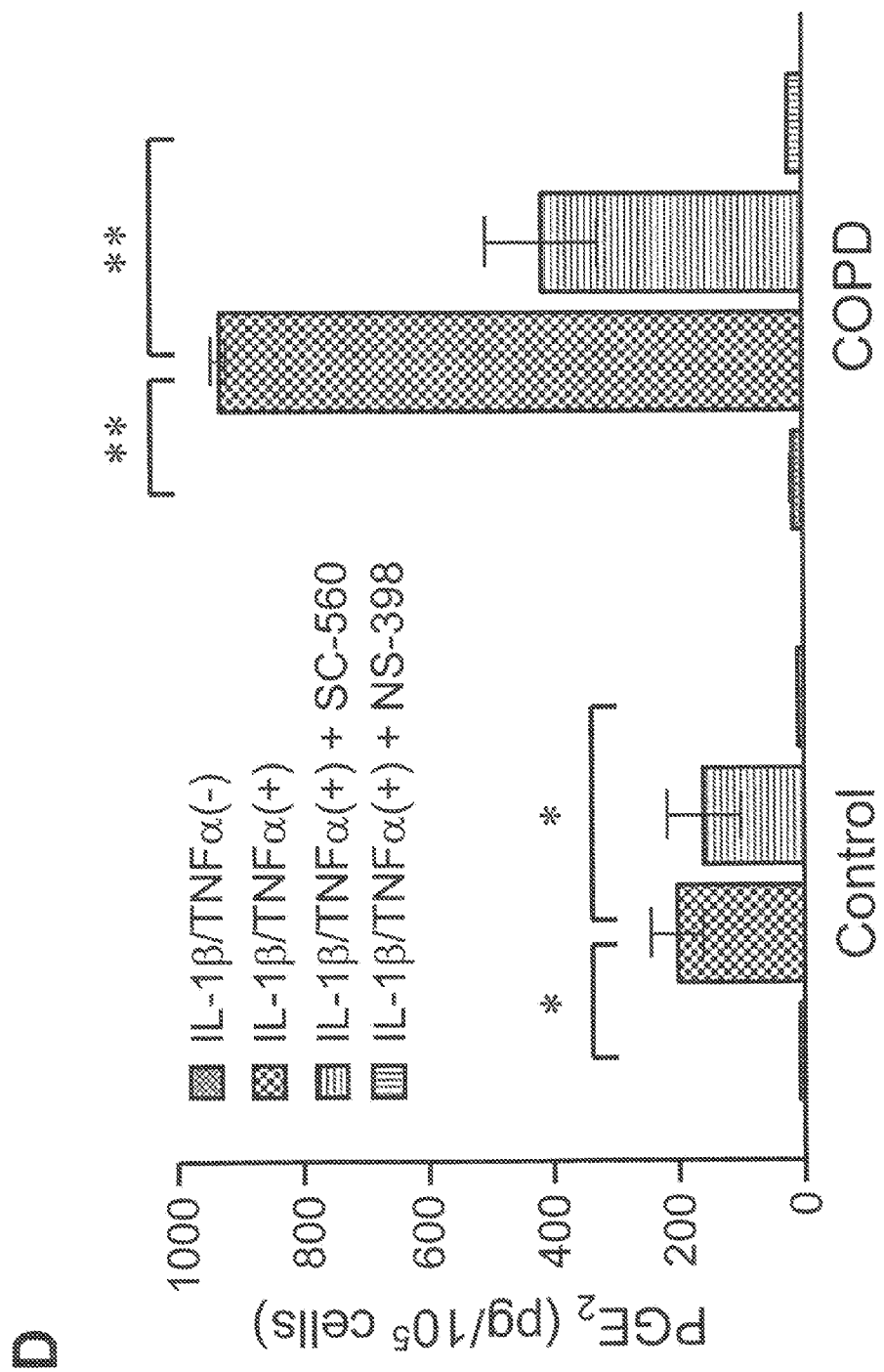
Figure 1:
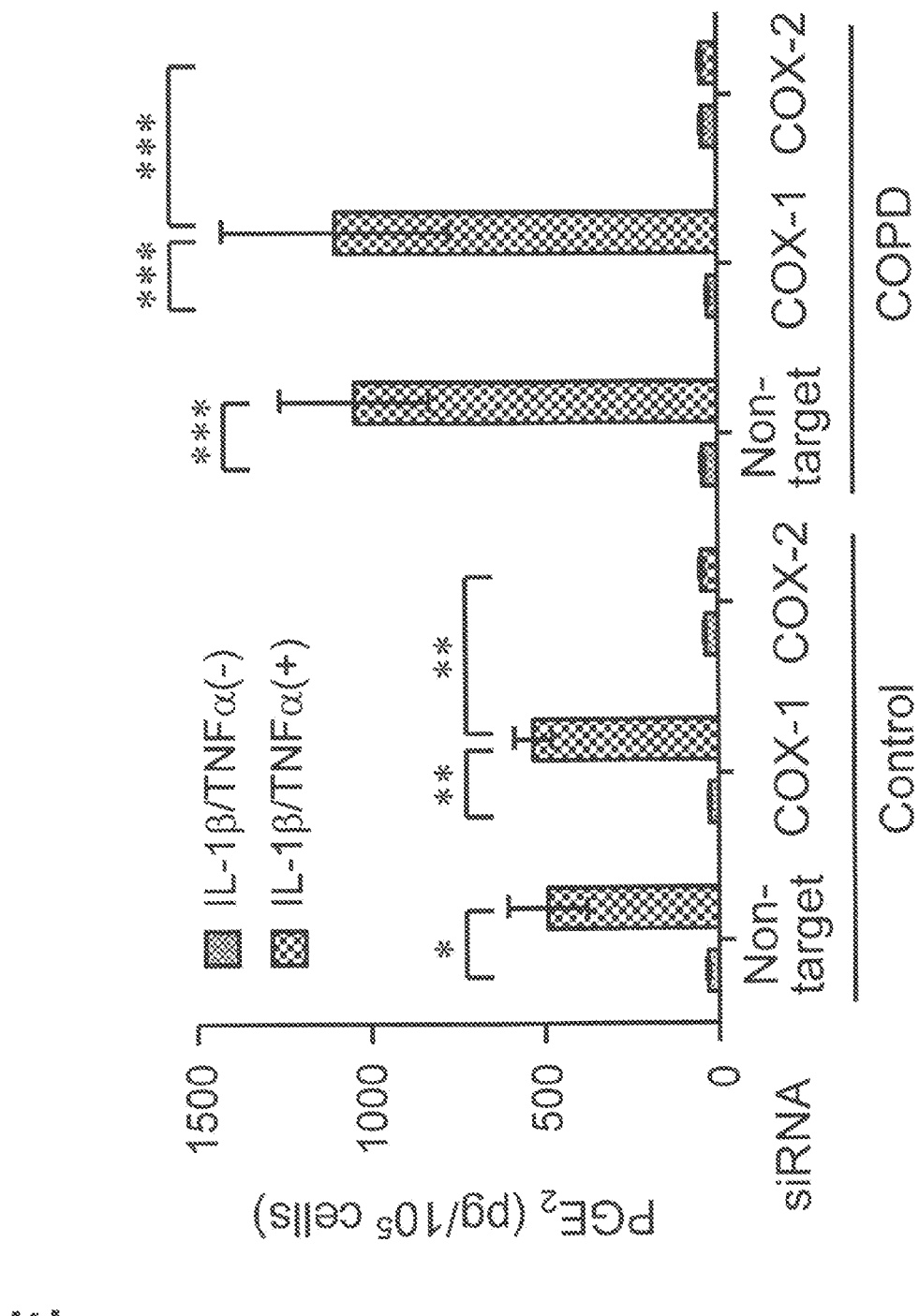
Figure 1:
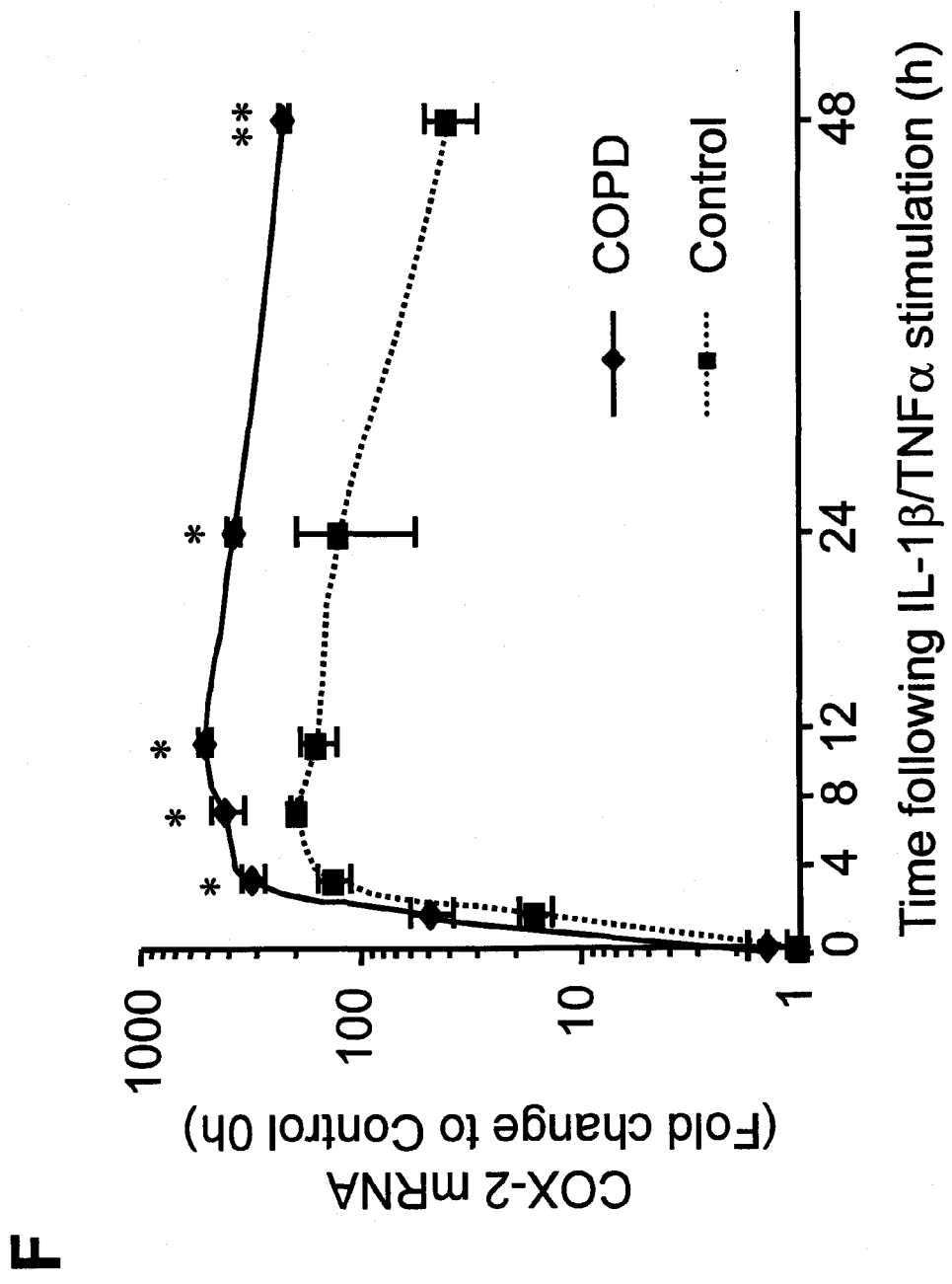
Figure 1:
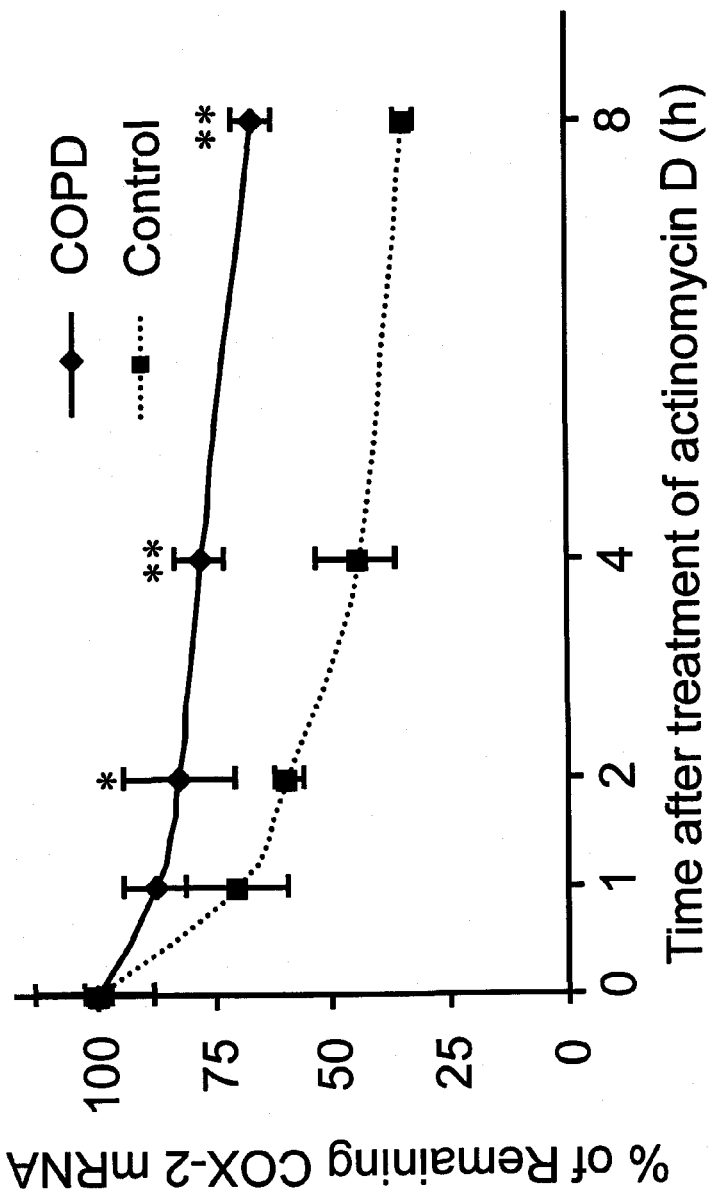

Persistent inflammation plays a major role in COPD pathogenesis, but its mechanisms are undefined. Over-production of the inflammatory mediator $PGE_2$ by COPD fibroblasts contributes to reduced repair function in these cells. The present study demonstrates that following stimulation with IL-1β/TNF-α, COPD fibroblasts produce more $PGE_2$ than do control fibroblasts, which depends on over-induction of COX-2. IL-1β/TNF-α also induced microRNA-146a expression in both cell types, but less in COPD fibroblasts. MicroRNA-146a induces degradation of COX-2 mRNA, and COX-2 mRNA is prolonged in COPD fibroblasts. Finally, the levels of microRNA-146a in cultured fibroblasts were correlated with clinical severity. MicroRNA-146a appears to play a pathogenetic role in the abnormal inflammatory response in COPD. Increasing the half-life of mRNAs of inflammatory cytokines and mediators is one mechanism for persistence of inflammation in COPD. Similarly, increasing the translation of those messages into protein would have a similar effect in leading to increased inflammation.

DEFINITIONS

The phrase "chronic obstructive pulmonary disease or COPD" refers to chronic bronchitis and emphysema, a pair of two commonly co-existing diseases of the lungs in which the airways become narrowed or collapse. This leads to a limitation of the flow of air to and from the lungs causing shortness of breath. In contrast to asthma, the limitation of airflow is rarely reversible and usually gets progressively worse over time.

The phrase "fibroblast repair function" refers to any of a number of detectable repair related functions conferring phenotypic changes in fibroblasts. In the case of lung fibroblasts cultured from patients with COPD or emphysema, evident alterations indicative of the cellular repair abnormalities include for example, slow growth, increased sensitivity to smoke, and failure to express elastin mRNA or HGF or KGF growth factors when stimulated. Notably, these differences persist with passage in culture.

The phrase "aberrant fibrosis" refers to the formation of excessive fibrous tissue, as in a reparative or reactive process. While the treatment of pulmonary fibrosis and COPD is exemplified herein, other forms of fibrosis may also be treated with the miR compositions identified by the present inventors. Such types of fibrosis include, without limitation, nephrogenic fibrosis, endometrial fibrosis, perineural fibrosis, hepatic fibrosis, cystic fibrosis, and myocardial fibrosis.

"MicroRNAs or miRNAs" refers to a family of small approximately twenty two nucleotide noncoding RNAs. They are transcribed from specific genes and generally undergo two cleavage steps that result in mature miRNAs. mRNAs cause post-transcriptional gene repression by increasing mRNA degradation or by inhibiting translation.

As used herein, the term "miR-specific inhibitor" refers to a nucleic acid molecule that is complementary, or essentially complementary to at least a portion of a microRNA molecule and inhibits its binding or activity towards its target gene transcripts. A miR-specific inhibitor may interact with the miRNA directly or may interact with the miRNA binding site in a target transcript, preventing its interaction with a miRNA. In some embodiments, the miR-specific inhibitor comprises a nucleotide sequence of at least 5 consecutive nucleotides, at least 6 consecutive nucleotides, at least 7 consecutive nucleotides, at least 8 consecutive nucleotides, or at least 9 nucleotides that are complementary to the seed region of a microRNA molecule (i.e. within positions 1 to 10 of the 5' end of the microRNA molecule). In a particular embodiment, the miR-specific inhibitor may comprise a nucleotide sequence of at least 6 consecutive nucleotides that are complementary to the seed region of a microRNA molecule at positions 2-8. These consecutive nucleotides complementary to the microRNA seed region may also be referred to as microRNA binding sites.

A miR-specific inhibitor may be a single stranded molecule. The miR-specific inhibitor may be chemically synthesized or may be encoded by a plasmid. In some embodiments, the miR-specific inhibitor comprises RNA. In other embodiments, the miR-specific inhibitor comprises DNA. In other embodiments, the miR-specific inhibitor may encompass chemically modified nucleotides and non-nucleotides. See, e.g. Brennecke et al., 2005, PLOS Biol. 3(3): pe85.

In some embodiments, a miR-specific inhibitor may be an anti-miRNA (anti-miR) oligonucleotide (see WO2005054494; Hutvagner et al., 2004, PLoS Biol. 2:E98; Orom et al., 2006, Gene 372:137-141). Anti-miR5 may be single stranded molecules. Anti-miR5 may comprise RNA or DNA or have non-nucleotide components. Alternative embodiments of anti-miR5 may be as described above for miR-specific inhibitors. Anti-miR5 anneal with and block mature microRNAs through extensive sequence complementarity. In some embodiments, an anti-miR may comprise a nucleotide sequence that is a perfect complement of the entire miRNA. In some embodiments, an anti-miR comprises a nucleotide sequence of at least 6 consecutive nucleotides that are complementary to a microRNA molecule at positions 2-8 and has at least 50%, 60%, 70%, 80%, or 90% complementarity to the rest of the miRNA. In other embodiments, the anti-miR may comprise additional flanking sequence, complimentary to adjacent primary (pri-miRNA) sequences. Chemical modifications, such as 2'-O-methyl; LNA; and 2'-O-methyl, phosphorothioate, cholesterol (antagomir); 2'-O-methoxyethyl have been described for anti-miR5 (WO2005054494; Hutvagner et al., 2004, PLoS Biol. 2:e98; Meister et al., 2004, RNA 10:544-50; Orom et al., 2006, Gene 372:137-41; WO2005079397; Krutzfeldt et al., 2005, Nature 438:685-689; Davis et al., 2006; Nucleic Acid Res. 34:2294-2304; Esau et al., 2006, Cell Metab. 3:87-98). Chemically modified anti-miR5 are commercially available from a variety of sources, including but not limited to Sigma-Proligo, Ambion, Exiqon, and Dharmacon.

"miRNA mimics" are chemically synthesized nucleic acid based molecules, preferably double-stranded RNAs which mimic mature endogenous miRNAs after transfection into cells.

Throughout this application the term "fibroblast" is used as an inclusive term describing interstitial mesenchymal cells. As a category this includes fibroblasts, myofibroblasts and the precursor/stem cells that give rise to these cells. These cells are operationally obtained by ex vivo culture of tissue specimens, generally in the presence of serum. They are characterized by a spindle shape, by the production of extracellular matrix and by the expression of cytoskeletal elements including vimentin. These features are, however, variably present and, as a group, these cells are also characterized by absence of features characteristic of epithelial cells, endothelial cells or other cell types. In tissues in vivo, similar features are used to characterize these cells. While some features, such as alpha-smooth muscle actin, can be used to distinguish between myofibroblasts, this is not a uniform feature.

The term "genetic alteration" refers to a change from the wild-type or reference sequence of one or more nucleic acid molecules. Genetic alterations include without limitation, base pair substitutions, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to a miRNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^{-6}$-fold purification of the native message. Thus, purification of at least one order of magnitude, preferably two or three orders, and more preferably four or five orders of magnitude is expressly contemplated.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligoribonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., *Molecular Cloning*, Cold Spring Harbor Laboratory (1989):

$$T_m = 81.5° C. + 16.6 \text{ Log } [Na+] + 0.41(\% \, G+C) - 0.63(\% \text{ formamide}) - 600/\#bp \text{ in duplex}$$

As an illustration of the above formula, using $[Na+] = [0.368]$ and 50% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated $T_m$ of the hybrid. Wash conditions should be as stringent as possible for the degree of identity of the probe for the target. In general, wash conditions are selected to be approximately 12-20° C. below the $T_m$ of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1× SSC and 0.5% SDS at 65° C. for 15 minutes.

The term "oligonucleotide," as used herein is defined as a nucleic acid molecule comprised of two or more ribo- or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length. Typical miRNAs are approximately 22 ribonucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the nucleic acid molecule of interest such that the latter is transcribed into mRNA. Host cell machinery then translates mRNA into a polypeptide.

Those skilled in the art will recognize that a nucleic acid vector can contain nucleic acid elements other than the promoter element and the nucleic acid molecule of interest. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, polyA addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably between 20 and 30 nucleotides and most preferably 22 nucleotides long.

"Sample" or "patient sample" or "biological sample" generally refers to a sample which may be tested for a particular molecule. Samples may include but are not limited to cells, body fluids, including bronchoaveolar lavage, blood, serum, plasma, urine, saliva, sputum, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include miRNA, shRNA, antisense oligonucleotides, peptides, peptide/DNA complexes, and any nucleic acid based molecule which exhibits the capacity to modulate the activity of the target nucleic acids described herein or their encoded proteins. Agents are evaluated for potential biological activity by inclusion in screening assays described hereinbelow.

Methods for Diagnosing a Propensity for the Development of a Fibrotic Disorder, Such as COPD The discovery that certain microRNA molecules are differentially expressed following stimulation of cells with inflammatory molecules associated with the development of fibrosis provides the means to diagnose or detect a propensity for developing such a disorder. For example, miR-146a expression levels affect COX-2 mRNA stability and $PGE_2$ production levels thereby enabling the use of this molecule for a variety of purposes in accordance with the present invention. Levels of expression of miRNA-146a and/or the other differentially expressed miRNAs provided in Table 3 can be assessed in biological samples of interest. Assays for detecting miRNA expression levels may be conducted on any type of biological sample, including but not limited to body fluids (including bronchoaveolar lavage, sputum, blood, urine, serum, gastric lavage), any type of cell (such as brain cells, lung cells, white blood cells, mononuclear cells) or body tissue.

In most embodiments for screening for COPD modulating miRNAs, the miRNA will be identified using new detection technologies which enable analysis of small samples containing 1 µg of total RNA or less. For example, ABI Taqman provides a kit and method employing 10 ng of total RNA for miRNA reverse transcription. Using Resonance Light Scattering (RLS) technology, as opposed to traditional fluorescence techniques, multiple reads can detect low quantities of RNAs using biotin labeled hybridized targets and anti-biotin antibodies. Another alternative to PCR amplification involves planar wave guide technology (PWG) to increase signal-to-noise ratios and reduce background interference. Both techniques are commercially available from Qiagen Inc. (USA).

Thus any of the aforementioned techniques may be used to detect or quantify fibrosis associated miRNA marker expression and accordingly, diagnose a propensity for developing a fibrotic disorder such as COPD.

Kits and Articles of Manufacture

Any of the aforementioned products can be incorporated into a kit which may contain a positive control miRNA or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

Methods of using miRNA modulation of $PGE_2$ production for Development of Therapeutic Agents The present inventors have discovered that several miRNA molecules are differentially expressed in fibrotic airway tissues. Notably, these miRNA molecules exhibit homology to a variety of proteins involved in the modulation and control of prostaglandin E production and thus can be used to advantage as therapeutics to inhibit or reduce the aberrant fibrosis observed in a variety of different medical disorders. The data presented herein reveal that miR-146a expression levels affect COX-2 mRNA stability and Prostaglandin $E_2$ ($PGE_2$) production levels thereby providing the means to develop methods for identifying agents that modulate the activity of the various macromolecules that modulate inflammation in fibrotic tissues, particularly the fibrotic airway. Such agents will have utility for the treatment of a variety of disorders including pulmonary disorders, such as COPD.

$PGE_2$ is an abundant eicosanoid and very potent lipid mediator, produced predominantly from arachidonic acid by tightly regulated phospholipases, cyclooxygenases (COX) and prostaglandin E synthases (PGES). Secreted $PGE_2$ acts in an autocrine or paracrine manner through its four cognate G protein coupled receptors EP1, EP2, EP3 and EP4. Action through other receptors including cytoplasmic receptors has also been described. Under physiological conditions, $PGE_2$ is key in many biological functions, such as regulation of immune responses, blood pressure, gastrointestinal integrity, and fertility. While $PGE_2$ is a classic model of a proinflammatory lipid mediator, it also has anti-inflammatory effects that are both potent and context dependent. Deregulated $PGE_2$ synthesis or degradation is associated with pathological conditions such as pulmonary inflammatory disorders, including COPD, emphysema, idiopathic pulmonary fibrosis, nephrogenic fibrosis, endometrial fibrosis, perineural fibrosis, hepatic fibrosis, cystic fibrosis, myocardial fibrosis, acute lung injury, and asthma; chronic inflammation, including psoriasis and rheumatoid arthritis; allergic inflammatory diseases, including asthma and allergic rhinitis; inflammatory bowel disease; hypertension; cardiovascular disease; periodontitis; neurological diseases, including Alzheimer's disease, Parkinson's disease, amyotrophic lateral sclerosis, and ischemic stroke; cancer and tumorigenesis, including colorectal cancer.

Thus, the present invention also provides methods for identifying agents that modulate the activity of the various components that modulate inflammation in a variety of diseases and disorders related to $PGE_2$ production including pulmonary inflammatory disorders, such as COPD, emphysema, idiopathic pulmonary fibrosis, acute lung injury, and asthma; chronic inflammation, including psoriasis and rheumatoid arthritis; allergic inflammatory diseases, including asthma and allergic rhinitis; inflammatory bowel disease; hypertension; cardiovascular disease; periodontitis; neurological diseases, including Alzheimer's disease, Parkinson's disease, amyotrophic lateral sclerosis, and ischemic stroke; cancer and tumorigenesis, including colorectal cancer.

Molecular modeling should facilitate the identification of specific organic molecules which mimic the action of miRNA-146a and the other differentially expressed miRNA disclosed herein. A combinatorial chemistry approach will be used to identify molecules with greatest activity and then iterations of these molecules will be developed for further cycles of screening. In certain embodiments, candidate drugs can be screened from large libraries of synthetic or natural compounds. One example is an FDA approved library of compounds that can be used by humans. In addition, compound libraries are commercially available from a number of companies including but not limited to Maybridge Chemical Co. (Trevillet, Cornwall, UK), Comgenex (Princeton, N.J.), Microsource (New Milford, Conn.), Aldrich (Milwaukee, Wis.), AKos Consulting and Solutions GmbH (Basel, Switzerland), Ambinter (Paris, France), Asinex (Moscow, Russia), Aurora (Graz, Austria), BioFocus DPI, Switzerland, Bionet (Camelford, UK), ChemBridge, (San Diego, Calif.), ChemDiv, (San Diego, Calif.), Chemical Block Lt, (Moscow, Russia), ChemStar (Moscow, Russia), Exclusive Chemistry, Ltd (Obninsk, Russia), Enamine (Kiev, Ukraine), Evotec (Hamburg, Germany), Indofine (Hillsborough, N.J.), Interbioscreen (Moscow, Russia), Interchim (Montlucon, France), Life Chemicals, Inc. (Orange, Conn.), Microchemistry Ltd. (Moscow, Russia), Otava, (Toronto, ON), PharmEx Ltd. (Moscow, Russia), Princeton Biomolecular (Monmouth Junction, N.J.), Scientific Exchange (Center Ossipee, N.H.), Specs (Delft, Netherlands), TimTec (Newark, Del.), Toronto Research Corp. (North York ON), UkrOrgSynthesis (Kiev, Ukraine), Vitas-M, (Moscow, Russia), Zelinsky Institute, (Moscow, Russia), and Bicoll (Shanghai, China).

Libraries of natural compounds in the form of bacterial, fungal, plant and animal extracts are commercially available or can be readily prepared by methods well known in the art. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Several commercial libraries can be used in the screens.

The agents employed in drug screening assays may either be free in solution, affixed to a solid support or within a cell. One method of drug screening utilizes eukaryotic or prokaryotic host cells which are stably transformed with recombinant polynucleotides expressing the miRNA or a mimic thereof preferably in competitive binding assays. Such cells, either in viable or fixed form, can be used for standard binding assays. One may determine, for example, formation of complexes between the miRNA and the agent being tested, or examine the degree to which the formation of a complex between the miRNA and the 3' end of COX-2 mRNA is interfered with by the agent being tested.

A further technique for drug screening involves the use of host eukaryotic cell lines or cells (such as described above) which have a nonfunctional or altered fibrosis associated miRNA molecules. These host cell lines or cells exhibit defective miRNA function. The host cell lines or cells are grown in the presence of drug compound. The level of inflammatory cytokine production and/or $PGE_2$ production of the host cells is measured to determine if the compound is capable of regulating inflammatory cytokine production and/or $PGE_2$ production in the defective cells. Host cells contemplated for use in the present invention include but are not limited to mammalian cells, particularly airway and alveolar fibroblasts. Methods for introducing nucleic acid molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the miRNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Promoters for use in expression vectors of this invention include promoters that are operable in eukaryotic cells. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and *Saccharomyces* promoters such as the gal4 inducible promoter and the PGK constitutive promoter, and the Thy-1 promoter. In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the miRNAs of the present invention provide a system in which to screen potential compounds or agents for the ability to modulate the development of fibrosis. Thus, in one embodiment, the nucleic acid molecules of the invention may be used to create recombinant cell lines for use in assays to identify agents which modulate aspects of fibroblast metabolism associated with airway thickening and decreased air flow.

In another embodiment, the identification of the differentially expressed miRNAs involvement in inflammatory processes in the lung enables the production of strains of laboratory mice which express altered levels of such miRNAs. Transgenic mice expressing these miRNA molecules provide a model system in which to examine the role of the miRNA in the development and progression towards fibrotic diseases such as COPD. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular inflammatory processes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of miRNA encoding nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated miRNA encoding genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its nonhomologous insertion with effective herpes drugs such as gancyclovir (GANC) or (1-(2-deoxy-2-fluoro-B-D arabinofluranosyl)-5-iodouracil, (FIAU). By this counter selection, the number of homologous recombinants in the surviving transformants can be increased.

As used herein, a knock-in animal is one in which the endogenous murine gene, for example, has been replaced with human miRNA encoding gene of the invention. Such knock-in animals provide an ideal model system for studying the development of COPD.

As used herein, the expression of a miRNA encoding nucleic acid can be targeted in a "tissue specific manner" or "cell type specific manner" using a vector in which nucleic acid sequences encoding the miRNA are operably linked to regulatory sequences (e.g., promoters and/or enhancers) that direct expression of the encoded miRNA in a particular tissue or cell type. Such regulatory elements may be used to advantage for both in vitro and in vivo applications. Promoters for directing tissue specific proteins are well known in the art and described herein.

The nucleic acid sequence encoding the miRNA may be operably linked to a variety of different promoter sequences for expression in transgenic animals. Such promoters include, but are not limited to a Thy-1 promoter; a PGK promoter; and a CMV promoter. Methods of use for the transgenic mice of the invention are also provided herein. Transgenic mice into which a nucleic acid encoding the miRNA has been introduced are useful, for example, to develop screening methods to identify therapeutic agents capable of modulating the development of COPD.

Pharmaceuticals and miRNA therapies

The elucidation of the role played by miRNAs on PGE production described herein facilitates the development of pharmaceutical compositions useful for treatment and diagnosis of fibrotic disorders such as COPD and emphysema and other diseases related to aberrant prostaglandin production. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g. oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

The invention includes a method of treating a fibrotic disorder such as COPD in a mammal via administration of microRNAs that can selectively increase PGE production in airway fibroblasts or selectively decrease that of alveolar fibroblasts. This approach should enable tissue remodeling locally within the lung: that is to inhibit fibrosis in the airways and to remove the inhibition of repair in the alveoli. Preferably, the mammal is a human. The term "patient" as used herein refers to a human.

Specific miRNA preparations which modulate $PGE_2$ production as well as delivery methods are provided as a novel therapy to treat fibrotic disease. miRNAs having the requisite level of complementarity with the 3' end of COX-2 mRNA for example, are effective to modulate stability of this RNA, thereby modulating downstream $PGE_2$ production. The miRNA can be delivered to a patient in vivo either systemically or locally with carriers, as discussed below. The compositions of the invention may be used alone or in combination with other agents or genes encoding proteins to augment the efficacy of the compositions. The other differentially expressed miRNA molecules provided in Table 3 likewise exhibit homology to molecules which play a role in the inflammatory response. These include, for example sPLA2, Cox1, mPGES1, cPLA2. Accordingly, use of these other miRNA should have efficacy for modulating the aberrant fibrosis associated with the medical disorders described herein.

A "membrane permeant peptide sequence" refers to a peptide sequence which is able to facilitate penetration and entry of the miRNA across the cell membrane. Exemplary peptides include without limitation, the signal sequence from Kaposi fibroblast growth factor, the HIV tat peptide (Vives et al., J. Biol. Chem., 272:16010-16017, 1997), Nontoxic membrane translocation peptide from protamine (Park et al., FASEB J. 19(11):1555-7, 2005), CHARIOT® delivery reagent (Active Motif; U.S. Pat. No. 6,841,535) and the antimicrobial peptide Buforin 2.

In one embodiment of the invention miRNAs are delivered for therapeutic benefit. There are several ways to administer the miRNA of the invention in vivo to treat pulmonary disorders such as COPD and emphysema, including, but not limited to, naked miRNA delivery, miRNA conjugation and delivery, liposome carrier-mediated delivery, polymer carrier delivery, nanoparticle compositions, plasmid-based methods, and the use of viruses.

miRNA compositions of the invention can comprise a delivery vehicle, including liposomes, for administration to a subject, carriers and diluents and their salts, and/or may be present in pharmaceutically acceptable formulations. This can be necessary to allow the miRNA to cross the cell membrane and escape degradation. Methods for the delivery of nucleic acid molecules are described in Akhtar et al., 1992, Trends Cell Bio., 2, 139; Delivery Strategies for Antisense Oligonucleotide Therapeutics, ed. Akhtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192; Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule.

The frequency of administration of the miRNA to a patient will also vary depending on several factors including, but not limited to, the type and severity of the pulmonary disorder to be treated, the route of administration, the age and overall health of the individual, the nature of the miRNA, and the like. It is contemplated that the frequency of administration of the miRNA to the patient may vary from about once a month, to about once a week, to about once per day, to about several times daily.

Pharmaceutical compositions that are useful in the methods of the invention may be administered systemically in parenteral, oral solid and liquid formulations, ophthalmic, suppository, aerosol, topical or other similar formulations. In addition to the appropriate miRNA, these pharmaceutical compositions may contain pharmaceutically-acceptable carriers and other ingredients known to enhance and facilitate drug administration. Thus such compositions may optionally contain other components, such as adjuvants, e.g., aqueous suspensions of aluminum and magnesium hydroxides, and/or other pharmaceutically acceptable carriers, such as saline. Other possible formulations, such as nanoparticles, liposomes, resealed erythrocytes, and immunologically based systems may also be used to administer the appropriate miRNA to a patient according to the methods of the invention. The use of nanoparticles to deliver miRNAs, as well as cell membrane permeable peptide carriers that can be used are described in Crombez et al., Biochemical Society Transactions v35:p 44 (2007).

Methods of the invention directed to treating COPD involve the administration of miRNA-146a or mimic of miRNA-146a in a pharmaceutical composition. mRNA-146a or mimic is administered to an individual as a pharmaceutical composition comprising miRNA-146a or mimic and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters. While the use of miRNA-146a is exemplified herein, the use of one or more miRNA molecules or mimics described in Table 3 for the treatment of fibrotic disease is also within the scope of the present invention.

One skilled in the art appreciates that a pharmaceutical composition comprising the differentially expressed miRNAs or mimics thereof can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intra-tracheally (i.t.), or intra-articularly or by passive or facilitated absorption. The same routes of administration can be used other pharmaceutically useful compounds, for example, small molecules, nucleic acid molecules, peptides, antibodies and polypeptides as discussed hereinabove.

A pharmaceutical composition comprising such differentially expressed miRNAs or or mimic also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

In one aspect, the pharmaceutical preparation comprises a miRNA or mimic targeting the 3' end of COX2 mRNA or an expression vector encoding for a miRNA or mimic. Such pharmaceutical preparations can be administered to a patient for treating COPD.

Expression vectors for the expression of miRNA or mimic molecules preferably employ a strong promoter which may be constitutive or regulated. Such promoters are well known in the art and include, but are not limited to, RNA polymerase II promoters, the T7 RNA polymerase promoter, and the RNA polymerase III promoters U6 and H1 (see, e.g., Myslinski et al. (2001) Nucl. Acids Res., 29:2502 09).

Nucleic acid molecules can be administered to cells by incorporation into other vehicles, such as biodegradable polymers, hydrogels, cyclodextrins. (see for example Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722)

Cationic lipids and polymers are two classes of non-viral miRNA or mimic delivery which can form complexes with negatively charged miRNA or mimic. The self-assembly PEGylated polycation polyethylenimine (PEI) has also been used to condense and protect miRNAs (Schiffelers et al., 2004, Nuc. Acids Res. 32: 141-110). The miRNA or mimic complex can be condensed into a nanoparticle to allow efficient uptake of the miRNA or mimic through endocytosis. Also, the nucleic acid-condensing property of protamine has been combined with specific antibodies to deliver miRNAs or mimics and can be used in the invention (Song et al., 2005, Nat. Biotech. 23:709-717).

Administration of the miRNA or mimic by inhalation is a particularly preferred means of treating an individual having an inflammatory lung disease. One skilled in the art would recognize that such miRNA or mimic can be suspended or dissolved in an appropriate pharmaceutically acceptable carrier and administered, for example, directly into the lungs using a nasal spray or inhalant.

A pharmaceutical composition comprising miRNA can be administered as an aerosol formulation which contains the miRNA in dissolved, suspended or emulsified form in a propellant or a mixture of solvent and propellant. The aerosolized formulation is then administered through the respiratory system or nasal passages.

An aerosol formulation used for nasal administration is generally an aqueous solution designed to be administered to the nasal passages in drops or sprays. Nasal solutions are generally prepared to be similar to nasal secretions and are generally isotonic and slightly buffered to maintain a pH of about 5.5 to about 6.5, although pH values outside of this range can additionally be used. Antimicrobial agents or preservatives can also be included in the formulation.

An aerosol formulation used for inhalations and inhalants is designed so that the miRNA is carried into the respiratory tree of the patient administered by the nasal or oral respiratory route. Inhalation solutions can be administered, for example, by a nebulizer. Inhalations or insufflations, comprising finely powdered or liquid drugs, are delivered to the respiratory system as a pharmaceutical aerosol of a solution or suspension of the drug in a propellant.

An aerosol formulation generally contains a propellant to aid in disbursement of the miRNA. Propellants can be liquefied gases, including halocarbons, for example, fluorocarbons such as fluorinated chlorinated hydrocarbons, hydrochlorofluorocarbons, and hydrochlorocarbons as well as hydrocarbons and hydrocarbon ethers (Reminaton's Pharmaceutical Sciences 18th ed., Gennaro, A. R., ed., Mack Publishing Company, Easton, Pa. (1990)).

Halocarbon propellants useful in the invention include fluorocarbon propellants in which all hydrogens are replaced with fluorine, hydrogen-containing fluorocarbon propellants, and hydrogen-containing chlorofluorocarbon propellants. Halocarbon propellants are described in Johnson, U.S. Pat. No. 5,376,359, and Purewal et al., U.S. Pat. No. 5,776,434.

Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as numerous other ethers.

The miRNA can also be dispensed with a compressed gas. The compressed gas is generally an inert gas such as carbon dioxide, nitrous oxide or nitrogen.

An aerosol formulation of the invention can also contain more than one propellant. For example, the aerosol formulation can contain more than one propellant from the same class such as two or more fluorocarbons. An aerosol formulation can also contain more than one propellant from different classes. An aerosol formulation can contain any combination of two or more propellants from different classes, for example, a fluorohydrocarbon and a hydrocarbon.

Effective aerosol formulations can also include other components, for example, ethanol, isopropanol, propylene glycol, as well as surfactants or other components such as oils and detergents (Remington's Pharmaceutical Sciences, 1990; Purewal et al., U.S. Pat. No. 5,776,434). These aerosol components can serve to stabilize the formulation and lubricate valve components.

The aerosol formulation can be packaged under pressure and can be formulated as an aerosol using solutions, suspensions, emulsions, powders and semisolid preparations. A solution aerosol consists of a solution of an active ingredient such as a miRNA in pure propellant or as a mixture of propellant and solvent. The solvent is used to dissolve the active ingredient and/or retard the evaporation of the propellant. Solvents useful in the invention include, for example, water, ethanol and glycols. A solution aerosol contains the active ingredient miRNA and a propellant and can include any combination of solvents and preservatives or antioxidants.

An aerosol formulation can also be a dispersion or suspension. A suspension aerosol formulation will generally contain a suspension of a miRNA and a dispersing agent. Dispersing agents useful in the invention include, for example, sorbitan trioleate, oleyl alcohol, oleic acid, lecithin and corn oil. A suspension aerosol formulation can also include lubricants and other aerosol components.

An aerosol formulation can similarly be formulated as an emulsion. An emulsion can include, for example, an alcohol such as ethanol, a surfactant, water and propellant, as well as the active ingredient miRNA. The surfactant can be nonionic, anionic or cationic. One example of an emulsion can include, for example, ethanol, surfactant, water and propellant. Another example of an emulsion can include, for example, vegetable oil, glyceryl monostearate and propane.

An aerosol formulation containing a miRNA will generally have a minimum of 90% of the particles in inhalation products between about 0.5 and about 10 µm to maximize delivery and deposition of the miRNA to respiratory fluids. In particular, the particle size can be from about 3 to about 6 µm.

A pharmaceutical composition comprising a miRNA also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

In order to treat an individual having a fibrotic disease to alleviate a sign or symptom of the disease, at least one miRNA should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of a miRNA required to obtain an effective dose in a subject depends on many factors, including the particular inflammatory lung disease being treated, the age, weight and general health of the subject, as well as the route of administration and the number of treatments to be administered. In view of these factors, the skilled artisan would adjust the particular dose so as to obtain an effective dose for treating an individual having an inflammatory lung disease.

In an individual suffering from an inflammatory lung disease, in particular a more severe form of the disease, administration of a miRNA can be particularly useful when administered in combination, for example, with a conventional agent for treating such a disease or with another miRNA which modulates expression or function of a protein which plays a role in the inflammatory process. The skilled artisan would administer a miRNA, alone or in combination with a second agent or miRNA, based on the clinical signs and symptoms exhibited by the individual and would monitor the effectiveness of such treatment using routine methods such as pulmonary function determination, radiologic, immunologic or, where indicated, histopathologic methods.

A miRNA can be administered in combination with steroidal anti-inflammatory agents including corticosteroids, for example, dexamethasone, beclomethasone, fluticasone, triamcinolone and budesonide. A miRNA can also be administered in combination with non-steroidal anti-inflammatory agents such as aspirin (acetylsalicylic acid), indomethacin, ibuprofen, naproxen, diclofenac, sulindac, oxaprozin, diflunisal, bromfenac, piroxicam, etodolac and fenoprofen. A miRNA can also be administered with other immune modifiers such as inhibitors or agonists of cytokine receptors, antibodies directed against cytokines or their receptors or agents that act on immune system signal transduction pathways. When a miRNA is used with another anti-inflammatory agent, either or both of the miRNA and anti-inflammatory agent can generally be administered at a lower dosage.

When a miRNA is administered in combination with one or more other anti-inflammatory agent, the miRNA and other anti-inflammatory agent can be co-administered in the same formulation. Alternatively, the miRNA and other anti-inflammatory agent can be administered simultaneously in separate formulations.

Administration of the pharmaceutical preparation is preferably in a "prophylactically effective amount" or a "therapeutically effective amount" (as the case may be, although prophylaxis may be considered therapy), this being sufficient to show benefit to the individual. This amount prevents, alleviates, abates, or otherwise reduces the severity of symptoms in a patient. In the case of COPD or emphysema, such symptoms include, without limitation, shortness of breath, wheezing, chronic cough, excessive mucus production, chest tightness, dyspnea and cyanosis. COPD also is associated with extrapulmonary manifestations that are also thought to result from the consequences of chronic inflammation. Reduction in the extrapulmonary manifestations of COPD is also regarded as a potentially important therapeutic goal.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

The following materials and methods are provided to facilitate the practice of the present invention.

Materials

Commercially available reagents were obtained as follows: Dulbecco modified Eagle medium (DMEM), penicillin-streptomycin (Pen-Strep), fetal bovine serum (FBS), TRIzol® reagent, DNAse I, Opti-MEM and Lipofectamine 2000 were from Invitrogen Life Technologies (Carlsbad, Calif.); amphotericin B was from X-Gen Pharmaceuticals, Inc. (Northport, N.Y.); recombinant human interleukin (IL)-1β and tumor necrosis factor (TNF)-α were from R&D Systems (Minneapolis, Minn.); SC-560 and NS-398 were from Cayman Chemical (Ann Arbor, Mich.); actinomycin D was from Sigma (St. Louis, Mo.); Anti-cyclooxygenase (COX)-1 and 2 antibodies were from Santa Cruz Biotechnology (sc-1752 and 1745; Santa Cruz, Calif.); COX-1, 2 and non-targeting small interfering RNA (siRNA), and hsa-miRNA-146a Mimic, hsa-miRNA-146a Inhibitor and miRIDIAN microRNA Mimic/Inhibitor Negative Control were from Dharmacon (Lafayette, Colo.).

Clinical Features of Subjects

Primary lung fibroblasts from 9 subjects with moderate to severe chronic obstructive pulmonary disease (COPD) and 8 subjects without clinical or functional signs of COPD (control) were included in the study. The clinical features of the non-COPD and COPD subjects are presented in Table 1. All subjects were undergoing surgery for lung tumor resection. The study was approved by the Human Studies Committee of the Medical Board of the State of Schleswig-Holstein and the Ethics Committee at the Karolinska Institute where samples were collected, and all subjects provided written informed consent for the acquisition of material for research. Using the Global Initiative for Chronic Obstructive Lung Disease (GOLD) classification based on forced expiratory volume in one second ($FEV_1$), COPD subjects were classified as stage I to IV (mild to very severe COPD). All controls lacked the criteria for COPD. COPD subjects showed the expected physiological alterations including significantly lower $FEV_1$ and lower diffusion capacity for carbon monoxide ($DL_{CO}$).

TABLE 1

Clinical features of Subjects

| | Control | COPD | P value |
|---|---|---|---|
| n of subjects | 8 | 9 | |
| Age (yr) | 64.3 ± 3.4 | 60.7 ± 3.8 | 0.48 |
| Gender (M/F) | 6/2 | 7/2 | 0.96 |
| Height (cm) | 168.5 ± 3.4 | 173.3 ± 3.5 | 0.28 |
| Weight (kg) | 68.6 ± 5.6 | 71.8 ± 5.9 | 0.61 |
| Smoking (pack-years) | 40.8 ± 10.5 | 41.9 ± 6.2 | 0.61 |
| GOLD stage (I/II/III/IV) | 0/0/0/0 | 0/3/4/2 | |
| VC (% of predicted value) | 107.3 ± 4.0 | 88.6 ± 8.6 | 0.046 |
| $FEV_1$ (% of predicted value) | 97.0 ± 5.6 | 43.1 ± 6.1 | <0.0001 |
| RV/TLC (%) | 38.9 ± 2.9 | 58.1 ± 3.8 | 0.001 |
| $DL_{CO}$ (% of predicted value) | 87.5 ± 7.2 | 56.9 ± 2.9 | 0.0006 |

Cell Culture

Human lung fibroblasts were cultured as described (E1) from normal appearing areas of the pulmonary parenchyma in a region as far as possible from the tumor that was free of pleura or large airways. After isolation, cells were aliquoted, frozen, and shipped to the University of Nebraska Medical Center where all in vitro experiments were performed. The cells were cultured on 100 mm tissue culture dishes (Falcon; Becton-Dickinson Labware, Lincoln Park, N.J.) with DMEM supplemented with 10% FBS, 100 µg/ml penicillin, 250 µg/ml streptomycin sulfate, and 2.5 µg/ml amphotericin B. Cells were cultured at 37° C. in a humidified atmosphere of 5% $CO_2$ and passaged every 4 to 5 days. Thawed lung fibroblasts were used between the third and sixth subsequent passages.

Measurement of $PGE_2$

Prostaglandin (PG) $E_2$ production from lung fibroblasts was determined by enzyme immunoassay (EIA; Cayman) following the manufacturer's instructions. To evaluate $PGE_2$ production with or without IL-1β/TNF-α, cells were cultured until 90% confluence, serum-starved for 2 h and then treated, except for the concentration-response assays, with or without 2 ng/ml of each IL-1β/TNF-α in serum free (SF)-DMEM. Except for the time-course assays, supernatants were harvested 24 h later and stored at −80° C. until assayed. When used, SC-560 ($10^{-7}$M) and NS-398 ($10^{-6}$M) were added 1 h before the addition of IL-1β/TNF-α.

Western Blot Analysis

Whole cell lysates were prepared and the total protein content of each was measured using Bio-Rad Protein Assay (Bio-Rad Laboratories, Hercules, Calif.). After heating for 5 min at 95° C., 5 to 10 µg of protein was loaded and separated by electrophoresis on 10% sodium dodecylsulfate polyacrylamide gels. After transferring the proteins to a polyvinylidene diflouride membrane (Bio-Rad), the membrane was blocked with 5% milk in phosphate-buffered saline (PBS) and allowed to react with primary antibodies against COX-1 and 2 (1:200 and 1:400 dilution) at 4° C. overnight. COX-1 and 2 proteins were subsequently detected and quantified using horseradish peroxidase-conjugated IgG (Rockland, Gilbertsville, Pa.) with an enhanced chemiluminescence plus detection system (ECL plus) and Typhoon Scanner (Amersham Pharmacia Biotech, Buckinghamshire, England).

Measurement of COX Activity

Cells were cultured until confluence and then stimulated with IL-1β/TNF-α (2 ng/ml each). Whole cell lysates were prepared at various times and total COX and COX-2 activities were determined by COX Activity Assay (Cayman) following the manufacturer's instructions. This kit measures enzyme activity colorimetrically by monitoring the appearance of oxidized N,N,N',N'-tetramethyl-p-phenylenediamine at 590 nm. The reaction rate was determined by using the N,N,N',N'-tetramethyl-p-phenylenediamine extinction coefficient ($\epsilon_M$=8.26 mM$^{-1}$·cm$^{-1}$). Activities of COX-2 were differentiated using the isoform-specific inhibitors DuP-697 and SC-560 according to the manufacturer's instructions.

COX Silencing

Cells were seeded in 60 mm dishes at 3×$10^4$ cells/ml in DMEM with 10% FBS without antibiotics or amphotericin B. At 50% confluence, cells were treated with IL-1β/TNF-α (2 ng/ml each) for 24 h and then transfected with siRNAs. To prepare the transfection solution, 7.5 µl of Lipofectamine 2000 was mixed with 242.5 µl of Opti-MEM medium and incubated for 5 min at room temperature. In a separate tube, 40 pM of each siRNA was mixed with 250 µl of Opti-MEM. These two tubes were combined, gently mixed, and incubated for 20 min at room temperature. After incubation, Opti-MEM was added to obtain a final volume of 2 ml (final concentration of siRNAs=100 nM) for each dish. Cells were washed with sterile PBS twice and incubated with siRNA transfection solution for 6 h at 37° C. Cells were further cultured for 24 h, and then media were collected and assayed for $PGE_2$ by enzyme immunoassay (EIA).

RNA Preparation and Real Time RT-PCR

Total RNA was extracted using TRIzol® reagent and 1 μl of total RNA was treated with DNAse I to eliminate potential genomic DNA contamination. For complementary DNA (cDNA) synthesis, total RNA was transcribed using High-Capacity cDNA Reverse Transcription Kits (Applied Biosystems, Foster City, Calif.). Real time polymerase chain reaction (PCR) for COX-2 mRNA detection was conducted in a total volume of 20 μl using Taqman Gene Expression Assays and the ABI Prism 7500 (Applied Biosystems) following the manufacturer's instructions. For miRNA-146a quantification, TaqMan MicroRNA Reverse Transcription Kit and TaqMan MicroRNA Assays (Applied Biosystems) were used. As an internal control, the ribosomal RNA (rRNA) control kit (Applied Biosystems) was used.

Measurement of mRNA Stability

Cells were pretreated with IL-1β/TNF-α (2 ng/ml each) for 24 h and then treated with actinomycin D (2 μg/ml), a potent inhibitor of mRNA synthesis. Total RNA was then extracted after various times and COX-2 mRNA was measured by real-time PCR. Data are presented as a relative to mRNA level at the time of addition of actinomycin D.

MicroRNA Preparation and Microarray Assay

Two strains each of COPD and control fibroblasts were pretreated either in the presence or absence of IL-1β/TNF-α (2 ng/ml each) for 24 h. MicroRNAs were extracted using mir Vana miRNA Isolation Kit (Ambion, Applied Biosystem, Austin, Tex.) following the manufacturer's instructions. MicroRNA expression was profiled by using mir Vana miRNA Labeling Kit and mir Vana miRNA Probe Set 1564V2 (Ambion) following the manufacturer's instructions. Raw data were analyzed by using GenePix Pro 6.1 (Molecular Devices, Sunnyvale, Calif.).

Transfection of microRNA Mimic or Inhibitor

Cells were plated into 6-well plates at a density of $1 \times 10^5$ cells/well in 2 ml DMEM with 10% FBS without antibiotics and fungizone. At 50% confluence, cells were treated with IL-1β/INF-$α_y$ (2 ng/ml each) for 24 h and then transfected with microRNA Mimic or Inhibitor. The transfection was conducted by the same procedure for miRNAs using negative control miRNA, miRNA-146a Mimic or miRNA-146a Inhibitor (final concentration=50 nM each). After 6 hours transfection, cells were further cultured for 24 h and then assayed for $PGE_2$ and COX-2.

Luciferase Reporter Assay

A luciferase (LUC) reporter construct containing 3' untranslated region (UTR) of COX-2 mRNA (COX-2 3' UTR-LUC construct; Catalog No.: HmiT015598-MT01) and a negative control vector (Catalog No.: CmiT000001-MT01) were obtained from GeneCopoeia (Germantown, Md.), and transformed following the manufacturer's instructions. Plasmid cDNAs were purified using Plasmid Maxi Kit (QIAGEN Sciences, Germantown, Md.) following manufacturer's instructions. Cells were seeded in 24-wells plates and cotransfected with COX-2 3' UTR-LUC construct (750 ng), negative control (750 ng), pRL-SV40 vector (50 ng, Promega, Madison, Wis.), miR-146a Mimic (50 nM), miR-146a Inhibitor (50 nM) and negative control miRNA (50 nM), depending on treatments and following Lipofectamine 2000 reagent protocol. Cell layers were harvested 48 h after transfection, and LUC and *Renilla* activities were determined by Dual-Luciferase Reporter Assay System (Promega) and luminometer (MicroLumat Plus-LB96V, EG&G Berthold, Bad Wildbad, Germany). The LUC values were normalized with *Renilla* values and presented as fold change compared with control.

Statistical Analysis

Data are expressed as mean±standard error of the mean (SEM). All data were analyzed using the GraphPad Prism 4 (GraphPad Software, San Diego, Calif.). Analysis of variance was performed with the use of the non-parametric Kruskal-Wallis test. When applicable, the Mann-Whitney U test was used for comparisons between groups. Correlation coefficients were calculated with the use of Spearman's rank method. A P value of <0.05 was considered significant.

The following examples are provided to illustrate certain embodiments of the invention. They are not intended to limit the invention in any way.

Example 1

Reduced microRNA-146a Increases COX-2 Expression and $PGE_2$ Production in COPD Fibroblasts Alterations in tissue structure compromise lung function and directly lead to morbidity and mortality in chronic lung disease. Therapeutic modulation of tissue repair and remodeling processes offers an opportunity to slow the progression of chronic lung disease and, potentially, to restore lung function. In chronic obstructive pulmonary disease (COPD), several tissue lesions are important. In the small airways, fibrosis with airway narrowing is a major cause of airflow limitation. Deeper in the lungs, in the alveolar structures, destruction of lung parenchyma is the defining feature of emphysema. Inhibition of fibrosis, therefore, would be appealing to treat the airway component of COPD. However, in the alveolar structures, repair appears to be deficient, and stimulation of repair is appealing. Thus, an ideal treatment that targets tissue remodeling in COPD should inhibit fibrotic repair in the airways but should stimulate repair of the alveoli.

Our studies demonstrate differential expression of microRNAs in airway vs. alveolar fibroblasts. Several of these microRNAs can down-regulate enzymes in the biosynthetic pathway for prostaglandin E (PGE), which is a potent inhibitor of fibroblast-mediated repair, and are over-expressed in airway vs. alveolar cells. Thus, microRNA-based strategies have the potential to effect tissue remodeling which would benefit the COPD patient. By augmenting airway PGE production, such miRNAs could inhibit fibrosis and, in addition, by inhibiting alveolar PGE production, they could remove suppression of repair in emphysema.

Figure 2:
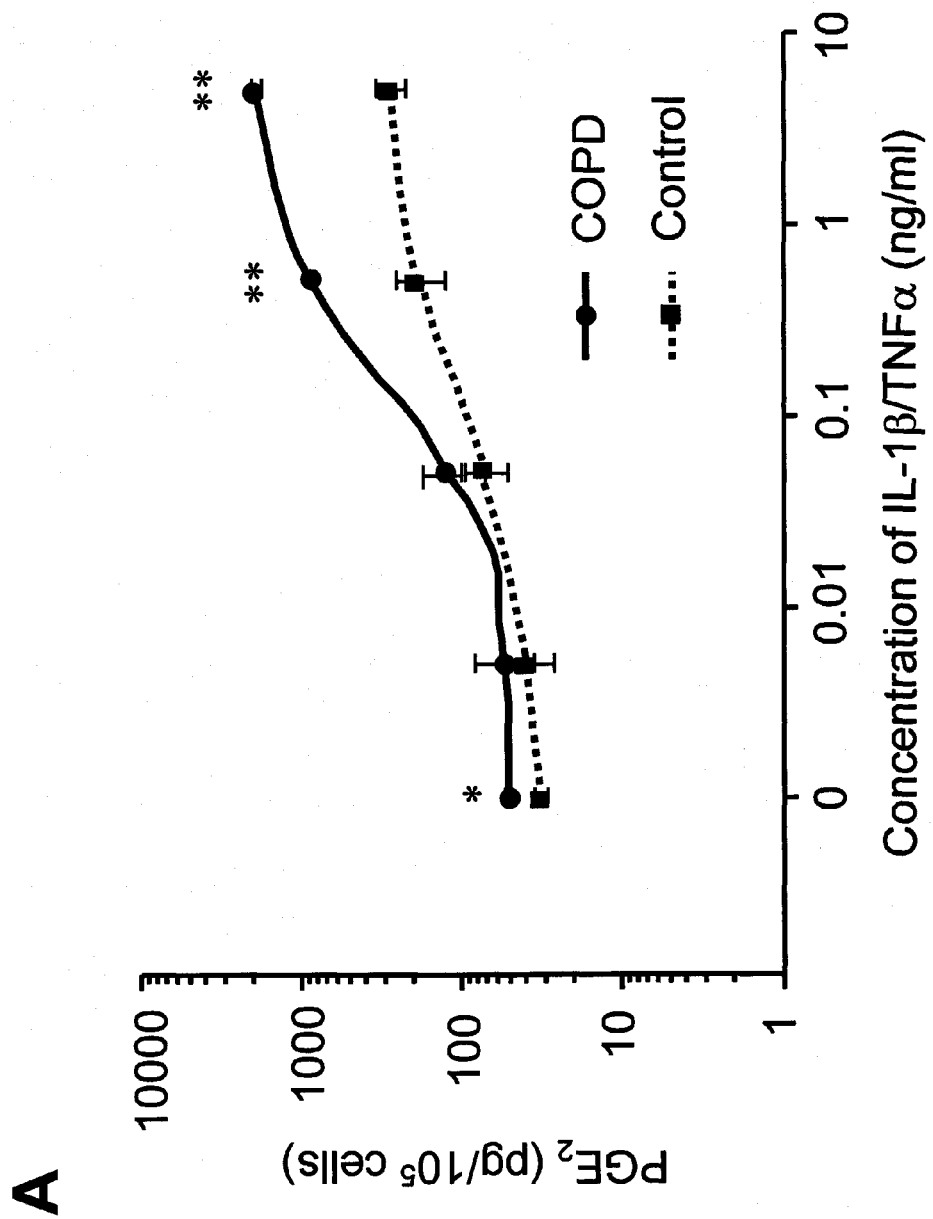
FIG. 2. Effect of IL-1β/TNF-α on $PGE_2$ production and COX-2 protein expression by COPD and control fibroblasts. (A) Concentration-response curve for IL-1β/TNF-α induced $PGE_2$ production. $PGE_2$ was measured after stimulation with varying concentrations of IL-1β/TNF-α for 24 h. (B) Time course of IL-1β/TNF-α induced $PGE_2$ production. Cell culture media were harvested at various time points following stimulation with 2 ng/ml of IL-1β/TNF-α stimulation. Note that the vertical axis which shows $PGE_2$ production is a log scale. (C, D) Densitometric analysis of COX-1 (C) and COX-2 (D) protein expressions by western blotting are shown relative to the basal level of expression in control subjects (indicated by an arrow) after normalization to β-actin. * $P<0.05$,  $P<0.01$, * $P<0.001$ compared with control group.
Figure 2:
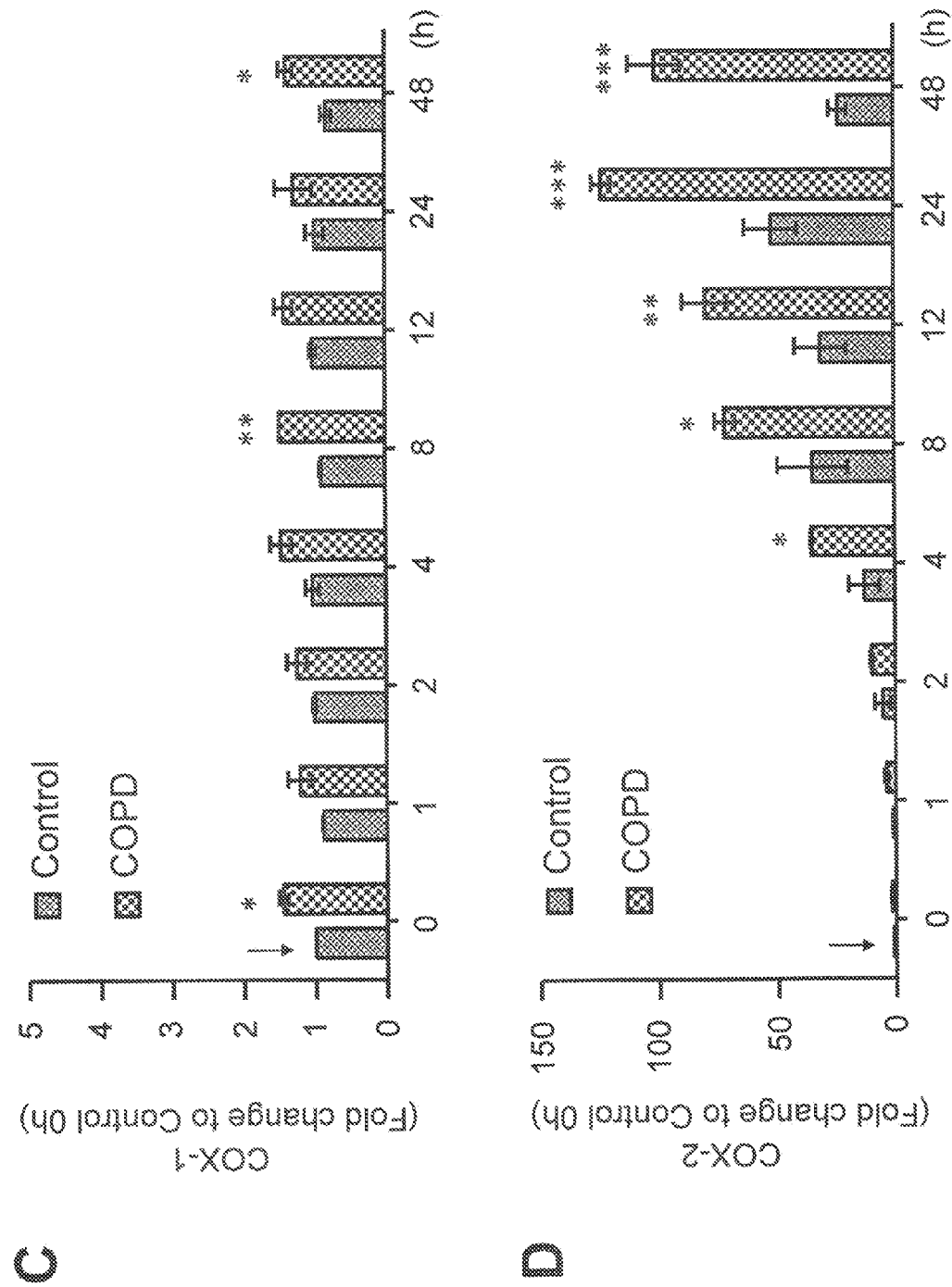

$PGE_2$, which is the major eicosanoid produced by fibroblasts, is released at low levels during basal conditions, but is released at much higher levels in response to a variety of stimuli including inflammatory mediators such as interleukin (IL)-1β and tumor necrosis factor (TNF)-α that are believed to play roles in COPD. Thus, it was important to determine $PGE_2$ production by COPD fibroblasts in response to these inflammatory mediators. To accomplish this, we have evaluated lung fibroblasts from 8 non-COPD (control) and 9 COPD subjects (presented in Table 1 above). Under basal conditions, these cells demonstrated a trend toward increased production of $PGE_2$ (P=0.09), consistent with our previous results (15), which demonstrated a significant difference with 25 tested strains. More importantly, herein we present results demonstrating that fibroblasts from subjects with COPD produce more $PGE_2$ than do control fibroblasts following exogenous stimulation with IL-1β and TNF-α (IL-1β/TNF-α) (P<0.01, FIG. 1A). The magnitude of the stimulation in COPD fibroblasts also showed a trend towards a greater increase (P=0.07), increasing approximately 46-fold compared to the 22-fold increase in control cells, despite the COPD cells having a greater baseline $PGE_2$ production. IL-1β/TNF-α stimulated $PGE_2$ production from both COPD and control fibroblasts in a concentration-dependent manner with a similar 50% effective dose (2.10 vs. 1.63 ng/ml; FIG. 2A). The time-course of IL-1β/TNF-α induced PGE$_2$ production was also similar and showed that PGE$_2$ levels from both COPD and control fibroblasts started to increase by 4 h and reached a maximum around 24 h after treatment (FIG. 2B).

The current study also suggests that increased PGE$_2$ production and response to IL-1β/TNF-α likely results from different mechanisms that account for increased baseline production. Specifically, following IL-1β/TNF-α stimulation, there was an increase in the expression of cyclooxygenase (COX)-2 in both COPD and control fibroblasts, but the increase was much greater in the COPD cells assessed by protein expression (FIG. 1B, 2D). This contrasts with a tendency for increased COX-1 expression in the COPD fibroblasts under baseline conditions that did not change following stimulation with IL-1β/TNF-α (FIGS. 1B, 2C). Measurement of COX enzymatic activity demonstrated a trend toward an increase in basal conditions that was entirely due to COX-1 (FIG. 1C). Following stimulation with IL-1β/TNF-α, the significant increase in COX activity, which was greater in the COPD fibroblasts, was due to COX-2. This suggests that COX-1 may account for the increased basal production of PGE$_2$ but that increased PGE$_2$ production in response to IL-1β/TNF-α is due to COX-2. A key role for COX-2 in the IL-1β/TNF-α induced production of PGE$_2$ was also supported by inhibitor studies. Pharmacologic inhibition with a COX-2 selective inhibitor, NS-398, completely blocked IL-1β/TNF-α induced PGE$_2$ production. In contrast, use of a COX-1 selective inhibitor, SC-560, had no effect on IL-1β/TNF-α induced PGE$_2$ production in control fibroblasts, but inhibited PGE$_2$ release in COPD cells by about 50% (FIG. 1D). Use of a small interfering RNA (siRNA) to suppress COX-2 mRNA also resulted in complete inhibition of IL-1β/TNF-α induced PGE$_2$ production whereas a COX-1 targeting siRNA had no effect (FIG. 1E). These results demonstrate that the increase in COX-2 appears to be essential in mediating the increased PGE$_2$ production by COPD fibroblasts following IL-1β/TNF-α stimulation. A role for COX-1 in COPD cells is not excluded: the lack of effect of the siRNA could be due to incomplete suppression; alternatively the partial inhibition by SC-560 could have been due to non-specific effect of the inhibitor, although this was not seen in control cells.

Having demonstrated the importance of COX-2, we next sought to understand the mechanisms for its increased expression. Following IL-1β/TNF-α stimulation, there was a time dependent increase in COX-2 mRNA in both COPD and control fibroblasts. The increase in COPD cells was of greater magnitude (FIG. 1F). Interestingly, the increased level also appeared to be more persistent in COPD fibroblasts. As this persistence might reflect a difference in mRNA stability, we next evaluated COX-2 mRNA stability in IL-1β/TNF-α treated COPD and control fibroblasts. The half-life of COX-2 mRNA in IL-1β/TNF-α stimulated fibroblasts assessed after actinomycin D treatment was significantly longer in the two COPD fibroblast strains tested compared to the two control cell strains tested (11.9 h vs. 4.61 h, P<0.01; FIG. 1G).

MicroRNAs (miRNAs) are a novel family of small approximately twenty-two nucleotide noncoding RNAs. They are transcribed from specific genes and generally undergo two cleavage steps that result in mature miRNAs. The mature miRNAs, which are expressed in a developmental stage, tissue or cell type specific manner, cause posttranscriptional gene repression by increasing mRNA degradation or by inhibiting translation (21). This is achieved by homology between the miRNA and the 3' untranslated region (UTR) of target mRNAs. Nearly 1000 miRNAs have been described in mammals and over 500 have been identified in humans (22).

Figure 3:
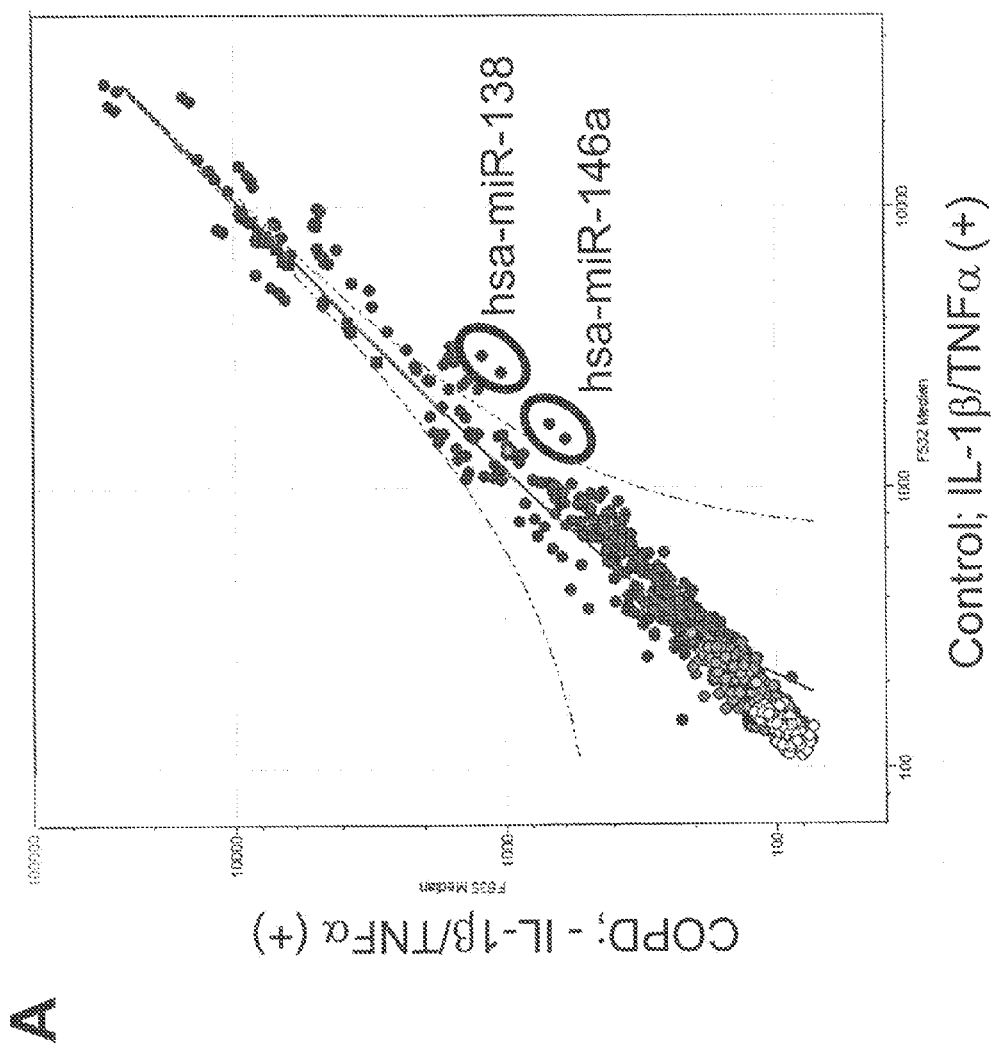
FIG. 3. Homo sapiens miR-146a (Hsa-miR-146a) as a candidate for differential regulation of COX-2 mRNA in COPD compared to control fibroblasts. (A) Microarray profiling of miRNAs. The vertical axis represents relative expression in COPD cells and the horizontal axis represents control. Two representative miRNAs (hsa-miR-146a and 138) that were reduced in both test spots in COPD fibroblasts compared to control are shown. Similar results were obtained with separate strains of COPD and control cells. (B) The structure and homology of the predicted interactions between the 3' UTR of COX-2 mRNA (SEQ ID NO: 1) and hsa-miR-146a (SEQ ID NO: 2). (C) Effect of IL-1β/TNF-α on miR-146a expression in COPD and control fibroblasts. MiR-146a expression is normalized to the amount of rRNA and expressed as fold change compared to the non-stimulated control fibroblasts. Each dot represents a separate subject. * $P<0.05$. (D) Correlation between miR-146a expression and $PGE_2$ production following IL-1β/TNF-α stimulation. COPD subjects are indicated by the open squares, and control subjects by the solid squares.
Figure 3:
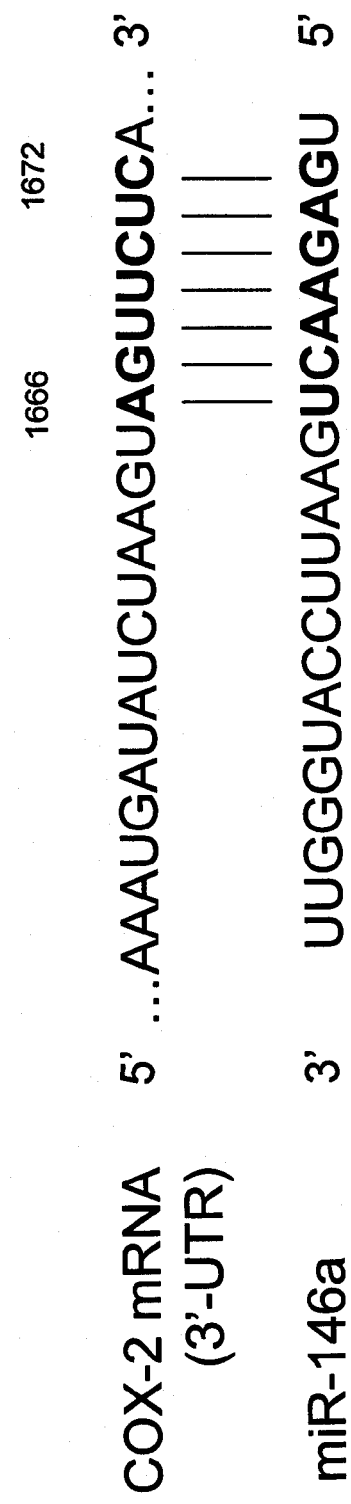
Figure 3:
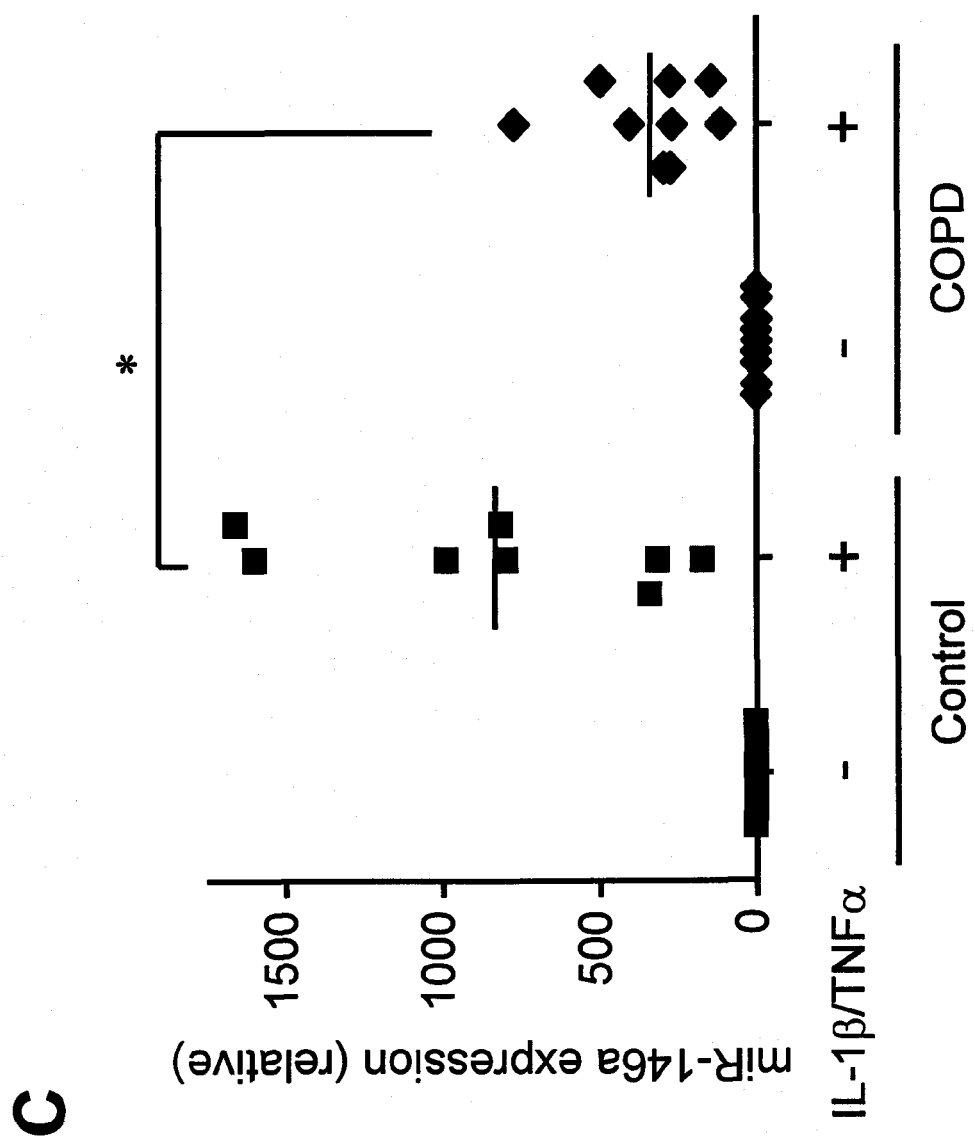
Figure 3:
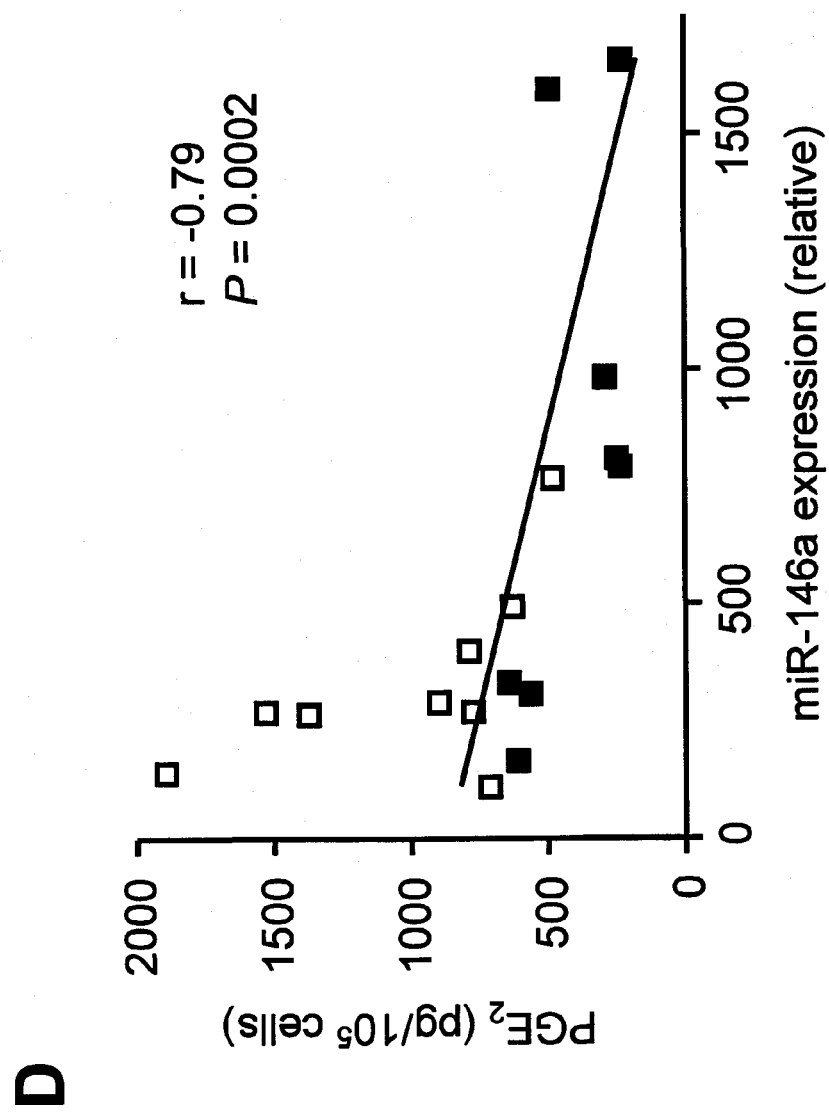

In mammals, miRNAs have been associated with diverse biological processes, such as development, cell differentiation and the pathogenesis of various diseases. With regard to PGE$_2$ biosysthesis, several miRNAs have been reported to regulate COX-2 including miR-16 (23), miR-101 (24, 25) and miR-199a* (25). A search using the online database: TargetScan 5.0 (http://www.targetscan.org) predicted that COX-2 should have homologies with 139 human miRNAs. We hypothesized, therefore, that altered miRNA expression may contribute to altered COX-2 regulation and PGE$_2$ overproduction in COPD fibroblasts in response to IL-1β/TNF-α. To assess this, we selected two strains each of COPD and control fibroblasts and used microarray to assess miRNA expression with and without IL-1β/TNF-α treatment. Two potential candidates were under-expressed in COPD fibroblasts compared to control following IL-1β/TNF-α stimulation, miR-146a and miR-138, each of which was assessed by two spots on the microarray as shown in FIG. 3A. Using online databases (TargetScan, miRanda and MiRBase Sanger), miR-146a was found to have a homology with the COX-2 3' UTR (FIG. 3B), while miR-138 had no homology revealed. We next assessed miR-146a expression both at baseline and following IL-1β/TNF-α stimulation in all 17 strains of COPD and control fibroblasts. Consistent with the results of a previous report (26), IL-1β/TNF-α induced the expression of miR-146a. Importantly, the magnitude of the induction was significantly less in COPD fibroblasts than in control cells (FIG. 3C). The expression of miR-146a also showed negative correlation to PGE$_2$ production following IL-1β/TNF-α stimulation (r=−0.79, P=0.0002; FIG. 3D). Taken together, these results suggest that miR-146a plays a key mechanistic role in the augmented expression of COX-2 in COPD fibroblasts.

Using microarray analysis, we have consistently found reduced induction of miR-146a expression in COPD fibroblasts versus controls upon IL-1β/TNF-α stimulation. In addition to miR-138 (having homology to mRNA for mPGES-2), we have noted several other miRNAs that demonstrate reduced expression in stimulated COPD versus control fibroblasts. These include miR-122, miR-143, miR-144, miR-101, miR-16, miR-26, and miR-24 (see Table 2).

TABLE 2

MicroRNA Screening and Evaluation.*

| MicroRNA | COPD to Control Ratio | IL-1β/TNF-α to Control Ratio | Expression (units) IL-1β/TNF-α Stimulation | Homologies (TargetScan 5.0) |
|---|---|---|---|---|
| 146a | 0.58 | 1.92 | 822 | cPLA2, COX-1, COX-2, mPGES-2 |
| 122 | 0.75 | 1.25 | 5283 | COX-1 |
| 143 | 0.68 | 0.73 | 581 | COX-2 |
| 144 | 0.45 | | 113 | cPLA2, COX-1, COX-2 |
| 101 | 0.51 | | 156 | COX-2 |
| 16 | 0.90 | 0.81 | 3863 | |
| 26 | 0.99 | 0.70 | 2966 | COX-2 |
| 138 | 0.92 | 0.67 | 2613 | mPGES-2 |
| 24 | 0.97 | 0.69 | 4256 | mPGES-1 |

*Data are means compiled from microarrays comparing two control and two COPD fibroblast strains that were evaluated under baseline conditions and following IL-1β/TNF-α stimulation. Candidates were selected if there was reduced expression in COPD compared to control fibroblasts in at least two of the four microarrays evaluated. Expression is in arbitrary units. Values less than 500 are of questionable accuracy.

Figure 4:
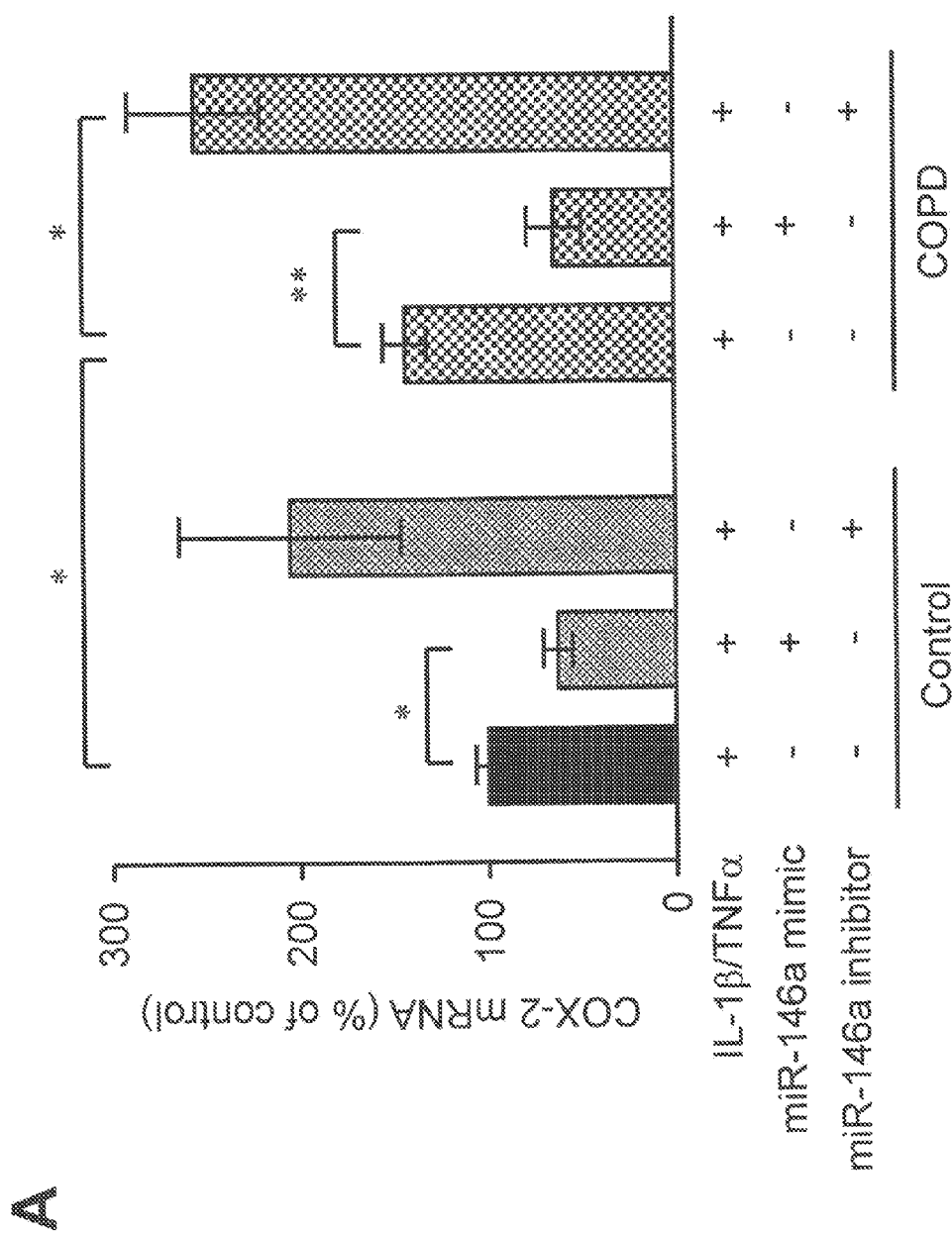
FIG. 4. MiR-146a regulates COX-2 mRNA expression and stability in COPD and control fibroblasts via a direct binding to 3' UTR of COX-2 mRNA. (A) Effect of miR-146a mimic or inhibitor on COX-2 mRNA expression. COX-2 mRNA level is normalized to the amount of rRNA and expressed as a percentage of control (indicated as a black bar). (B) Effect of miR-146a mimic on COX-2 mRNA stability. (C) Effect of miR-146a inhibitor on COX-2 mRNA stability. COX-2 mRNA level is normalized to the amount of rRNA and is expressed as a percentage of mRNA level at the time of adding actinomycin D. (D) Effect of miR-146a mimic or inhibitor on luciferase activity using COX-2 3' UTR-LUC and control vectors. Data are normalized against *Renilla* luciferase activity and expressed as a relative value to control (indicated as a black bar). * P<0.05, ** P<0.01.
Figure 4:
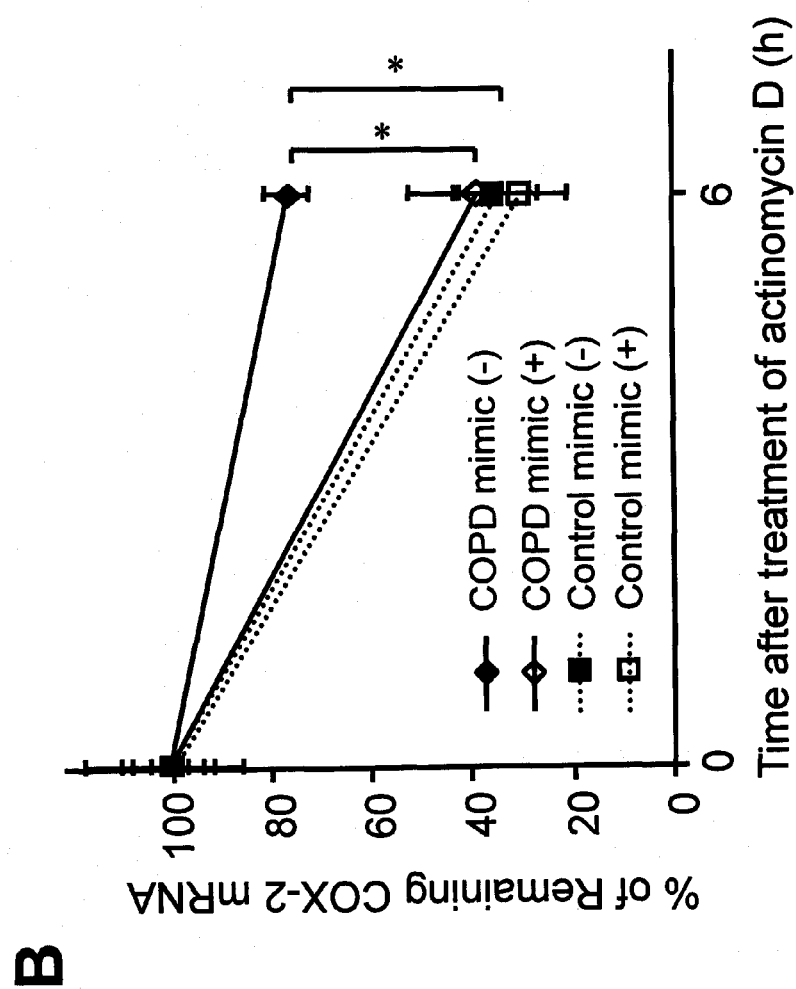
Figure 4:
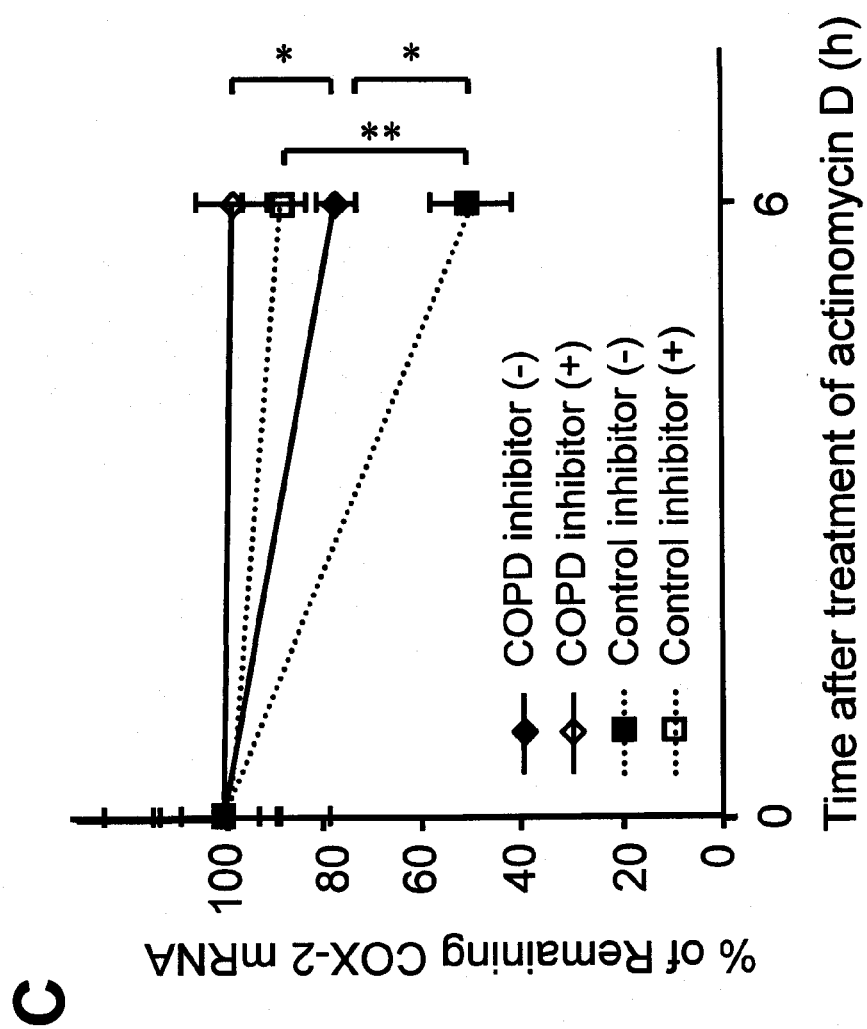
Figure 4:
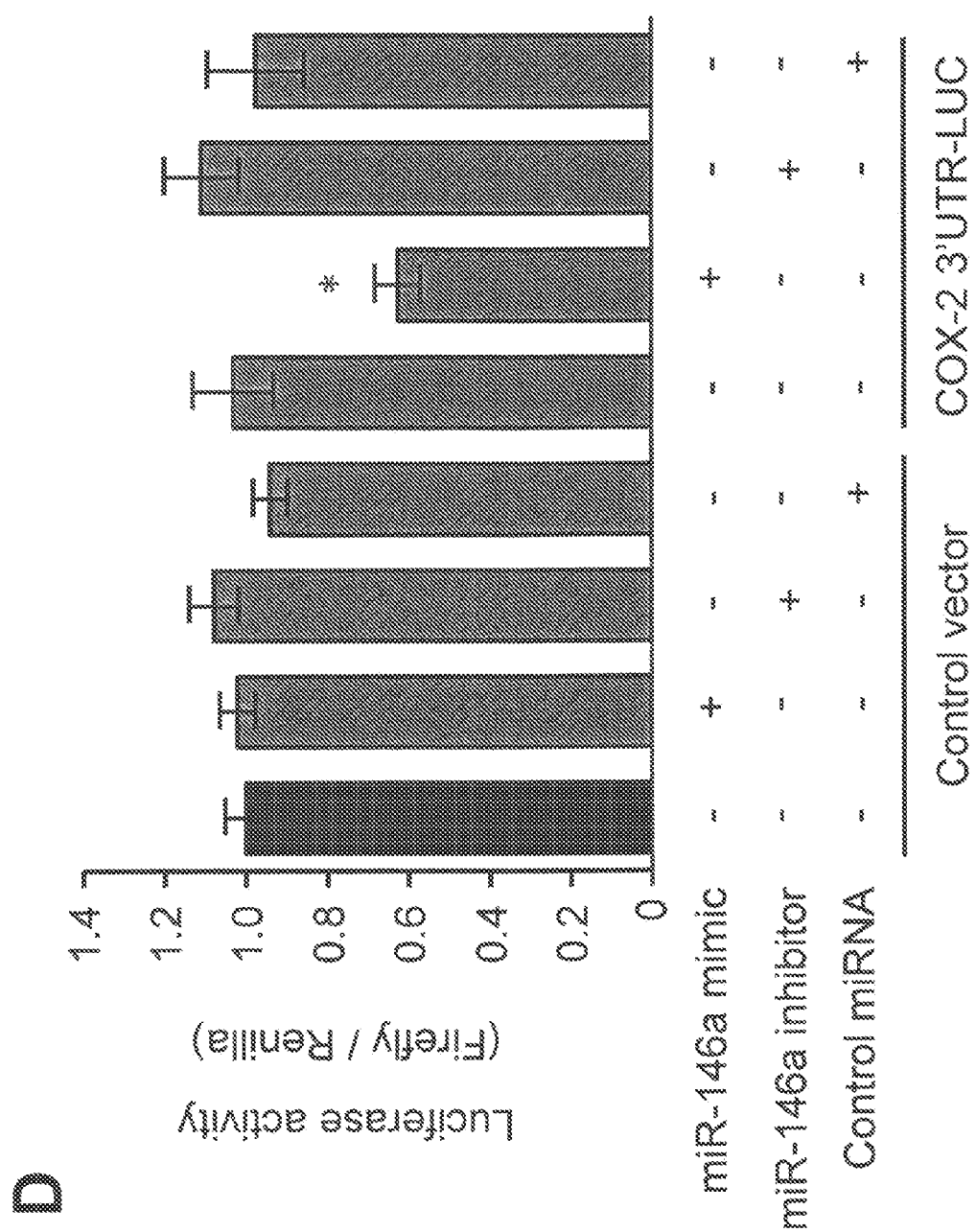

Although we have not used a formal quantitative scoring system, empiric inspection of Table 2 allows comparison and ranking of the candidate microRNAs for several key parameters. MiR-146a was given priority for a number of reasons:

low expression in COPD fibroblasts, stimulation by IL-1β/ TNF-α, expression both at baseline and following IL-1β/ TNF-α and homologies with the mRNA for four candidate PGE biosynthetic enzymes. Another attractive candidate is miR-122, which is decreased in COPD, increased with IL-1β/ TNF-α, exhibits high expression upon stimulation and has homology to mRNA for COX-1. While expression below 500 units makes quantification by microarray difficult, several low expression candidates were also noted. MiR-144 is reduced in COPD, is only detectable following IL-113/ TNF-α stimulation, and has three mRNA homologies (cPLA2, COX-1, and COX-2). MiR-101, which has been reported to regulate COX-2, appeared to be reduced in expression in COPD fibroblasts, although its overall expression was low. Interestingly, the predicted homologies may not detect all functional microRNAs, as miR-16, which has no predicted homology, has been reported to modulate COX-2 (Shanmugam N, et al. *J Biol. Chem.* 2008 Dec. 26; 283(52): 36221-33.), perhaps by indirect effects. To determine the mechanistic role played by miR-146a, we transfected COPD and control fibroblasts with miR-146a mimics, which are double-stranded oligonucleotides designed to mimic microRNA function, or inhibitors, which are oligonucleotides designed to inhibit endogenous microRNA function, obtained from Dharmacon. An miR-146a mimic reduced COX-2 mRNA levels when transfected into both COPD and control fibroblasts and an miR-146a inhibitor had the opposite effect (FIG. 4A). Moreover, we confirmed this mechanism of action by demonstrating that the miR-146a mimic reduced the prolonged COX-2 mRNA half-life present in COPD fibroblasts (FIG. 4B) and that the miR-146a inhibitor enhanced the stability of COX-2 mRNA (FIG. 4C). Finally, we demonstrated binding of miR-146a to COX-2 3' UTR using a luciferase reporter assay as described (24). The luciferase activity significantly decreased only after cotransfection with both the luciferase reporter construct containing COX-2 mRNA 3' UTR and miR-146a mimic (FIG. 4D).

Figure 5:
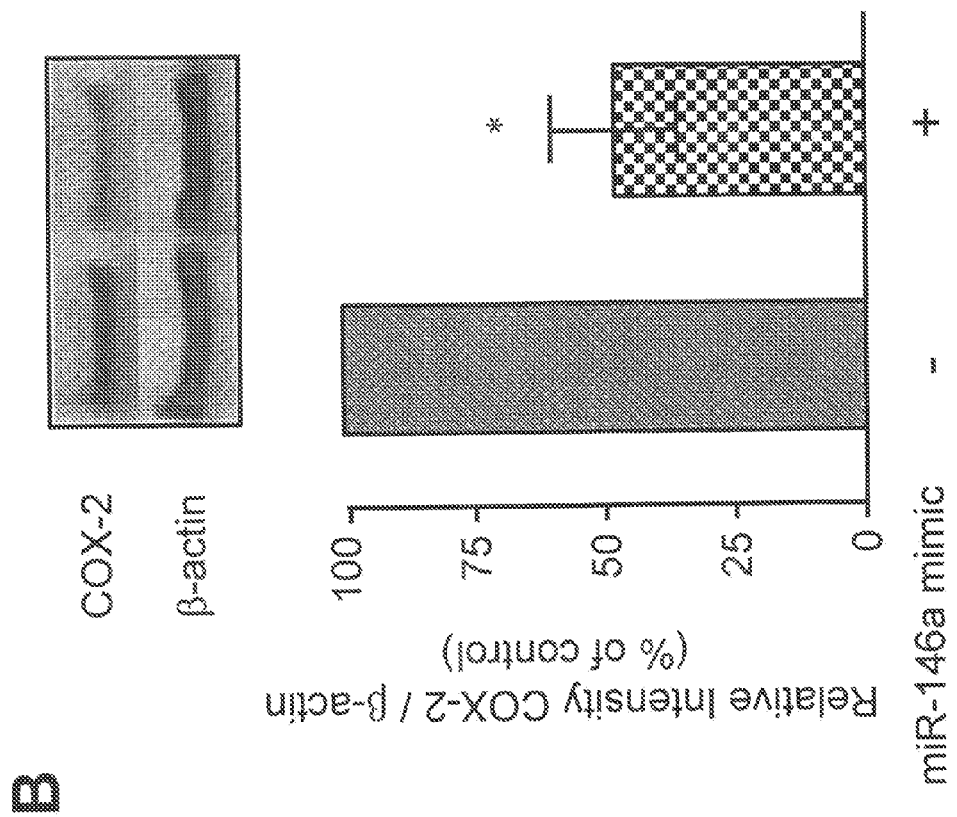
FIG. 5. Relationship of miR-146a to $PGE_2$ production and lung function in COPD. (A) Effect of miR-146a mimic on $PGE_2$ production in COPD fibroblasts. (B) Western blot analysis of COX-2 protein expression using miR-146a mimic. Densitometric quantification of COX-2 is expressed relative to control after normalization to β-actin. (C, D) Correlations between miR-146a expression following IL-1β/TNF-α stimulation and lung function in subjects: $FEV_1$ (C) and $DL_{CO}$ (D). COPD subjects are indicated by the open squares, and control subjects by the solid squares. $FEV_1$ values are from all 17 subjects and $DL_{CO}$ were from 7 subjects of each group. * P<0.05, ** P<0.001.
Figure 5:
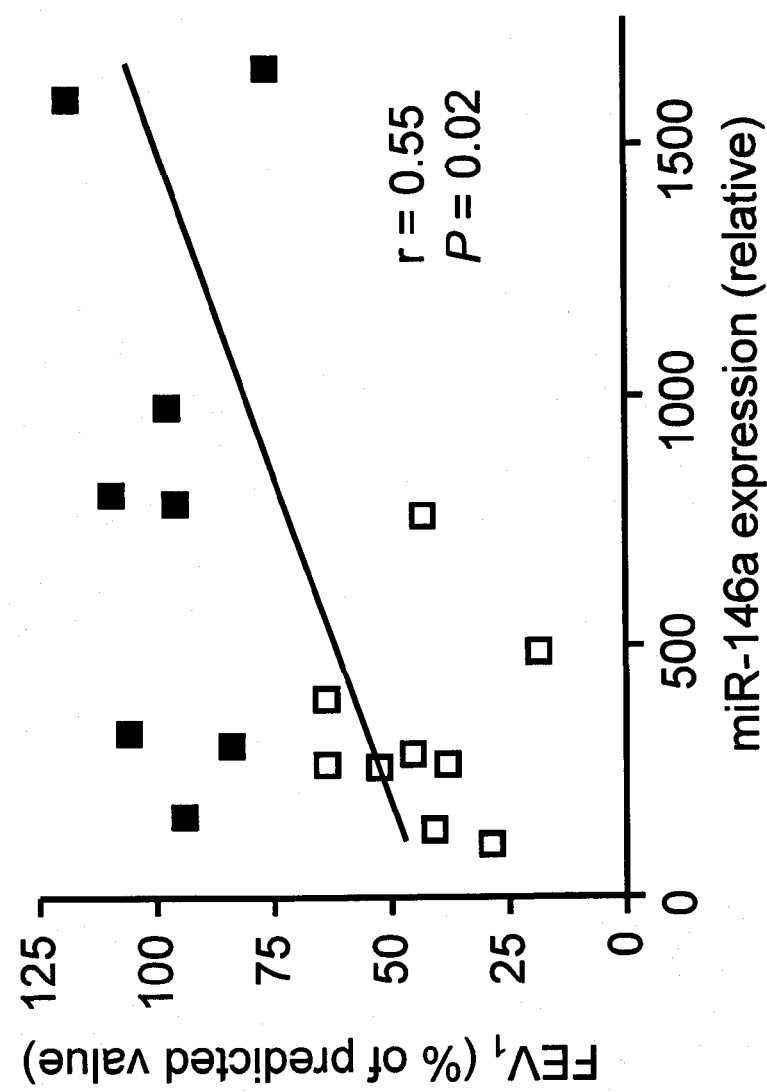
Figure 5:
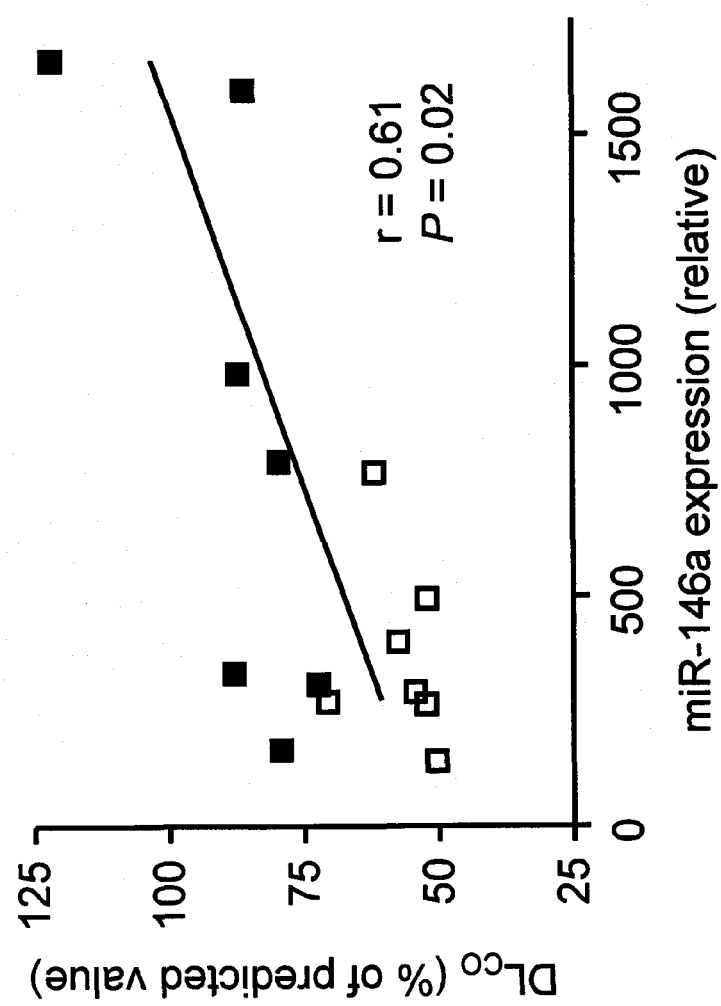
Figure 6:
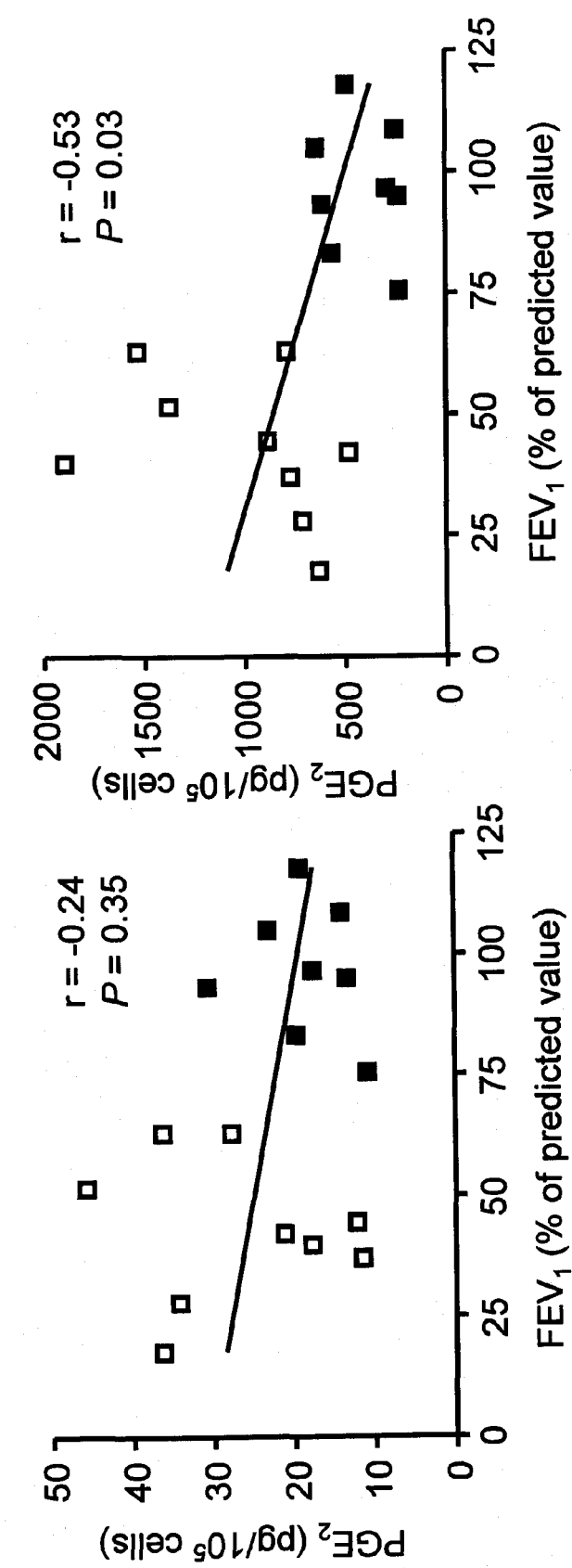
FIG. 6. Correlations between $PGE_2$ production from COPD and control fibroblasts and lung function subject: Correlation of $FEV_1$ with baseline (without IL-1β/TNF-α treatment, Panel A) and stimulated (with IL-1β/TNF-α treatment, Panel B). Correlation of $DL_{CO}$ with baseline (C) and stimulated (D). $PGE_2$ was quantified after 24 h treatment with or without 2 ng/ml of IL-1β/TNF-α. COPD subjects are indicated by the open squares, and control subjects by the solid squares. The solid line shows the regression line. $FEV_1$ values are from all 17 subjects and $DL_{CO}$ were from 7 subjects of each group.

The functional role of miR-146a in COPD fibroblasts was then established by demonstrating significantly reduced $PGE_2$ production and COX-2 protein expression with the transfection of miR-146a mimic into COPD fibroblasts (FIG. 5A, B). Finally, an inverse correlation was demonstrated between induction of miR-146a expression and, not only $PGE_2$ production following IL-1β/TNF-α stimulation, but also with both $FEV_1$ and $DL_{CO}$, two physiologic measures that characterize the severity of COPD and emphysema (FIG. 5C, D). In addition, there was also a correlation between $PGE_2$ production following IL-1β/TNF-α stimulation and these physiologic measures (FIG. 6). Taken together, these observations implicate miR-146a as a modulator of the clinical features of COPD.

The results described herein have established that COPD fibroblasts over-produce $PGE_2$ in response to the inflammatory mediators IL-1β/TNF-α and that under-expression of the miR-146a mediates this effect. These findings have several implications for both the understanding of COPD pathogenesis and for developing novel therapies. Regarding the latter, miR-146a is a pathway that could be targeted to modify $PGE_2$ thereby altering tissue repair and remodeling. The miR-146a pathway, therefore, provides a new therapeutic target in COPD.

A key feature of COPD is the persistence of inflammation long after removal of the inciting stimulus, most commonly cigarette smoking. While a number of mechanisms that account for induction of inflammation following exposure to cigarette smoke have been described, the underlying molecular basis for this persistence remains to be defined. The current study indicates that under-production of an miRNA, specifically miR-146a, is a key mechanism in this regard. With regard to $PGE_2$ production, miR-146a can be thought of as an internal feedback control mechanism. IL-1β and TNF-α induce PGE production, which, in lung fibroblasts, is entirely dependent on COX-2. MiR-146a, which is also induced by IL-1β and TNF-α (25), serves to limit this effect by inducing the degradation of COX-2 mRNA. Under-production of miR-146a, therefore, leads to increased $PGE_2$ production due to prolonged mRNA expression.

The reduced production of miR-146a, therefore, could also contribute to other aspects of the abnormal inflammatory response in COPD. In particular, by reducing a mechanism for decreasing the duration of the inflammatory response, reduced expression of miR-146a could alter the time frame of the inflammatory response in COPD. How this might lead to inflammation that persists over time frames of years remains to be determined. Nevertheless, the current study establishes a pathogenetic mechanism that contributes to the abnormal inflammatory response in COPD, i.e., reduced expression of miR-146a, with loss of a key control serving to limit the intensity and duration of production of the inflammatory mediator $PGE_2$.

Example 2

Differential Modulation of PGE Biosynthesis in Airway vs. Alveolar Fibroblasts

Several structural alterations contribute to the airflow limitation that characterizes COPD. Most important among these are two processes: 1) fibrosis and narrowing of small airways; and 2) destruction of alveolar walls, which is the defining feature of emphysema. Both lesions are believed to result from damage induced by cigarette smoking or other exposures that is amplified by the inflammatory response.

Airway fibrosis, like other forms of fibrosis, results from the accumulation and activation of mesenchymal cells, particularly fibroblasts or myofibroblasts, that produce and remodel extra-cellular matrix. Emphysema, in contrast, results from tissue destruction that exceeds the capacity to repair resulting in net tissue loss. These two lesions, therefore, reflect two nearly opposite consequences of tissue injury: over-exuberant repair and inadequate repair.

Inhibition of mesenchymal cell repair responses is an appealing strategy to treat fibrosis. Mice genetically deficient in Smad3 are resistant to bleomycin-induced fibrosis, presumably by preventing TGF-β-induced stimulation of fibroblasts. Unfortunately, these animals spontaneously develop airspace enlargement that resembles emphysema, which likely results from inadequate maintenance of tissue integrity.

Therapy that could augment repair, in contrast, is appealing to treat emphysema. In rodent models, retinoids are able to stimulate repair and restore lung structure following the development of either elastase or cigarette-smoke induced emphysema. Unfortunately, similar effects have not been observed in human emphysema patients. One explanation for this could be active inhibition of repair responses.

Fibroblasts cultured from patients with emphysema, for example, have reduced repair functions in vitro. This is, in part, due to over-production of prostaglandin E (PGE) by emphysema fibroblasts. PGE has well-described inhibitory effects on fibroblasts, and increased levels of PGE have been reported in patients with COPD. Blockade of PGE action, therefore, would be appealing to restore repair functions in the alveolar structures of COPD patients with emphysema.

Unfortunately, several observations suggest that inhibition of PGE production may adversely affect airway fibrosis, which is the other major lesion that contributes to airflow limitation in patients with COPD. Fibrotic lung disease is associated with reduced levels of PGE in BAL fluid. Similarly, reduced production of PGE by fibroblasts from fibrotic lung disease has been reported. These observations have led to the suggestion that low PGE levels lead to uncontrolled fibroblast activity and contribute to the development of fibrosis. What is needed to treat tissue remodeling in COPD patients, therefore, is a means to stimulate PGE production in the airways and to inhibit PGE production in the alveolar structures. MicroRNA based approaches are appropriate to meet this challenge.

Figure 7:
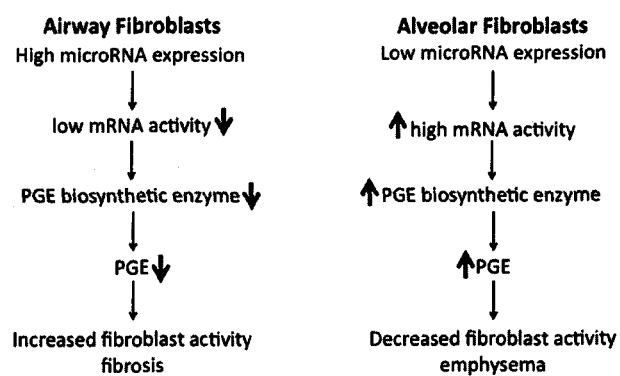
FIG. 7. Consequences of differential microRNA expression. In airway fibroblasts, high microRNA levels suppress PGE biosynthetic enzyme expression leading to low PGE production and increased fibroblast activity. In contrast, in alveolar fibroblasts, low microRNA levels result in increased PGE biosynthetic enzyme expression, high PGE production and decreased fibroblast activity.

MicroRNAs are often expressed in specific tissue locations or during specific stages in development. This makes microRNA-based approaches highly appealing for targeting therapeutic agents to selective sites. In this context, airway and alveolar fibroblasts in the lung differ in a variety of features. We have demonstrated that these differences include differential expression of microRNAs, including several that have the potential to modulate PGE production. Thus one aspect of the invention entails identification and validation of microRNA based strategies that can selectively increase PGE production in airway fibroblasts or selectively decrease PGE production in alveolar fibroblasts. Such techniques should be effective to target tissue remodeling locally within the lung: that is to inhibit fibrosis in the airways and to remove the inhibition of repair in the alveoli. See FIG. 7.

We will exploit differential expression of microRNAs in airway vs. alveolar fibroblasts to narrow the initial identification of candidates to those that are likely to address the clinical problem. In addition, we will utilize PGE production as a functional assay as described in Example 1 to facilitate screening of candidate microRNAs.

As part of an ongoing study, fibroblast cultures are initiated from cells obtained from patients undergoing thoracic surgery, usually for removal of a potentially malignant tumor, who volunteer to have portions of their surgical specimen processed for research. This ongoing study is approved by the human studies committee of Hospital Grosshansdorf, Grosshansdorf, Germany.

To obtain alveolar cells, a portion of alveolar tissue free of and as far removed from the tumor as possible that is also free of pleura, large vessels and large airways is removed immediately after surgery. One portion is used to initiate cell cultures as described. In addition, an adjacent portion of the specimen is routinely inflated and fixed for histology and a second adjacent portion is snap-frozen.

Airway cells are obtained by carefully dissecting airways approximately 3-6 mm in diameter that are free of, and as far from tumor as possible. These are identified by palpation and dissected free of surrounding alveolar tissue. A small portion is then removed and used to initiate cell cultures. Adjacent portions are also routinely fixed in formalin and snap-frozen. These would also be available for histologic and biochemical studies in follow-up projects if needed.

As part of the routine assessment prior to surgery, subjects are evaluated with lung function tests, including lung volumes and DLCO, and by CT scan. This information, as well as clinical history, is used to classify subjects into those with and without COPD based on the GOLD criteria and to determine the presence and severity of emphysema. Fibroblasts are routinely characterized by morphology and by expression of vimentin and keratin. Because subjects are generally the same age and are current or ex-smokers, but vary with regard to the presence and severity of COPD, this population provides both COPD subjects with varying severity of emphysema as well as age- and smoking-matched controls.

Stimuli.

PGE is produced by fibroblasts at relatively low levels under "basal" conditions. However, production increases dramatically following stimulation with inflammatory/repair mediators. For this reason, the role of microRNAs in regulating PGE production under basal conditions and in response to three distinct types of stimuli will be evaluated. These stimuli include 1) the pro-inflammatory cytokines IL-1β/TNF-α (described in Example 1); 2) the pro-fibrotic cytokine TGF-β1; and, because PGE can induce its own expression through a feed forward pathway mediated by the EP2 receptor, 3) the EP2 agonist ONO-AE1-259.

Figure 8:
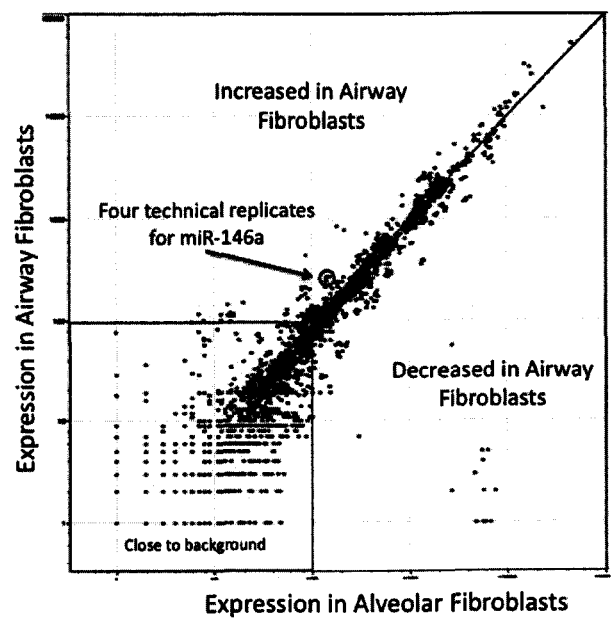
FIG. 8. Differential expression of microRNAs in airway and alveolar fibroblasts. Fibroblasts were isolated from the airway and alveolar structures of a COPD patient volunteer. Cells were cultured in Dulbecco's Modified Eagle's Medium (DMEM) supplemented with 10% fetal bovine serum until confluent. Media were then changed to DMEM without serum with and without IL-1β/TNF-α (2 ng/ml each) and incubated for 24 hours. RNA was then extracted and 1 μg of total RNA from each sample was used to label microRNA with either CY3 or CY5 using miRCURY LNA™ microRNA labeling kit (cat#: 208030-A, Exiqon, Woburn, Mass.) and profiled using miRCURY LNA™ microRNA Array, v. 11.0 (cat#: 208201-A, Exiqon, Woburn, Mass.) according to manufacturers' suggested protocols. The CY3 and CY5 sample pairs were mixed and hybridized overnight at 56° C. The slides were then washed and scanned using an Axon 4000b scanner. Images were analyzed and features extracted using GenePix software. The background corrected CY5/CY3 ratio of the medians were calculated for all four spots located on different regions of the slide as technical controls. Vertical axis: expression in airway fibroblasts. Horizontal axis: expression in alveolar fibroblasts. Cells above the diagonal line (blue) are differentially increased in expression in airway fibroblasts and those below it are decreased. The boxed area (blue) indicates spots close to background that are excluded from further analysis. The four spots that correspond to microRNA hsa-miR-146a, which is over-expressed in airway compared to alveolar cells, are indicated (red circle and arrow) as an example of technical replication and of a microRNA with differential expression. The spots in the lower right are RNA controls.

Pilot screens with paired airway and alveolar fibroblasts from three COPD patients identified differential expression of 28 microRNAs, of which 14 were over-expressed at least 1.5-fold in airway vs. alveolar fibroblasts making them potential candidates for further evaluation (See FIG. 8 and Table 3). Of these, one was over-expressed in fibroblasts from all three subjects, five in two of three subjects and eight in only one subject.

TABLE 3

Differentially expressed microRNAs that are increased in IL-1β/TNF-α stimulated airway fibroblasts compared to alveolar fibroblasts from COPD patients.

| MicroRNA | Ratio airway: alveolar | # subjects with differential expression | Predicted microRNA targets (TargetScan) |
|---|---|---|---|
| miR-335 | 5.8 | 2 | sPLA2(IID), COX-1 |
| miR-140-3p | 2.9 | 2 | |
| miR-886-5p | 2.5 | 2 | sPLA2(IVF), COX-1 |
| miR-146a | 2.4 | 2 | cPLA2(IVD), COX-1, COX-2, mPGES1 |
| miR-138 | 2.3 | 3 | sPLA2(IIF), sPLA2(III), mPGES2 |
| miR-195 | 2.1 | 1 | |
| miRPlus-A1087 | 2.1 | 1 | |
| miR-100 | 1.9 | 1 | |
| miR-146b-5p | 1.8 | 1 | cPLA2(IVD), COX-1, COX-2, mPGES1 |
| miR-214 | 1.7 | 1 | sPLA2(IIF), lysosomal PLA2, PLA2(XIIB) |
| miR-199a-3p/ miR-199b-3p | 1.6 | 1 | cPLA2(IVC), cPLA2(IVD), PLA2(XIIB), |
| let-7i | 1.6 | 2 | sPLA2(IIF), sPLA2(III), |
| miR-193a-3p | 1.5 | 1 | COX-2 |
| miR-365 | 1.5 | 1 | cPLA2(IVB), sPLA2(IIF), sPLA2(III), lysosomal PLA2, COX-1, COX-2, mPGES1, mPGES2 |

Following conventional practice, microRNAs with expression two standard deviations above background, which would generally exclude the spots in the blue boxed region of FIG. 8, with at least three of four technical replicates in close agreement will be forwarded for further analysis. A single value for fold-expression in the airway compared to alveolar fibroblasts can be determined from the mean of the satisfactory technical replicates. For each individual, microRNAs with relative expression>1.5 will be ranked based on relative expression. This will result in a dataset that resembles the first three columns of Table 3.

The microRNAs that are differentially expressed in airway compared to alveolar cells will then be screened in silico for homologies with PGE biosynthetic enzymes. To accomplish this, we intend to use three publicly available databases:

TargetScan (www.targetscan.org); miRanda (www.microrna.org/microrna/home.do); and PicTar (pictar.mdc-berlin.de). All will be used as they use different algorithms that may identify different homologies.

In initial studies, 10 of 14 differentially expressed microRNAs had predicted homologies with PGE biosynthetic enzymes. Many of the microRNAs had homologies with several enzymes, and these often included enzymes that could mediate two or all three steps of PGE biosynthesis. Thus, we expect no difficulty in identifying candidates with the potential to modify PGE biosynthetic enzyme expression. To prioritize among these, we will assemble the microarray data and the in silico screen results into a table similar to Table 3 for each stimulus. The microRNAs that are differentially expressed will then be compared based on the number of strains that demonstrate differential expression, their relative expression in those strains, and the predicted homologies. Although we do not intend to use a formal ranking process, the microRNAs will be compared for these parameters, and leading candidates will be selected. If needed, a formal scoring process will be developed. We anticipate selecting about 10 microRNAs for each of the four conditions for functional screening. Based on our pilot studies, we expect to identify about 30 candidates for each condition using the full set of 10 pairs of cell strains. With this number, we expect no difficulty in prioritizing among the microRNA candidates with the method described above, thus allowing us to forward 10 microRNA candidates for each condition for further screening.

We will perform our functional screen by using mimics and inhibitors for microRNAs that are over-expressed in airway vs. alveolar fibroblasts. Inhibitors, by decreasing the activity of microRNAs in the airway cells would be able to increase PGE production. In contrast, mimics, by down-regulating enzymes not regulated by under-expressed microRNAs in alveolar cells, would be able to reduce PGE production.

For the initial functional screen, we will test each microRNA by evaluating an inhibitor in the two strains of airway fibroblasts that demonstrated greatest over-expression and by evaluating the corresponding mimic in the paired alveolar fibroblasts, in which the microRNA was relatively most under-expressed. These experiments will be accomplished using the methods described in Example 1.

Our initial studies have demonstrated clear effects of microRNA mimics and inhibitors on target mRNA species in lung fibroblasts when the mimics and inhibitors were used at concentrations of 50 nM (data not shown). Because of this, we will opt to screen with a 50 nM concentration. These assays will enable us to identify microRNAs that functionally modulate PGE production. For this reason, each candidate microRNA will be assessed in two pairs of airway and alveolar cells. A microRNA that results in a 50% change in PGE production (that is, an increase in airway fibroblasts or a decrease in alveolar fibroblasts) in both of the strains tested will be considered for further validation. This criterion for magnitude of effect seems reasonable, as our study with miR-146a resulted in about a 3-fold reduction in both of the alveolar fibroblast strains tested. See Example 1.

The mechanism(s) by which a candidate microRNA modulates PGE production will be determined. Specifically we will determine which PGE biosynthetic enzymes are affected, whether mRNA levels are altered and will determine if there is direct binding of the candidate microRNA with the suspected target mRNA.

The same strains of airway and alveolar fibroblasts that were screened functionally will be used. Cells will be stimulated with control medium, IL-1β/TNF-α, TGF-β1 or with EP2 agonist and then treated with microRNA inhibitor (airway fibroblasts) or mimic (alveolar fibroblasts). Media will be harvested to quantify PGE production. Cell layers will be harvested and extracted for RNA and total protein, which will be used to assess PGE biosynthetic enzyme expression. This will be accomplished by performing SDS-polyacrylamide gel electrophoresis on cellular proteins followed by western blotting using antibodies for all three PGE synthases, for both cyclo-oxygenases and for five phospholipase A2s. We will assess cPLA2, iPLA2, sPLA2IIA, sPLA2(V) and sPLA2(X). These PLA2 family members have been chosen as they are generally regarded as most relevant for PGE biosynthesis. Protein expression will be quantified by using a horseradish peroxidase-conjugated IgG second antibody (Rockland, Gilbertsville, Pa.) with an enhanced chemiluminescence plus detection system (ECL plus) and a Typhoon Scanner (Amersham Pharmacia Biotech, Buckinghamshire, England).

Figure 9:
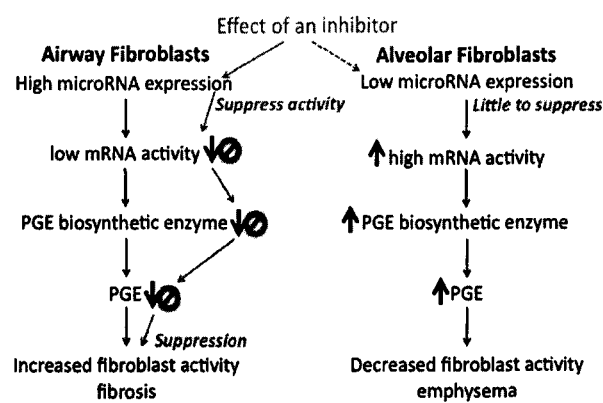
FIG. 9. Effect of an inhibitor on a microRNA over-expressed in airway fibroblasts. An inhibitor would be able to antagonize a microRNA over-expressed in airway fibroblasts (blue solid arrows). This would reverse the suppression of PGE biosynthetic enzymes increasing their expression thus increasing PGE production and suppressing increased fibroblast activity. In contrast (blue dotted arrow), the inhibitor is likely to have little effect on the microRNA in alveolar cells where expression is low. (There would be no effect if the microRNA were not expressed at all.)

An increase in expression of a PGE biosynthetic enzyme when airway cells are transfected with a microRNA inhibitor will support a role for that microRNA in regulating the expression of the enzyme and thus should have efficacy for the treatment of airways fibrosis. The converse experiment will also be conducted. This will help determine the potential for the microRNAs to have specific effects on airway vs. alveolar cells (FIG. 9).

Figure 10:
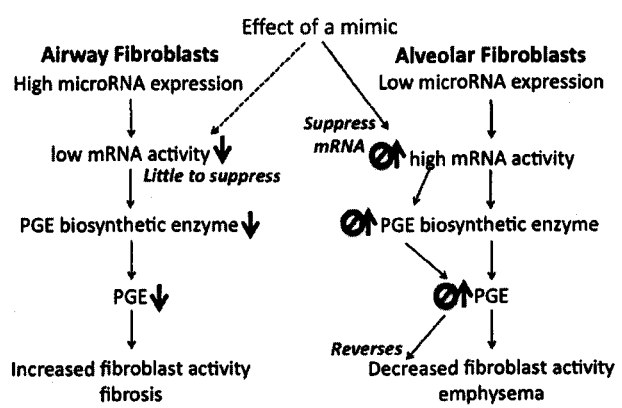
FIG. 10. Effect of a mimic on an alveolar fibroblast with under-expression of a microRNA. The mimic (red solid arrows) would be able to suppress the over-expression of a PGE biosynthetic enzyme that resulted from deficient microRNA. This would reduce PGE production and remove suppression of fibroblast activity. In contrast (red dotted arrow), the mimic may have little effect on airway fibroblasts which have high microRNA expression as the mimic may add little to the suppression already present.

Conversely, a decrease in expression of a PGE biosynthetic enzyme when alveolar cells are transfected with a microRNA mimic will support a role for that microRNA in regulating the expression of the enzyme and would suggest therautic potential to treat emphysema. Again, the converse experiment will be conducted to help determine the potential for the microRNAs to have specific effects on airway vs. alveolar cells (FIG. 10).

If cellular selectivity is suggested with the initial concentration of mimic/inhibitor tested (50 nM), this will be confirmed with concentration-dependence experiments.

MicroRNAs can modulate mRNA and protein expression both by direct effects mediated by binding to the target mRNAs and by indirect effects. The final step in methodologic validation that we will pursue will be to determine if the candidate microRNA directly binds the target mRNA. This will be accomplished as described in Example 1. We will use a reporter construct that includes the predicted target mRNA 3' untranslated region fused to the green fluorescent protein (GFP) coding sequence. A mutated target will be used as a control. Expression of GFP will then be monitored in the target cell following transfection with the reporter constructs with and without microRNA mimic and inhibitor.

We have successfully used the method described above to demonstrate binding of miR-146a to COX-2 mRNA (See Example 1). This method will, therefore, confirm direct binding of the candidate microRNA to the target mRNA, thus supporting the methodologic validation of the candidate microRNA.

For application as a therapeutic, it will be important to confirm the quantitative expression of the relevant microRNA in target cells from patients. This will be accomplished by culturing fibroblasts from the airways and alveoli of 20 COPD patients. Cells will then be treated with the four stimuli (control, IL-1β/TNF-α, TGF-β1 or EP2 agonist), RNA will be extracted and the microRNAs of interest quantified by RT-PCR. For comparison, 10 controls, who will be similar in age and smoking history, will also be studied. These data will permit us to determine the level of expression of microRNAs in airway and alveolar fibroblasts in both COPD and control subjects and will provide information on their expression over a range of conditions.

Candidate microRNAs which are differentially expressed in airway vs. alveolar fibroblasts from COPD subjects will be identified using the foregoing methods. Differential expression assessments will be made under baseline conditions and following stimulation with IL-1β/TNF-α, TGF-β and EP2 agonist. Comparisons between the groups will be made using a non-parametric Mann-Whitney test. Adjusting for a non-parametric analysis, with 20 strains per group, we will have 80% power to detect a standardized effect size of 0.9, a large effect as defined by Cohen where the difference in means is 90% as large as the standard deviation assuming a two-sided 0.05 significance level. This estimate seems conservative as our screening procedures will select for microRNAs with large effects, and our data suggests that candidates will have an effect size of at least a doubling in the ratio of microRNA expression. For the samples available, this corresponds to an average effect about 7-fold that of the standard deviation. Thus, we believe that 20 samples is a conservative estimate and that, with this number of samples available, we will be able to detect much smaller differences. Data for the response to each stimulus will be analyzed separately.

We will be able to determine if microRNA inhibitors are able to increase PGE biosynthetic enzyme expression in airway fibroblasts and if microRNA mimics are able to decrease PGE biosynthetic enzyme expression in alveolar fibroblasts. PGE production will also be quantified. We will also assess the effect of microRNA mimic and inhibitor in the entire population of 20 COPD and 10 control subject samples, thus establishing the plausibility of using the microRNA approach as a therapy for COPD.

Airway and alveolar fibroblasts will be cultured to confluence, stimulated with each of the four conditions (control, IL-1β/TNF-α, TGF-β1 or EP2 agonist) and then transfected with the microRNA mimic, inhibitor or control. After 6 hours media will be changed, and after an additional 24 hours, media will be harvested and PGE quantified by EIA.

An increase in PGE production in airway fibroblasts in response to the microRNA inhibitor would support a strategy targeting airway fibrosis in COPD. Non-parametric Mann-Whitney analyses will be used. Each stimulus condition will be analyzed separately. Our initial data for the effect of mimic on PGE production suggest that the effect size is very large compared to the standard deviation. However, these data were obtained from cells selected to have increased PGE production and smaller effect sizes may be observed in an unselected population. However, in our previous work, 12-13 subjects was sufficient to demonstrate differences in PGE production from fibroblasts from COPD and control subjects.

Secondary analyses will compare PGE production by airway and alveolar fibroblasts, and will compare PGE production of COPD fibroblasts to control. Non-parametric Mann-Whitney analyses will be used. Sample sizes were not based on these secondary analyses, but power to demonstrate differences, without adjustment for multiple comparisons, should be similar to that for the primary hypothesis.

Another question to be assessed is whether the response to microRNA inhibitor is related to COPD severity. COPD subjects will not be selected by stage (based on the severity of the $FEV_1$ impairment) or on severity of emphysema (based on CT scan density). However, both will be determined, and it is expected that a range of severities will be represented in the study population. Correlation analysis will be performed for each stimulus (control, IL1β/TNF-α, TGF-β and EP2 agonist) separately. A total of 30 patients in the control and COPD groups will result in 80% power to detect a significant correlation of at least 0.48 in absolute value. To determine if there is a significant relationship within the COPD group alone, a total of 20 patients will result in 80% power to detect a significant correlation of at least 0.58 in absolute value.

We will also test candidate microRNA mimics to assess whether they selectively inhibit PGE production in alveolar fibroblasts compared to airway fibroblasts from COPD patients.

We will determine if the mimic will suppress PGE production by alveolar fibroblasts from COPD patients. Taken together, the results of these studies will demonstrate that microRNAs are differentially expressed in COPD airway vs. alveolar fibroblasts and that microRNA-based strategies can modify PGE production in these cells. These results indicate that tissue remodeling in COPD can be addressed therapeutically by a microRNA-based approach and will provide evidence that this can be done to address selectively either airways fibrosis or emphysema.

Example 3

Role of miR-146a in Modulation of TGF-β1-Mediated Fibroblast Repair

Chronic inflammation leads to tissue damage and is believed to contribute to structural damage in lung disease. Insufficient repair of alveolar structures may contribute to the development of emphysema while over exuberant repair of small airways may result in peri-bronchial fibrosis. Lung fibroblasts play an important role in tissue repair following the airway inflammation, which is believed to be directed by TGF-β1 signaling, in part, through a family of Smad proteins: Smad2, 3 and 4. MiR-146a, an inflammation responsive microRNA, is dramatically up regulated in lung fibroblasts in response to the pro-inflammatory cytokines, IL-1β and TNF-α, and has homologies with Smad2, 3 and 4. This suggests that miR-146a mediates interactions between IL-1β and TNF-α and TGF-β1. Supporting this concept, our initial studies (disclosed herein) demonstrate that transfection of a miR-146a mimic into human fetal lung fibroblasts (HFL-1) resulted in blockade of TGF-β1 augmented collagen gel contraction.

TGF-β Signaling

Transforming growth factor (TGF)-β is a multifunctional growth factor, which is critically involved in fibroblast proliferation, differentiation, extracellular matrix production and deposition in airways. Several studies have reported that TGF-β1 expression is increased in the airway epithelium of smokers as well as in patients with chronic bronchitis or COPD (27, 28). Furthermore, TGF-β1 expression in the epithelial cells from COPD patients correlated with basal membrane thickness and the number of peri-bronchiolar fibroblasts (29), suggesting TGF-β1 plays an important role in modulating airway tissue remodeling and fibrosis in the milieu of chronic airway inflammation.

Figure 11:
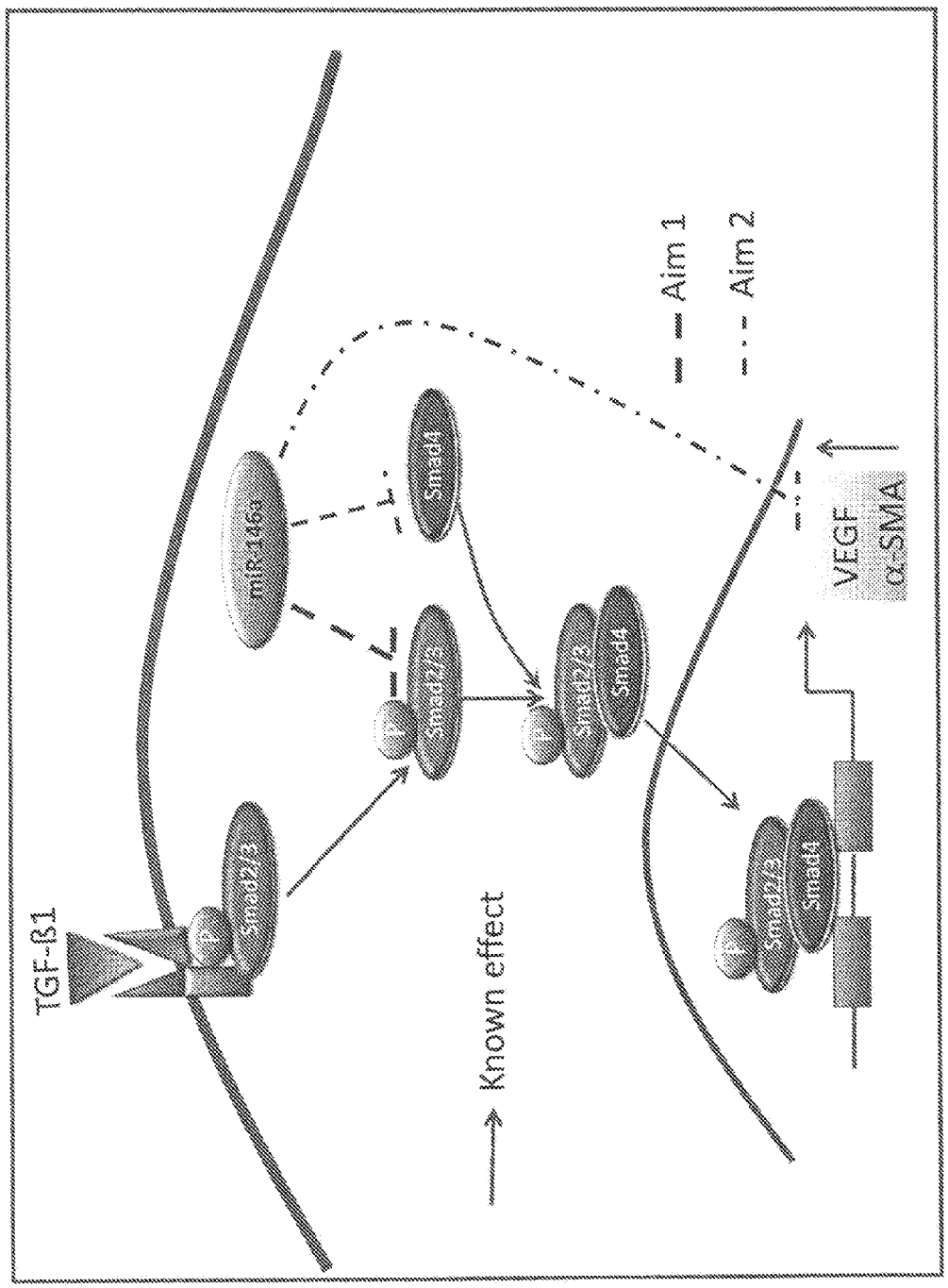
FIG. 11. Schematic illustration miR-146a interruption of TGF-β1/Smad signaling.

The TGF-β family includes three isoforms: TGF-β1, -β2 and -β3. Active TGF-β binds to two signaling receptors, TGF-β receptor II (TβRII) and TGF-β receptor I (TβRI), which initiate the recruitment and phosphorylation of Smad2 and 3. Phosphorylated Smad2 and 3 bind to Smad4, which leads to nuclear translocation of these Smad proteins, where they regulate gene expression (see the schematic diagram shown in FIG. 11). We show that miR-146a suppresses Smad2, 3 and 4 expression and activation, thereby modulating TGF-β1 stimulation on VEGF production and α-SMA expression in HFL-1 cells. TGF-β1 binds to its receptors, which leads to recruitment and phosphorylation of Smad2/3. Phosphorylated Smad2/3 binds to Smad4 and translocates into the nucleus where it turns on gene expression.

Signaling by TGF-β following the binding to its receptors may also be transduced through Smad-independent pathways, including the TGF-β activated kinase 1 (TAK1) and its downstream p38 or JNK pathways (30, 31), and the PI3K/Akt pathways (32, 33). Consistent with studies conducted by others (34), we have reported that Smad3 is required for TGF-β1-stimulated α-smooth muscle actin (α-SMA) expression and vascular endothelial growth factor (VEGF) production (35, 36) and for TGF-β1-augmented collagen gel contraction by human and mouse lung fibroblasts (35, 37). We have also found that, in cells lacking either Smad3 or Smad2, TGF-β1-stimulated fibronectin synthesis is unaltered (unpublished observation), confirming that a Smad-independent pathway is responsible for transducing TGF-β1 signaling leading to augmented fibronectin synthesis by lung fibroblasts.

MiR-146a and Inflammatory Diseases

To date, 940 human miRNAs have been identified (Release 15, April 2010. http://www.mirbase.org), but only a few miRNAs have been reported that might be associated with chronic inflammation. Among the miRNAs that are associated with chronic inflammation, miRNA-146a is one of the most extensively investigated. In this regard, basal expression of miR-146a is elevated in the tissues from patients with psoriasis and rheumatoid arthritis (43, 44), diseases that are associated with chronic inflammation. The expression of miR-146a in synovial fibroblasts from patients with rheumatoid arthritis was higher than that in fibroblasts from patient with osteoarthritis (45).

In vitro studies also demonstrated that miR-146a expression was rapidly increased in response to IL-1β and TNF-α in a variety types of cells including human lung fibroblasts, A549 cells, BEAS2B cells, primary human airway epithelial cells, primary human airway smooth muscle cells, and human rheumatoid arthritis synovial fibroblasts (39, 40, 43). In this regard, we have demonstrated that expression of miR-146a in response to inflammatory cytokine stimulation was significantly increased in both primary human airway epithelial cells and adult human lung fibroblasts assessed by microarray assay as well as by real time RT-PCR (see data below).

The miR-146 family is composed of two members, miR-146a and miR-146b, that are located on chromosomes 5 and 10, respectively. While miR-146a is not expressed under normal conditions, it is rapidly induced in response to a variety of stimuli including IL-1β, TNF-α or LPS stimulation (40, 26). Up-regulated miR-146a is known to target IL-1 receptor associated kinase (IRAK1) and TNF-α receptor-associated factor (TRAF6), and by which mechanism, miR-146a can negatively regulate the cytokine signaling. In addition to IRAK1 and TRAF6, miR-146a also has homologies with sequences in the 3' UTR of many proteins that serve regulatory functions.

The following materials and methods are provided to facilitate the practice of the present example.

Collagen Gel Contraction

Sub-confluent HFL-1 cells were transfected with a non-targeting control-siRNA, a siRNA that specifically targets either Smad2 or Smad3. For miR-146a mimic studies, sub-confluent HFL-1 cells were transfected with a negative control miRNA (NC-miRNA) or a miR-146a mimic for 6 hours followed by culture in 10% FCS-DMEM overnight. Cells were then trypsinized and cast into collagen gels ($3 \times 10^5$ cells/ml). Gels were allowed to contract in serum free DMEM or in the presence of TGF-β1 (100 pM) for 2 days. Gel size was measured with an image analyzer.

VEGF Production

HFL Sub-confluent HFL-1 cells were transfected with a non-targeting control-siRNA, a siRNA that specifically targets either Smad2 or Smad3. Cells were then treated with or without TGF-β1 (100 pM) for 24 hours. VEGF production was quantified by ELISA, and cell number was counted with a Coulter Counter.

MicroRNA Preparation and Quantification.

Eight strains of normal adult lung fibroblasts were treated with or without IL-β1 plus TNF-α in serum free DMEM (control) for 24 hours. Cells were then harvested using TRIzol® Reagent (Invitrogen, Carlsbad, Calif.). MiR-146a expression was quantified using real time RT-PCR following the manufacture's instruction (Applied Biosystems, Carlsbad, Calif.).

Immunoblotting and Immunofluourescence

Protein levels of Smad2, 3, 4, and β-actin (as loading control) will be detected by immunoblotting. The level of each Smad protein will be imaged and scanned with a Typhoon scanner and quantified relative to β-actin using the Image J program (NIH image analysis software). Data will be expressed as relative density of each Smad protein and statistical differences will be estimated from at least 3 separate experiments.

Total RNA will also be extracted from the cells using Trizol reagent and expression of Smad2, 3, 4 and rRNA (as internal control) will be quantified using the real time RT-PCR.

Status of activated Smad proteins will be assessed by the following methods: 1: Immunoblotting phosphorylated Smad 2, 3 and 4. To accomplish this, proteins from whole cell lysates and from separated nuclear and cytoplasic extracts will be immunoblotted for phosphorylated Smad2, 3 and 4. As loading controls, β-actin will be used for whole cell and cytoplasic lysates and TATA binding protein (TBP) will be used to control for nuclear protein loading. Bands will be imaged and quantified as described above and comparison will be based on at least three separate experiments. 2: Immunofluorescence staining to detect nuclear translocation of Smad proteins. After transfection of miR-146a mimic or control and overnight culture in 10% FCS-DMEM, cells will be trypsinized and plated into 8-chamber slides. The next day, cells will be treated with or without TGF-β1 for 24 hours. Cells will then be fixed and permeabilized. Nuclear translocation of Smad2, 3 and 4 will be detected. Cells will be counted and nuclear localization compared from at least three separate experiments. 3: Electrophoresis of mobility shift assay (EMSA). After transfection of miR-146a mimic, cells will be treated with TGF-β1 for 24 hours. Nuclear proteins will be extracted using a commercially available kit. EMSA for Smad3/4 will be performed. Bands will be imaged and quantified as described above.

miR-146a Mimic Blocks TGF-β1 Signaling

In Example 1, we demonstrated that miR-146a has homology with the 3' UTR for the cyclo-oxygenase 2 (COX2) protein, and that miR-146s can directly modulate COX2 expression and regulate the production of $PGE_2$. In the current example we show that miR-146a has homologies with Smad 2, 3 and 4 (www.targetscan.org) (see FIG. 12), suggesting that miR-146a can modulate TGF-β1 signaling through suppressing Smad2, 3 and 4 proteins. Thus, it appears that miR-146a, which can be induced by inflammatory cytokines, regulates the ability of fibroblasts to respond to TGF-β1 stimulation.

Figure 13:
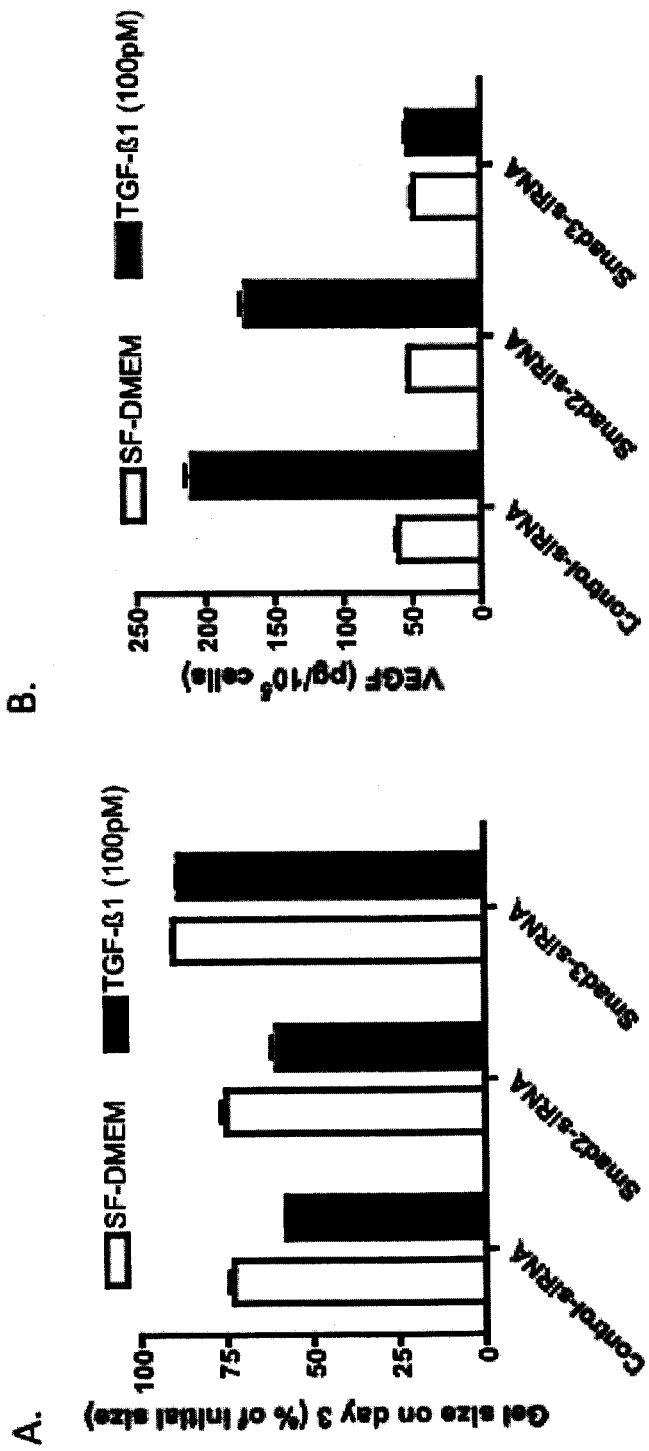
FIG. 13. Bar graphs demonstrating that Smad3 but not Smad2 mediates collagen gel contraction (FIG. 13A) and VEGF production (FIG. 13B) in response to TGF-β1 stimulation of human fetal lung fibroblast (HFL-1) cells.

Smad proteins mediate TGF-β1 signaling in variety kinds of cells including lung fibroblasts. Using both small RNA interference in human lung fibroblasts (35) and genetically deficient mouse cells (37), we have previously demonstrated that Smad3 is required for lung fibroblast-mediated collagen gel contraction (FIG. 13A) and α-smooth muscle actin expression (α-SMA) (35) in response to TGF-β1. In contrast, Smad2 seems not to be necessary for this effect. Similarly, TGF-β1 stimulates vascular endothelial growth factor (VEGF) production by human lung fibroblasts and this effect is also mediated by Smad3, but not by Smad2 (FIG. 13B) (36). These findings indicate that Smad3 is crucial in mediating several fibroblast responses to TGF-β1. While Smad3 appears responsible for mediating many functions of fibroblasts in response to TGF-β1, studies have shown that Smad2 mediates TGF-β1 action on other cell types including IgA switching in B cells and migration of keratinocytes during wound healing (46, 47).

Figure 14:
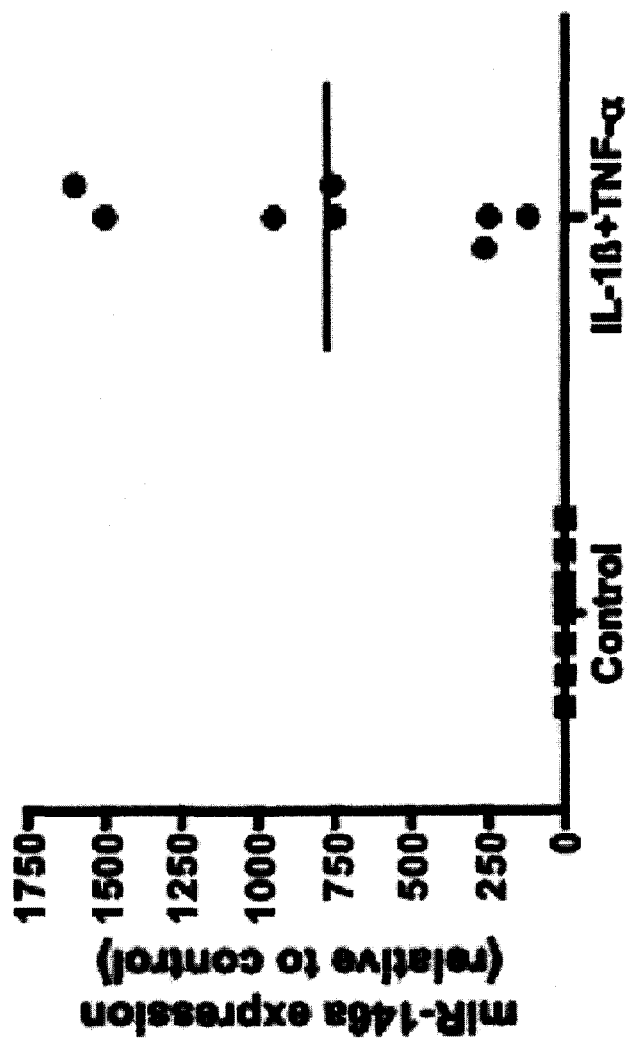
FIG. 14. A graph demonstrating that miR-146a expression was up regulated by IL-1β and TNF-α in human lung fibroblasts. Eight strains of normal adult lung fibroblasts were treated with or without IL-β1 plus TNF-α in serum free DMEM (control) for 24 hours. Vertical axis: miR-146a expression level compared to untreated cells (control); horizontal axis: cells treated with or without cytokines.
Figure 15:
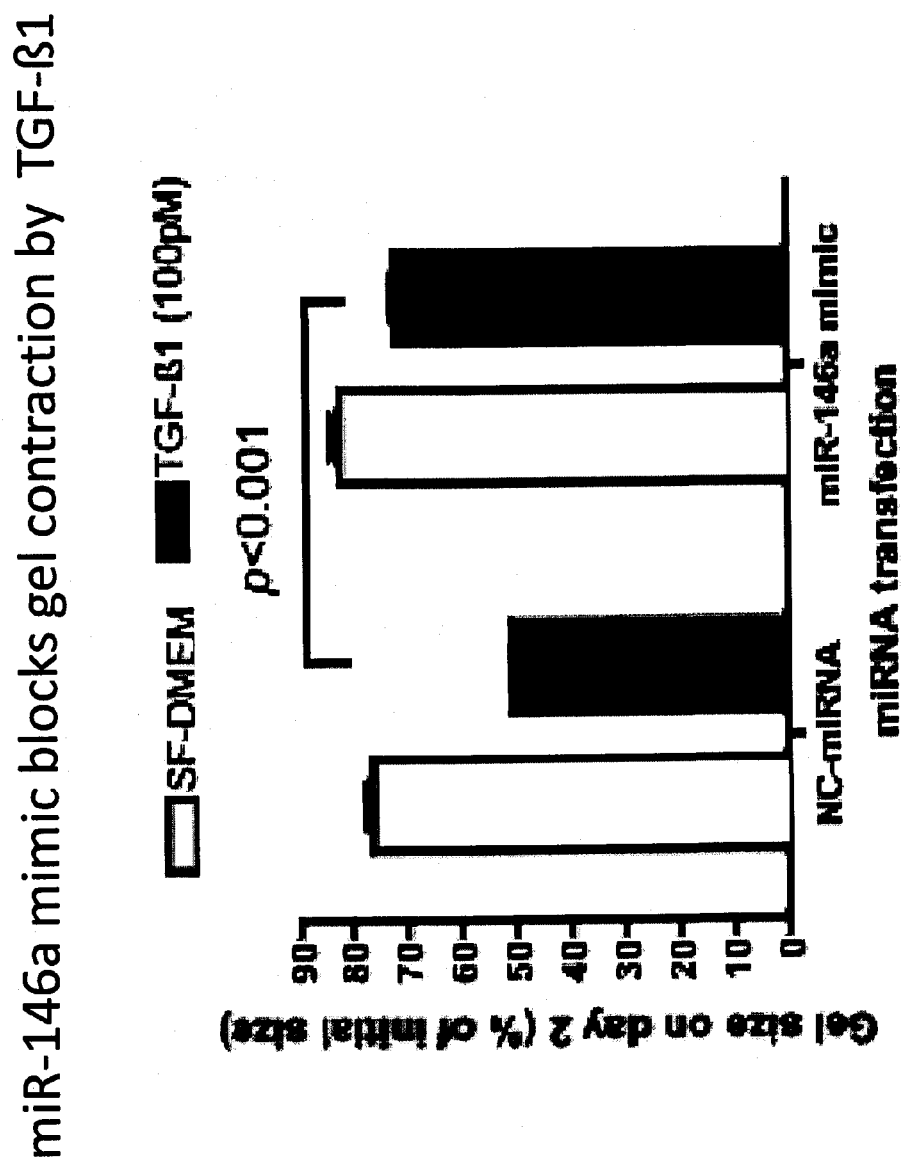
FIG. 15. A bar graph demonstrating that miR-146a mimic blocks TGF-β1 augmented collagen gel contraction by HFL-1 cells. Sub-confluent HFL-1 cells were transfected with a negative control miRNA (NC-miRNA) or a miR-146a mimic for 6 hours followed by culture in 10% FCS-DMEM overnight. Trypsinized cells were cast into collagen gels at 3×$10^5$ cells/ml). Gels were allowed to contract in serum free DMEM (SF-DMEM, open bar) or in the presence of TGF-β1 (100 pM, closed bar) for 2 days. Vertical axis: gel size expressed as percent of initial size (%); horizontal axis: cells transfected with miRNAs.

We extended our previous studies in Example 1, demonstrating IL-1β/TNF-α induction of miR-146a in several cell types, by showing that human lung fibroblasts respond similarly (FIG. 14). Our data also show that miR-146a mimic blocks TGF-β1 augmented collagen gel contraction by HFL-1 cells. See FIG. 15. Finally, we also have preliminary data from immunoblotting assays on stimulated cells which indicate that transfection of exogenous miR-146a mimic does indeed suppress Smad3 and Smad4 protein expression (data not shown).

In other experiments we have shown that following transfection of miR-146a, and culture in the presence and absence of TGF-β1 (100 pM) in serum free DMEM for 6, 24 and 48 hours, expression of α-SMA mRNA is altered. Indeed, preliminary results show that exogenous miR-146a mimic suppresses α-SMA expression regardless of whether cells have been stimulated with TGF-β1 or not (FIG. 16).

As shown in the preliminary data (above), we have demonstrated that miR-146a mimic blocks TGF-β1-augmented collagen gel contraction, which is a Smad3 mediated effect. Since VEGF and α-SMA are also stimulated by TGF-β1 acting through Smad signaling, we anticipate that miR-146a will also block TGF-β1 stimulation of VEGF release and α-SMA expression. In contrast, we expect that fibronectin production in response to TGF-β1 stimulation will not be affected by miR-146a, in that stimulation of fibronectin by TGF-β1 is mediated by a Smad-independent pathway. It is possible, of course, that stimulation of fibronectin production will also be blocked by an effect of miR-146a independent of its effect on Smad3.

In summary, our data implicate miR-146a as a Smad modulator which plays a key mechanistic role in mediating IL-1β and TNF-α inhibition of TGF-β1 signaling.

LITERATURE CITED BY NUMERIC REFERENCE HEREIN

1. Global Strategy for Diagnosis. Management and Prevention of COPD. 2008. www.goldcopd.com).
2. Anthonisen et al., 2002, Smoking and lung function of lung health study participants after 11 years, Am. J. Respir. Crit. Care Med., 166:675-679.
3. Murray et al., 1997, Lancet 349:1436.
4. Turato et al., 1995, Effect of smoking cessation on airway inflammation in chronic bronchitis, Am. J. Respir. Crit. Care Med., 152:1262-1267.
5. Rutgers et al., 2000, Thorax, 55:12.
6. Hogg et al., 2004, The nature of small-airway obstruction in chronic obstructive pulmonary disease, N. Engl. J. Med., 350:2645-2653.
7. Willemse et al., Eur Respir J 26, 835 (November, 2005).
8. S. D. Shapiro, G. L. Snider, S. I. Rennard, in Textbook of Respiratory Medicine, R. J. Mason, Broadus, V. C., Murray, J. F., and Nadel, J. A., Ed. (Elsevier, Philadelphia, 2005), vol. 1, pp. 1115-1167.
9. S. I. Rennard, in Chronic Obstructive Pulmonary Disease, P. M. A. Calverley, W. MacNee, N. B. Pride, S. I. Rennard, Eds. (Arnold, London, 2003), pp. 139-150.
10. P. Laurent, A. Janoff, H. M. Kagan, Am Rev Respir Dis 127, 189 (1983).
11. M. Osman, Am Rev Respir Dis 132, 640 (1985).
12. H. Wang et al., Am. J. Respir Cell Mol Biol 25, 772 (2001).
13. Y. Nakamura et al., Am J Respir Crit. Care Med 151, 1497 (1995).
14. P. Montuschi et al., Am J Respir Crit. Care Med 161, A821 (2000).
15. S. Togo et al., 2008, Lung fibroblast repair functions in patients with chronic obstructive pulmonary disease are altered by multiple mechanisms, Am. J. Respir. Crit. Care Med., 178:248-260.
16. T. Kohyama et al., Am J Physiol 281, L1257 (2001).
17. P. Bitterman, S. Rennard, T. Ozaki, S. Adelberg, R. G. Crystal, Am Rev Respir Dis 127, A271 (1983).
18. V. Lama, B. B. Moore, P. Christensen, G. B. Toews, M. Peters-Golden, Am J Respir Cell Mol Biol 27, 752 (December, 2002).
19. S. Huang, S. H. Wettlaufer, C. Hogaboam, D. M. Aronoff, M. Peters-Golden, Am J Physiol Lung Cell Mol Physiol 292, L405 (February, 2007).
20. S. K. Huang, S. H. Wettlaufer, J. Chung, M. Peters-Golden, Am J Respir Cell Mol Biol 39, 482 (October, 2008).
21. S. P. Nana-Sinkam et al., Am J Respir Crit. Care Med 179, 4 (Jan. 1, 2009).
22. S. Griffiths-Jones, R. J. Grocock, S. van Dongen, A. Bateman, A. J. Enright, Nucleic Acids Res 34, D140 (Jan. 1, 2006).
23. N. Shanmugam, M. A. Reddy, R. Natarajan, J Biol Chem 283, 36221 (Dec. 26, 2008).
24. A. Strillacci et al., Exp Cell Res, 315, 1439-1447 (May 1, 2009).
25. A. Chakrabarty et al., Proc Natl Acad Sci USA 104, 15144 (Sep. 18, 2007).
26. Taganov et al., 2006, NF-kappaB-dependent induction of microRNA miR-146, an inhibitor targeted to signaling proteins of innate immune responses, Proc. Natl. Acad. Sci. U.S.A., 103:12481-12486.
27. Aubert et al., 1994, Transforming growth factor beta 1 gene expression in human airways, Thorax, 49:225-232.
28. Takizawa et al., 2001, Increased expression of transforming growth factor-beta1 in small airway epithelium from tobacco smokers and patients with chronic obstructive pulmonary disease (COPD), Am J Respir Crit. Care Med, 163:1476-1483.
29. Vignola et al., 1997, Transforming growth factor-beta expression in mucosal biopsies in asthma and chronic bronchitis, Am J Respir Crit. Care Med 1997, 156:591-599.
30. Shim et al., 2005, TAK1, but not TAB1 or TAB2, plays an essential role in multiple signaling pathways in vivo, Genes Dev, 19:2668-2681.
31. Wang et al., 2002, Requirement of mitogen-activated protein kinase kinase 3 (MKK3) for activation of p38alpha and p38delta MAPK isoforms by TGF-beta 1 in murine mesangial cells, J Biol Chem, 277:47257-47262.
32. Xin et al., 2007, Akt activation and augmented fibronectin production in hyperhexosemia, Am J Physiol Endocrinol Metab, 293:E1036-1044.
33. Kang et al., 2007, Semaphorin 7A plays a critical role in TGF-beta1-induced pulmonary fibrosis, J Exp Med, 204:1083-1093.

34. Sumiyoshi et al., 2003, Smad3 regulate collagen gel contraction by human dermal fibroblasts, Br J Dermatol, 149:464-470.
35. Kobayashi et al., 2006, Smad3 mediates TGF-beta1-induced collagen gel contraction by human lung fibroblasts, Biochem Biophys Res Commun, 339:290-295.
36. Kobayashi et al., 2005, Smad3 mediates TGF-beta1 induction of VEGF production in lung fibroblasts, Biochem Biophys Res Commun, 327:393-398.
37. Liu et al., 2003, Smad3 mediates the TGF-beta-induced contraction of type I collagen gels by mouse embryo fibroblasts, Cell Motil Cytoskeleton, 54:248-253.
38. Asirvatham et al., 2009, miRNA regulation of cytokine genes, Cytokine, 45:58-69.
39. Liu et al., 2009, MicroRNA-146a modulates human bronchial epithelial cell survival in response to the cytokine-induced apoptosis, Biochem Biophys Res Commun, 380:177-182.
40. Perry et al., 2008, Rapid changes in microRNA-146a expression negatively regulate the IL-1beta-induced inflammatory response in human lung alveolar epithelial cells, J Immunol, 180:5689-5698.
41. Yanaihara et al., 2006, Unique microRNA molecular profiles in lung cancer diagnosis and prognosis, Cancer Cell, 9:189-198.
42. Zhang et al., 2007, microRNAs as oncogenes and tumor suppressors, Dev Biol, 302:1-12.
43. Nakasa et al., 2008, Expression of microRNA-146 in rheumatoid arthritis synovial tissue, Arthritis Rheum, 58:1284-1292.
44. Sonkoly et al., 2007, MicroRNAs: novel regulators involved in the pathogenesis of Psoriasis?, PLoS One, 2:e610.
45. Stanczyk et al., 2008, Altered expression of MicroRNA in synovial fibroblasts and synovial tissue in rheumatoid arthritis, Arthritis Rheum, 58:1001-1009.
46. Ross et al., 2006, Smads orchestrate specific histone modifications and chromatin remodeling to activate transcription, EMBO J, 25:4490-4502.
47. Klein et al., 2006, B cell-specific deficiency for Smad2 in vivo leads to defects in TGF-beta-directed IgA switching and changes in B cell fate, J Immunol, 176:2389-2396.
48. Kamio et al., 2007, Prostacyclin analogs inhibit fibroblast contraction of collagen gels through the cAMP-PKA pathway, Am J Respir Cell Mol Biol, 37:113-120.
49. Wen et al., 2004, Interferon-gamma inhibits transforming growth factor-beta production in human airway epithelial cells by targeting Smads, Am J Respir Cell Mol Biol, 30:816-822.
50. Liu X, et al., 2008, NF-kappaB mediates the survival of human bronchial epithelial cells exposed to cigarette smoke extract, Respir Res, 9:66.
51. Liu X, 2007, STAT3 activation inhibits human bronchial epithelial cell apoptosis in response to cigarette smoke exposure, Biochem Biophys Res Commun, 353:121-126.
52. Houde et al., 2009, Transforming growth factor-beta1 (TGF-beta1) induces human osteoclast apoptosis by up-regulating Bim, J Biol Chem, 284:23397-23404.
53. Luo et al., 2009, Interleukin-1 beta regulates proximal tubular cell transforming growth factor beta-1 signalling, Nephrol Dial Transplant, 24:2655-2665.
54. Bauge et al., 2007, Interleukin-1beta impairment of transforming growth factor beta1 signaling by down-regulation of transforming growth factor beta receptor type II and up-regulation of Smad7 in human articular chondrocytes, Arthritis Rheum, 56:3020-3032.
55. Roman-Blas et al., 2007, Modulation of TGF-beta signaling by proinflammatory cytokines in articular chondrocytes, Osteoarthritis Cartilage, 15:1367-1377.
56. Holz O, Zuhlke I, Jaksztat E, Muller K C, Welker L, Nakashima M, Diemel K D, Branscheid D, Magnussen H, Jones R A. Lung fibroblasts from patients with emphysema show a reduced proliferation rate in culture. Eur Respir J 2004; 24(4):575-579.
57. Noordhoek J A, Postma D S, Chong L L, Vos J T, Kauffman H F, Timens W, van Straaten J F. Different proliferative capacity of lung fibroblasts obtained from control subjects and patients with emphysema. Exp Lung Res 2003; 29(5):291-302.
58. Nobukuni S, Watanabe K, Inoue J, Wen F Q, Tamaru N, Yoshida M. Cigarette smoke inhibits the growth of lung fibroblasts from patients with pulmonary emphysema. Respirology 2002; 7(3):217-223.
59. Plantier L, Rochette-Egly C, Goven D, Boutten A, Bonay M, Leseche G, Fournier M, Crestani B, Boczkowski J. Dysregulation of elastin expression by fibroblasts in pulmonary emphysema: Role of cellular retinoic acid binding protein 2. Thorax 2008; 63(11):1012-1017.
60. Plantier L, Marchand-Adam S, Marchal-Somme J, Leseche G, Fournier M, Dehoux M, Aubier M, Crestani B. Defect of hepatocyte growth factor production by fibroblasts in human pulmonary emphysema. Am J Physiol Lung Cell Mol Physiol 2005; 288(4):L641-647.

While certain preferred embodiments of the present invention have been described and specifically exemplified above, it is not intended that the invention be limited to such embodiments. Various modifications may be made to the invention without departing from the scope and spirit thereof as set forth in the following claims.

What is claimed is:

1. A method for reducing protein production from a COX-2 mRNA molecule in a lung fibroblast comprising administering an effective amount of miR-146a or a mimic of miR-146a to said fibroblast, said miR-146a or mimic hybridizing to a 3' end of said COX-2 mRNA, thereby inhibiting COX-2 protein production from said mRNA in a pharmaceutically acceptable carrier, said miR-146a or a mimic of miR-146a being administered via a route selected from the group consisting of inhalation, or intranasal administration.

2. The method of claim 1, wherein said COX-2 mRNA is degraded.

3. The method of claim 2, wherein degradation of said COX-2 mRNA is correlated with decreased $PGE_2$ production.

4. The method of claim 2, wherein degradation of said COX-2 mRNA is correlated with increased fibroblast repair function.

5. The method of claim 2, wherein said lung fibroblast is present in a patient having chronic obstructive pulmonary disorder (COPD).

6. The method of claim 5, further comprising assessing said patient for an alleviation of COPD symptoms.

7. The method of claim 6, wherein said miR-146a or mimic is present in an aerosolized formulation for administration via inhalation.

8. The method of claim 7, wherein said miR-146a or mimic is encapsulated in a liposome or microvessicle.

9. The method of claim 7, said method comprising administration of at least one anti-inflammatory agent.

10. The method of claim 1, wherein said administration results in reduced protein production encoded by at least one other mRNA selected from the group consisting of Smad2, Smad3, Smad4, Cox-1, cPLA2 and mPGES1.

11. The method of claim 1, further comprising administration of at least one miRNA, or mimic thereof, selected from the group consisting of miR-122, miR-143, miR-144, miR-101, miR-16, miR-26, miR-138, and miR-24.

12. The method of claim 11, wherein the at least one miRNA is miR-144 or mimic thereof.

* * * * *